(12) United States Patent
Weingarten et al.

(10) Patent No.: US 7,897,776 B2
(45) Date of Patent: Mar. 1, 2011

(54) SULFONAMIDE CONTAINING COMPOUNDS FOR TREATMENT OF INFLAMMATORY DISORDERS

(75) Inventors: M. David Weingarten, Cumming, GA (US); Charles Q. Meng, Duluth, GA (US); James A. Sikorski, Atlanta, GA (US); Raymond Ng, Alpharetta, GA (US); Wei Zhang, Alpharetta, GA (US)

(73) Assignee: Salutria Pharmaceuticals LLC, Alpharetta, GA (US)

( * ) Notice: Subject to any disclaimer, the term of this patent is extended or adjusted under 35 U.S.C. 154(b) by 238 days.

(21) Appl. No.: 12/148,966

(22) Filed: Apr. 23, 2008
(Under 37 CFR 1.47)

(65) Prior Publication Data
US 2009/0270454 A1    Oct. 29, 2009

Related U.S. Application Data

(60) Provisional application No. 60/925,778, filed on Apr. 23, 2007.

(51) Int. Cl.
*C07D 421/00* (2006.01)
*C07D 207/00* (2006.01)

(52) U.S. Cl. .......... 546/208; 546/209; 548/519

(58) Field of Classification Search .......... 546/208, 546/209; 548/519
See application file for complete search history.

(56) References Cited

U.S. PATENT DOCUMENTS

| | | | |
|---|---|---|---|
| 4,954,514 A | 9/1990 | Kita et al. | |
| 5,262,439 A | 11/1993 | Parthasarathy | |
| 5,874,478 A | 2/1999 | Hendler et al. | |
| 5,981,603 A | 11/1999 | Hendler | |
| 6,121,272 A | 9/2000 | Almstead et al. | |
| 6,121,319 A | 9/2000 | Somers | |
| 6,147,250 A | 11/2000 | Somers | |
| 6,670,398 B2 | 12/2003 | Edwards et al. | |
| 6,852,878 B2 | 2/2005 | Meng et al. | |
| 2005/0070582 A1 | 3/2005 | Li et al. | |
| 2005/0234046 A1 | 10/2005 | Zhao et al. | |
| 2007/0037794 A1 | 2/2007 | Ungashe et al. | |

FOREIGN PATENT DOCUMENTS

| | | |
|---|---|---|
| EP | 0 348 203 | 12/1989 |
| EP | 0 405 788 | 1/1991 |
| FR | 2130975 | 11/1972 |
| FR | 2133024 | 11/1972 |
| FR | 2134810 | 12/1972 |
| FR | 2140769 | 1/1973 |
| FR | 2140771 | 1/1973 |
| FR | 2168137 | 8/1973 |
| WO | WO 91/01124 | 2/1991 |
| WO | WO 98/51662 | 11/1998 |
| WO | WO 01/70757 | 9/2001 |
| WO | WO 2004/037817 | 5/2004 |
| WO | WO 2005/030721 | 4/2005 |

OTHER PUBLICATIONS

Dranoff G.; Cytokines in cancer pathogenesis and cancer therapy. Nat Rev Cancer 2004;4:11-22.
O'Byrne et al., Chronic immune activation and inflammation as the cause of malignancy. Br J Cancer 2001;85:473-783.
Balkwill et al. Inflammation and cancer: back to Virchow Lancet 2001;357:539-45.
Coussens et al. Inflammation and cancer. Nature 2002;420:860-7.
Novel Phenolic Antioxidants As Multifunctional Inhibitors of Inducible VCAM-1 Expression for Use in Atherosclerosis, Bioorganic & Med Chem Ltrs. 12(18), 2545-2548, 2002).

*Primary Examiner*—Nizal S Chandrakumar
(74) *Attorney, Agent, or Firm*—King & Spalding

(57) ABSTRACT

Provided are compounds, pharmaceutical compositions and methods of treatment or prophylaxis of an inflammatory condition, in particular asthma. The compounds are of the general Formula I, or a pharmaceutically acceptable salt, ester, prodrug or derivative thereof:

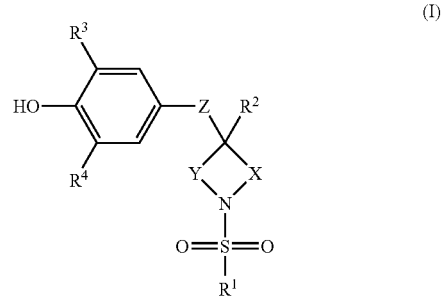

(I)

wherein:
X and Y are independently selected from —$CH_2$— or —$CH_2$—$CH_2$—; Z is selected from $S(O)_m$ or $Se(O)_m$ and m is 0, 1 or 2; $R^1$ is optionally substituted heteroaryl or heterocyclic; $R^2$ is selected from the group consisting of hydrogen, $C_1$-$C_6$ straight alkyl, and $C_1$-$C_6$ branched alkyl, wherein all may be optionally substituted; and $R^3$ and $R^4$ are alkyl.

20 Claims, No Drawings

SULFONAMIDE CONTAINING COMPOUNDS FOR TREATMENT OF INFLAMMATORY DISORDERS

CROSS-REFERENCE TO RELATED APPLICATION

This application claims priority to U.S. Provisional Application No. 60/925,778 filed Apr. 23, 2007.

FIELD OF THE INVENTION

The present invention is in the area of methods and compositions for the treatment and prophylaxis of inflammatory disorders and, in particular, for the treatment or prophylaxis of respiratory inflammatory diseases such as asthma.

BACKGROUND OF THE INVENTION

A growing consensus among scientists is that common disorders such as asthma, atherosclerosis, colon cancer, and Alzheimer's disease are all caused in part by a chronic inflammatory syndrome. Generally, chronic inflammation is involved in diseases as diverse as allergy, anemia, aortic valve stenosis, arthritis, atherosclerosis, cancer, heart valve dysfunction, obesity, congestive heart failure, digestive system diseases, and Alzheimer's disease (Brouqui et al. 1994; Devaux et al. 1997; De Keyser et al. 1998). Chronic inflammation inevitably causes tissue damage and is accompanied by simultaneous attempts at healing and repair. The exact nature, extent and time course of chronic inflammation is variable, and depends on a balance between the causative agent and the attempts of the body to remove it. Disorders associated with inflammation are debilitating to individuals suffering from them and cost billions in reduced productivity and increased medical expenses.

Asthma is one of the most common chronic health conditions and is on the rise due to irritants such as pollution and chronic exposure to indoor allergens such as cigarette smoke, cockroaches, dust mites, mold, animals, pollen, cold air, exercise, stress, and respiratory infections. Asthma and related respiratory disorders such as chronic obstructive pulmonary disease (COPD) are chronic or recurring inflammatory conditions in which the airway develops increased responsiveness to various stimuli, characterized by bronchial hyperresponsiveness, inflammation, increased mucus production, and intermittent airway obstruction.

Many inflammatory disorders are mediated by certain cytokines. These include the IL-6 and IL-8 families. Regulation of these and other related cytokines can be a strategy when overstimulation of the immune responses leads to adverse events.

Cytokines are produced predominantly by activated immune cells such as microglia and are involved in the amplification of inflammatory reactions. These include IL-1, IL-6, TNF-α, and TGF-β.

Anti-Inflammatory Compounds

Derivatives of probucol have been developed as therapeutics, for example, for the treatment of cardiovascular disease and as anti-inflammatory agents. Probucol contains two hydroxyl groups and can be modified to form mono-substituted or di-substituted derivatives. Mono-esters and ethers of probucol have been reported to be useful in the treatment of inflammatory diseases such as rheumatoid arthritis, osteoarthritis, asthma, and dermatitis. Methods for treating transplant rejection using mono-substituted derivatives of probucol also have been reported. See U.S. Pat. No. 6,670,398.

U.S. Pat. No. 5,262,439 to Parthasarathy discloses analogs of probucol with increased water solubility in which one or both of the hydroxyl groups are replaced with ester groups that increase the water solubility of the compound. A series of French patents disclose that certain probucol derivatives are hypocholesterolemic and hypolipemic agents: FR 2168137 (bis 4hydroxyphenylthioalkane esters); FR 2140771 (tetralinyl phenoxy alkanoic esters of probucol); FR 2140769 (benzofuryloxyalkanoic acid derivatives of probucol); FR 2134810 (bis-(3-alkyl-5-t-alkyl-4-thiazole-5-carboxy)phenylthio)alkanes; FR 2133024 (bis-(4 nicotinoyloxyphenylthio)-propanes; and FR 2130975 (bis(4-phenoxyalkanoyloxy)phenylthio)alkanes).

European Patent No. 0348203 to Shionogi Seiyaku Kabushiki Kaisha discloses phenolic thioethers which inhibit the denaturation of LDL and the incorporation of LDL by macrophages. Hydroxamic acid derivatives of these compounds are disclosed in European Patent No. 0405788 and are alleged as useful for the treatment of arteriosclerosis, ulcer, inflammation and allergy. Carbamoyl and cyano derivatives of the phenolic thioethers are disclosed in U.S. Pat. No. 4,954,514 to Kita, et al.

U.S. Pat. No. 6,121,319, and corresponding WO 98/51662 and U.S. Pat. No. 6,147,250 filed by AtheroGenics, Inc., describe certain probucol derivatives and their use for the treatment of disorders mediated including inflammatory and cardiovascular disorders.

WO 01/70757 (also U.S. Pat. No. 6,852,878) filed by AtheroGenics, Inc. describes the use of certain thioethers of the following formula, and pharmaceutically acceptable salts thereof:

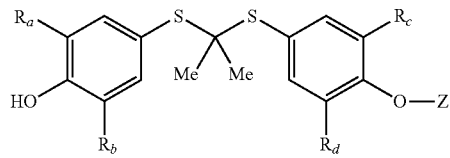

wherein $R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and Z is (i) a substituted or unsubstituted carbohydrate, (ii) a substituted or unsubstituted alditol, (iii) $C_{1-10}$ alkyl or substituted $C_{1-10}$ alkyl, terminated by sulfonic acid, (iv) $C_{1-10}$alkyl or substituted $C_{1-10}$ alkyl, terminated by phosphonic acid, (v) substituted or unsubstituted $C_{1-10}$ alkyl-O—C(O)—$C_{1-10}$ alkyl, (vi) straight chained polyhydroxylated $C_{3-10}$ alkyl; (vii) —($CR_2$)$_{1-6}$—COOH, wherein R is independently hydrogen, halo, amino, or hydroxy, and wherein at least one of the R substituents is not hydrogen; or (viii) —($CR_2$)$_{1-6}$—X, wherein X is aryl, heteroaryl, or heterocycle, and R is independently hydrogen, halo, amino, or hydroxy.

Meng et al. disclose a series of phenolic inhibitors of TNF-inducible expression of VCAM-1 with concurrent antioxidant and lipid-modulating properties. The compounds disclosed have demonstrated efficacies in animal models of atherosclerosis and hyperlipidemia. (Novel Phenolic Antioxidants As Multifunctional Inhibitors Of Inducible VCAM-1 Expression For Use In Atherosclerosis, *Bioorganic & Med Chem. Ltrs.* 12(18), 2545-2548, 2002).

WO 05/030721 to Nippon Chemiphar Co., Ltd. describes certain piperidine derivatives as antioxidants. These compound are of the formula:

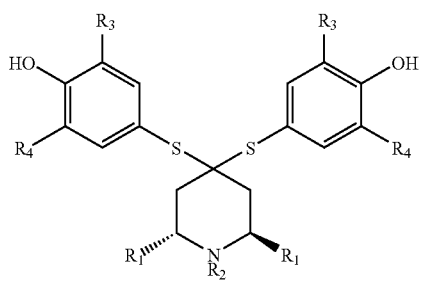

wherein $R_1$ represents an alkyl group having 1-8 carbon atoms or the like; $R_2$ represents a hydrogen atom, an alkyl group having 1-8 carbon atoms, an alkylcarbonyl group having 2-8 carbon atoms or the like; and $R_3$ and $R_4$ may be the same or different and represent alkyl groups having 1-8 carbon atoms or the like.

WO 91/01124 and related U.S. Pat. No. 5,981,603 and U.S. Pat. No. 5,874,478 to Biodor U.S. Holding and Vyrex Corp. also describes certain compounds for use as antioxidants for treatment of viral infections. These compounds are of the general formula:

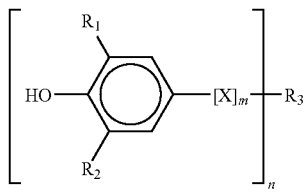

wherein n=1, 2, 3, or 4, wherein m=0 or 1, wherein X represents O, S or $CH_2$, wherein $R^1$ represents hydrogen or tertiary butyl or lower alkyl of from one to six carbon atoms, inclusive, $R_2$ represents tertiary butyl or lower alkyl of from one to six carbon atoms, inclusive, and wherein $R_3$ represents hydrogen or alkyl or aryl or mixed alkyl/aryl, containing a total of 5 to 25 carbon atoms. One of the compounds identified in the application is of the following structure:

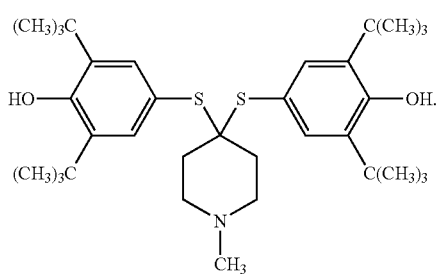

PCT Publication No. WO 04/037817 to Mitsubishi Pharma Corp. describes certain N-oxide compounds of the formula 1:

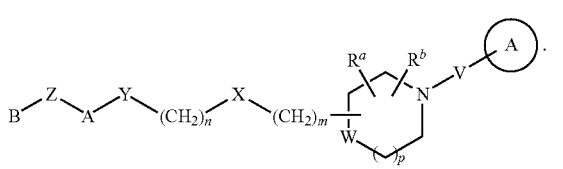

U.S. Pat. No. 6,121,272 to the Proctor & Gamble Company discloses certain compounds which are described as inhibitors of metalloproteases. These compounds are of the general formula I:

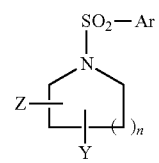

wherein n is an integer from 1 to 3, and 0 to 2 additional heteroatoms, chosen from O, N, or S, may occur in the backbone of the ring in the place of carbon, and where S occurs it may be in the form S, SO, or $SO_2$ and where N occurs it is in the form $NR_5$ and $R_5$ is chosen from hydrogen, alkyl, heteroalkyl, heteroaryl, aryl, $SO_2R_{10}$, $COR_{11}$, $CSR_{12}$, $PO(R_{13})_2$; Z is independently one or more of $(CH_2)_m(CR_1R_2)_oSR_3$; Y is independently one or more of hydrogen, hydroxy, oxo, a spiro moiety, $SOR_6$, $SO_2R_{10}$, alkoxy, aryloxy, alkyl aryl, heteroaryl, $COR_{22}CSR_{12}$, amino; and Ar is substituted or unsubstituted; alkyl, aryl, carbocyclyl, heterocyclyl, or heteroaryl.

There remains a need for improved compounds and methods for the treatment of chronic inflammatory disorders. In particular there is a need for improved treatments for chronic respiratory inflammatory disorders such as asthma.

It is therefore an object of the present invention to provide new compounds, pharmaceutical compositions and methods for the treatment of inflammatory disorders.

It is a further object of the invention to provide compounds, compositions and methods of treating disorders and diseases mediated by inflammatory cytokines, including respiratory and cardiovascular inflammatory diseases.

SUMMARY OF THE INVENTION

It has been discovered that certain sulfonamide-containing compounds are useful in the treatment or prophylaxis of certain inflammatory conditions. In particular, compounds described below are useful for treating respiratory inflammation such as found in asthma as well as other inflammatory disorders such as atherosclerosis or arthritis.

In one embodiment, compounds, pharmaceutical compositions and methods of treatment or prophylaxis of an inflammatory condition, and in particular asthma, comprising administering to a host in need thereof a compound of Formula I, or a pharmaceutically acceptable salt, ester, prodrug or derivative thereof are provided:

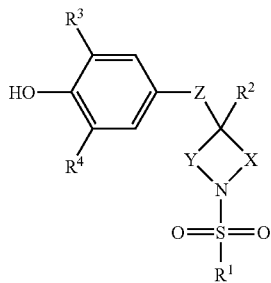

(I)

wherein:
X and Y are independently selected from —CH$_2$— or —CH$_2$—CH$_2$—;
Z is selected from S(O)$_m$ or Se(O)$_m$;
m is 0, 1 or 2;
R$^1$ is heteroaryl or heterocyclic, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^5$R$^6$, oxo, cyano, carboxy, carboxyalkyl, alkoxycarbonyl, —OR$^5$, —C(O)R$^5$, —C(O)—NH$_2$, —C(O)—N(H)R$^5$, —C(O)—N(H)OR$^5$, —C(O)—NR$^5$R$_6$, —NR$^6$C(O)R$^5$, —NR$^6$C(O)NR$^5$R$^6$, —OC(O)NR$^5$R$^6$, —NR$^6$C(O)OR$^5$, —S(O)$_n$—R$^5$, —S(O)$_2$—NH$_2$, —S(O)$_n$—N(H)R$^5$ and —S(O)$_2$—NR$^5$R$^6$;
n is 0, 1 or 2;
R$^2$ is selected from the group consisting of hydrogen, C$_1$-C$_6$ straight alkyl, and C$_1$-C$_6$ branched alkyl, wherein all may be optionally substituted by one or more selected from the group consisting of halo, hydroxy, heterocyclic, heteroaryl, carboxy, —NR$^5$R$^6$, alkoxycarbonyl, —NR$^6$C(O)R$^5$, —NR$^6$C(O)NR$^5$R$^6$, —NR$^6$C(O)OR$^5$, —OC(O)NR$^5$R$^6$, —OR$^5$, C(O)R$^5$, —S(O)$_n$—R$^5$, —C(O)—NR$^5$R$^6$, and cyano;
R$^3$ and R$^4$ are independently selected from the group consisting of C$_1$-C$_6$ straight alkyl, C$_1$-C$_6$ branched alkyl, and C$_3$-C$_8$ cyclic alkyl;
R$^5$ and R$^6$ are independently selected from the group consisting of hydrogen, C$_1$-C$_6$ straight alkyl, C$_1$-C$_6$ branched alkyl, C$_2$-C$_6$ alkenyl, C$_3$-C$_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^7$R$^8$, oxo, cyano, carboxy, carboxyalkyl, alkoxycarbonyl, —OR$^9$, —C(O)R$^9$, —C(O)—NH$_2$, —C(O)—N(H)R$^7$, —C(O)—NR$^7$R$^8$, —NR$^7$C(O)R$^9$, —NR$^7$C(O)OR$^9$, —S(O)$_n$—R$^9$, —S(O)$_2$—NH$_2$, —S(O)$_2$—N(H)R$^7$ and —S(O)$_2$—NR$^7$R$^8$; and R$^5$ and R$^6$ taken together may form a 4- to 12-membered monocyclic, bicyclic, tricyclic or benzofused ring;
R$^7$ and R$^8$ are independently selected from the group consisting of alkyl, alkenyl and aryl and taken together may form a 4- to 12-membered monocyclic, bicyclic, tricyclic or benzofused ring; and
R$^9$ is independently selected from the group consisting of C$_1$-C$_6$ straight alkyl, C$_1$-C$_6$ branched alkyl, C$_2$-C$_6$ alkenyl, C$_3$-C$_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In one embodiment of Formula I, m is 0.
In one embodiment, R$^3$ and R$^4$ are tert-butyl.
In one embodiment, R$^1$ is heteroaryl. In a separate embodiment, R$^1$ is heterocyclic.
In another principal embodiment, compounds, pharmaceutical compositions and methods of treatment or prophylaxis of an inflammatory condition, and in particular asthma, comprising administering to a host in need thereof a compound of Formula II, or a pharmaceutically acceptable salt, ester, prodrug or derivative thereof are provided:

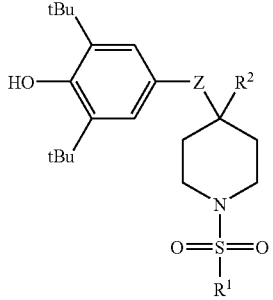

(II)

wherein:
Z is selected from S(O)$_m$ or Se(O)$_m$;
m is 0, 1 or 2;
R$^1$ is heteroaryl or heterocyclic, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^5$R$^6$, oxo, cyano, carboxy, carboxyalkyl, alkoxycarbonyl, —OR$^5$, —C(O)R$^5$, —C(O)—NH$_2$, —C(O)—N(H)R$^5$, —C(O)—N(H)OR$^5$, —C(O)—NR$^5$R$^6$, —NR$^6$C(O)R$^5$, —NR$^6$C(O)NR$^5$R$^6$, —NR$^6$C(O)OR$^5$, —OC(O)NR$^5$R$^6$, —S(O)—R$^5$, —S(O)$_2$—NH$_2$, —S(O)$_n$—N(H)R$^5$ and —S(O)$_2$—NR$^5$R$^6$;
n is 0, 1 or 2;
R$^2$ is selected from the group consisting of hydrogen, C$_1$-C$_6$ straight alkyl, and C$_1$-C$_6$ branched alkyl, wherein all may be optionally substituted by one or more selected from the group consisting of halo, hydroxy, heterocyclic, heteroaryl, carboxy, alkoxycarbonyl, —NR$^5$R$^6$, —NR$^6$C(O)R$^5$, —NR$^6$C(O)NR$^5$R$_6$, —NR$^6$C(O)OR$^5$, —OC(O)NR$^5$R$^6$, —OR$^5$, —C(O)R$^5$, —S(O)$_n$—R$^5$, —C(O)—NR$^5$R$^6$, and cyano;
R$^5$ and R$^6$ are independently selected from the group consisting of hydrogen, C$_1$-C$_6$ straight alkyl, C$_1$-C$_6$ branched alkyl, C$_2$-C$_6$ alkenyl, C$_3$-C$_6$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^7$R$^8$, oxo, cyano, carboxy, carboxyalkyl, alkoxycarbonyl, —OR$^9$, —C(O)R$^9$, —C(O)—NH$_2$, —C(O)—N(H)R$^7$, —C(O)—NR$^7$R$^8$, —NR$^7$C(O)R$^9$, —NR$^9$C(O)OR$^9$, —S(O)$_n$—R$^9$, —S(O)$_2$—NH$_2$, —S(O)$_2$—N(H)R$^7$ and —S(O)$_2$—NR$^7$R$^8$; and R$^5$ and R$^6$ taken together may form a 4- to 12-membered monocyclic, bicyclic, tricyclic or benzofused ring;
R$^7$ and R$^8$ are independently selected from the group consisting of alkyl, alkenyl and aryl and taken together may form a 4- to 12-membered monocyclic, bicyclic, tricyclic or benzofused ring; and $R^9$ is independently selected from the group consisting of $C_1$-$C_6$ straight alkyl, $C_1$-$C_6$ branched alkyl, $C_2$-$C_6$ alkenyl, $C_3$-$C_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In one embodiment of Formula II, m is 0.

In one embodiment, $R^1$ is heteroaryl. In another embodiment, $R^1$ is heterocyclic.

In another principal embodiment, compounds, pharmaceutical compositions and methods of treatment or prophylaxis of an inflammatory condition, and in particular asthma, comprising administering to a host in need thereof a compound of Formula III, or a pharmaceutically acceptable salt, ester, prodrug or derivative thereof are provided:

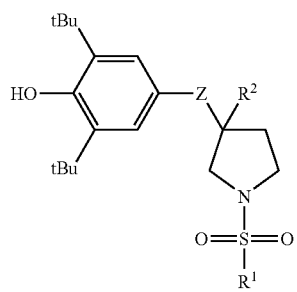

(III)

wherein:

Z is selected from $S(O)_m$ or $Se(O)_m$;

m is 0, 1 or 2;

$R^1$ is heteroaryl or heterocyclic, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$NR^6C(O)OR^5$—, —$OC(O)NR^5R^6$, —$S(O)_n$—$R^5$, —$S(O)_2$—$NH_2$, —$S(O)_n$—$N(H)R^5$ and —$S(O)_2$—$NR^5R^6$;

n is 0, 1 or 2;

$R^2$ is selected from the group consisting of hydrogen, $C_1$-$C_6$ straight alkyl, and $C_1$-$C_6$ branched alkyl, wherein all may be optionally substituted by one or more selected from the group consisting of hydroxy, heterocyclic, heteroaryl, carboxy, alkoxycarbonyl, —$NR^5R^6$, —$NR^6C(O)R^5$, —$NR^6C(O)NR^5R^6$, —$NR^6C(O)OR^5$, —$OC(O)NR^5R^6$, —$OR^5$, —$C(O)R^5$, —$S(O)_n$—$R^5$, —$C(O)$—$NR^5R^6$, and cyano;

$R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_6$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$; and $R^5$ and $R^6$ taken together may form a 4- to 12-membered monocyclic, bicyclic, tricyclic or benzofused ring.

$R^7$ and $R^8$ are independently selected from the group consisting of alkyl, alkenyl and aryl and taken together may form a 4- to 12-membered monocyclic, bicyclic, tricyclic or benzofused ring; and $R^9$ is independently selected from the group consisting of $C_1$-$C_6$ straight alkyl, $C_1$-$C_6$ branched alkyl, $C_2$-$C_6$ alkenyl, $C_3$-$C_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In one embodiment, $R^1$ is heteroaryl. In another embodiment, $R^1$ is heterocyclic.

In some embodiments, Z is $S(O)_m$ and m is 0. In other embodiments, Z is $S(O)_m$ and m is 1. In some embodiments, Z is $S(O)_m$ and m is 2. In yet other embodiments, Z is $Se(O)_m$ and m is 0. In certain embodiments, Z is $Se(O)_m$ and m is 1. In certain embodiments, Z is $Se(O)_m$ and m is 2.

In specific subembodiments, $R^1$ is a nitrogen-containing heteroaryl or heterocyclic. In certain embodiments, $R^1$ contains one nitrogen. In other embodiments, $R^1$ contains two or more nitrogen atoms. In certain embodiments, $R^1$ contains one nitrogen and one or more other heteroatoms. In certain embodiments, $R^1$ contains one nitrogen and one sulfur. In certain embodiments, $R^1$ contains one oxygen.

In specific subembodiments, $R^1$ is a oxygen-containing heteroaryl. In certain embodiments, $R^1$ contains one oxygen. In other embodiments, $R^1$ contains two or more oxygen atoms.

In specific subembodiments, $R^1$ is a sulfur-containing heteroaryl. In certain embodiments, $R^1$ contains one sulfur. In other embodiments, $R^1$ contains two or more sulfur atoms.

In some embodiments, $R^1$ is substituted with a substituent selected from alkyl, hydroxyalkyl, carboxy or carboxyalkyl. In specific embodiments, $R^1$ is substituted with —COOH, —$CH_2OH$, —$C(CH_3)_2OH$, —$CH(CH_3)OH$.

In specific embodiments, the compound is in the form of an amine salt.

In specific embodiments, the compound is in the form of an arginine salt. In specific embodiments, the compound is in the form of a meglumine salt. In specific embodiments, the compound is in the form of a tris(hydroxymethyl)aminomethane (THAM) salt.

In one embodiment, the compounds are administered for the treatment or prophylaxis of an inflammatory disorder. In certain embodiments, the inflammatory disorder is a respiratory disorder. In particular embodiments, the inflammatory disorder is asthma or COPD. In other embodiments the inflammatory disorder is a cardiovascular disorder. Cardiovascular inflammatory disorders include atherosclerosis, post-angioplasty, restenosis, coronary artery diseases, angina, and other cardiovascular diseases. In certain embodiments, the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat inflammatory conditions that are mediated by mononuclear leucocytes. In an alternative embodiment, the compounds can be administered to treat small vessel disease that is not treatable by surgery or angioplasty, or other vessel disease in which surgery is not an option. The compounds can also be used to stabilize patients prior to revascularization therapy.

DETAILED DESCRIPTION OF THE INVENTION

It has been discovered that compounds of Formula (I) inhibit the expression of certain inflammatory cytokines and can be used to treat an inflammatory disease in a patient. Inflammatory disorders include, but are not limited to asthma, atherosclerosis, post-angioplasty, restenosis, coronary artery diseases, angina, as well as other cardiovascular and noncardiovascular inflammatory diseases such as rheumatoid and osteoarthritis, dermatitis, psoriasis, cystic fibrosis, post transplantation late and chronic solid organ rejection, eczematous dermatitis, Kaposi's sarcoma, multiple sclerosis, or proliferative disorders of smooth muscle cells.

Compounds

In one embodiment, compounds, pharmaceutical compositions and methods of treatment or prophylaxis of an inflammatory condition, and in particular asthma, comprising administering to a host in need thereof a compound of Formula I, or a pharmaceutically acceptable salt, ester, prodrug or derivative thereof are provided:

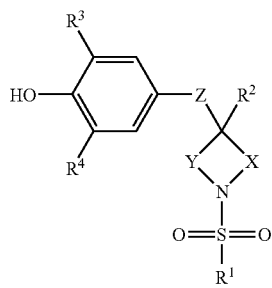

(I)

wherein:

X and Y are independently selected from —$CH_2$— or —$CH_2$—$CH_2$—;

Z is selected from $S(O)_m$ or $Se(O)_m$;

m is 0, 1 or 2;

$R^1$ is heteroaryl, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$OC(O)NR^5R^6$, —$NR^6C(O)OR^5$, —$S(O)_n$—$R^5$, —$S(O)_2$—$NH_2$, —$S(O)_n$—$N(H)R^5$ and —$S(O)_2$—$NR^5R^6$;

n is 0, 1 or 2;

$R^2$ is selected from the group consisting of hydrogen, $C_1$-$C_6$ straight alkyl, and $C_1$-$C_6$ branched alkyl, wherein all may be optionally substituted by one or more selected from the group consisting of halo, hydroxy, heterocyclic, heteroaryl, carboxy, —$NR^5R^6$, alkoxycarbonyl, —$NR^6C(O)R^5$, —$NR^6C(O)NR^5R^6$, —$NR^6C(O)OR^5$, —$OC(O)NR^5R^6$, —$OR^5$, —$C(O)R^5$, —$S(O)_n$—$R^5$, —$C(O)$—$NR^5R^6$, and cyano;

$R^3$ and $R^4$ are independently selected from the group consisting of $C_1$-$C_6$ straight alkyl, $C_1$-$C_6$ branched alkyl, and $C_3$-$C_8$ cyclic alkyl;

$R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$; and $R^5$ and $R^6$ taken together may form a 4- to 12-membered monocyclic, bicyclic, tricyclic or benzofused ring;

$R^7$ and $R^8$ are independently selected from the group consisting of alkyl, alkenyl and aryl and taken together may form a 4- to 12-membered monocyclic, bicyclic, tricyclic or benzofused ring; and $R^9$ is independently selected from the group consisting of $C_1$-$C_6$ straight alkyl, $C_1$-$C_6$ branched alkyl, $C_2$-$C_6$ alkenyl, $C_3$-$C_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In one embodiment, $R^3$ and $R^4$ are tert-butyl.

In certain embodiments, Z is $S(O)_m$ and m is 0. In other embodiments, Z is $S(O)_m$ and m is 1. In some embodiments, Z is $S(O)_m$ and m is 2. In other embodiments, Z is $Se(O)_m$ and m is 0. In other embodiments, Z is $Se(O)_m$ and m is 1. In some embodiments, Z is $Se(O)_m$ and m is 2.

In certain embodiments, $R^1$ is heteroaryl, substituted with one substituent. In other embodiments, $R^1$ is heteroaryl substituted with more than one substituent. In particular embodiments, substituents on $R^1$ are selected from alkyl, hydroxyalkyl, carboxy and carboxyalkyl.

In one subembodiment, $R^1$ is substituted or unsubstituted N-methylpyrrolyl. In a particular subembodiment, $R^1$ is N-methylpyrrolyl optionally substituted with one or more substituents independently selected from the group consisting of hydroxyalkyl, carboxy, carboxyalkyl. In certain subembodiments, $R_1$ is N-methylpyrrolyl optionally substituted with one or more substituents independently selected from the group consisting of hydroxymethyl and carboxy.

In some embodiments, $R^2$ is selected from the group consisting of hydrogen, $C_{1-6}$ straight chained or branched alkyl, optionally substituted by one or more substituents selected from the group consisting of halo, hydroxy, cyano, heteroaryl, carboxy, —$NR^5R^6$, alkoxycarbonyl, —$OR^5$ and —$C(O)R^5$. In some subembodiments, $R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$. In other subembodiments, $R^5$ and $R^6$ taken together form a 4- to 12-membered monocyclic, bicyclic, tricyclic or benzofused ring. In certain embodiments, $R^2$ is substituted with one or more substituents selected from cycloalkyl, acyl, hydroxy, hydroxyalkyl, heterocyclic, heteroaryl and aryl.

In another principal embodiment, compounds, pharmaceutical compositions and methods of treatment or prophylaxis of an inflammatory condition, and in particular asthma, comprising administering to a host in need thereof a compound of Formula II, or a pharmaceutically acceptable salt, ester, prodrug or derivative thereof are provided:

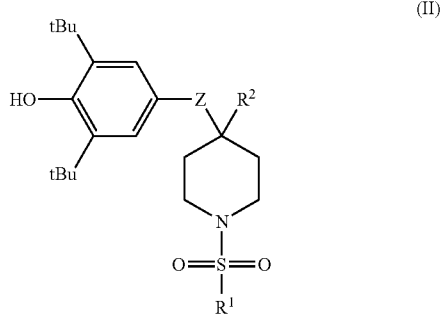

(II)

wherein:

$Z$ is selected from $S(O)_m$ or $Se(O)_m$;

m is 0, 1 or 2;

$R^1$ is heteroaryl, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$NR^6C(O)OR^5$, —$OC(O)NR^5R^6$, —$S(O)_n$—$R^5$, —$S(O)_2$—$NH_2$, —$S(O)_n$—$N(H)R^5$ and —$S(O)_2$—$NR^5R^6$;

n is 0, 1 or 2;

$R^2$ is selected from the group consisting of hydrogen, $C_1$-$C_6$ straight alkyl, and $C_1$-$C_6$ branched alkyl, wherein all may be optionally substituted by one or more selected from the group consisting of halo, hydroxy, heterocyclic, heteroaryl, carboxy, alkoxycarbonyl, —$NR^5R^6$, —$NR^6C(O)R^5$, —$NR^6C(O)NR^5R^6$, —$NR^6C(O)OR^5$, —$OC(O)NR^5R^6$, —$OR^5$, —$C(O)R^5$, —$S(O)_n$—$R^5$, —$C(O)$—$NR^5R^6$, and cyano;

$R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_6$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$; and $R^5$ and $R^6$ taken together may form a 4- to 12-membered monocyclic, bicyclic, tricyclic or benzofused ring;

$R^7$ and $R^8$ are independently selected from the group consisting of alkyl, alkenyl and aryl and taken together may form a 4- to 12-membered monocyclic, bicyclic, tricyclic or benzofused ring; and $R^9$ is independently selected from the group consisting of $C_1$-$C_6$ straight alkyl, $C_1$-$C_6$ branched alkyl, $C_2$-$C_6$ alkenyl, $C_3$-$C_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In some embodiments, Z is $S(O)_m$ and m is 0. In other embodiments, Z is $S(O)_m$ and m is 1. In yet other embodiments, Z is $Se(O)_m$ and m is 0. In certain embodiments, Z is $Se(O)_m$ and m is 1.

In certain embodiments, $R^2$ is selected from the group consisting of hydrogen, $C_{1-6}$ straight chained or branched alkyl, optionally substituted by one or more substituents selected from the group consisting of halo, hydroxy, cyano, heteroaryl, carboxy, —$NR^5R^6$, alkoxycarbonyl, —$OR^5$ and —$C(O)R^5$. In some subembodiments, $R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$.
In other embodiments, $R^5$ and $R^6$ taken together form a 4- to 12-membered monocyclic, bicyclic, tricyclic or benzofused ring. In some embodiments, $R^2$ is substituted with one or more substituents selected from cycloalkyl, acyl, hydroxy, hydroxyalkyl, heterocyclic, heteroaryl and aryl.

In certain embodiments, $R^2$ is hydrogen or $C_1$-$C_4$ straight or branched alkyl, wherein the $C_1$-$C_4$ alkyl is substituted by one or more hydroxy, cyano and heteroaryl. In some embodiments, $R^2$ is hydrogen. In other embodiments, $R^2$ is unsubstituted $C_1$-$C_4$ straight or branched alkyl. In yet other embodiments, $R^2$ is $C_1$-$C_4$ straight-chain alkyl, optionally substituted by one or more hydroxy, cyano and heteroaryl. $R^2$ may also be $C_1$-$C_4$ branched alkyl, optionally substituted by one or more hydroxy, cyano and heteroaryl. In particular embodiments, $R^2$ is selected from the group consisting of hydrogen, cyanomethyl, tetrazolylmethyl, imidazolylethyl, hydroxymethyl, 2-methyl-2-hydroxypropyl, and hydroxyethyl. In more particular embodiments, $R^2$ is selected from the group consisting of hydrogen, hydroxymethyl, 2-methyl-2-hydroxypropyl, and hydroxyethyl.

In certain embodiments, $R^1$ is unsubstituted heteroaryl. In other embodiments, $R^1$ is heteroaryl, substituted with one substituent. In yet other embodiments, $R^1$ is heteroaryl substituted with more than one substituent. In particular embodiments, substituents on $R^1$ are selected from alkyl, hydroxyalkyl, carboxy and carboxyalkyl. In more particular embodiments, $R^1$ is selected from the group consisting of furyl, thienyl, thiazolyl, pyrazolyl, pyrrolyl, triazolyl, tetrazolyl, oxazolyl, imidazolyl, isooxazolyl, isothiazolyl, pyridyl, pyridazinyl, pyrimidinyl, pyrazinyl, thiazinyl, benzimidazolyl, tetrahydrobenzimidazolyl, benzofuryl, benzothienyl, benzothiazolyl, benzopyrazolyl, indolyl, benzotriazolyl, benzoxazolyl, benzoisoxazolyl, benzoisothiazolyl, benzopyridyl, benzopyridazinyl, benzopyrimidinyl, benzopyrazinyl, and benzothiazinyl, wherein all may be substituted by one or more substituents independently selected from the group consisting of fluoro, chloro, bromo, iodo, trifluoromethyl, methyl, ethyl, iso-propyl, tert-butyl, hydroxymethyl, 2-methyl-2-hydroxyethyl, amino, and carboxy. In more particular embodiments, $R^1$ is selected from the group consisting of furyl, thienyl, thiazolyl, pyrazolyl, pyrrolyl and imidazolyl, wherein all may be substituted by one or more substituents independently selected from the group consisting of fluoro, chloro, trifluoromethyl, methyl, hydroxymethyl, 2-methyl-2-hydroxyethyl, amino, and carboxy. In even more particular embodiments, $R^1$ is pyrrolyl or imidazolyl, wherein all may be substituted by one or more substituents independently selected from the group consisting of methyl, hydroxymethyl, 2-methyl-2-hydroxyethyl, and carboxy.

In a particular subembodiment, $R^1$ is selected from the group consisting of furyl, thienyl, thiazolyl, pyrazolyl, pyrrolyl, benzimidazolyl and imidazolyl, wherein all may be substituted by one or more substituents independently selected from the group consisting of fluoro, chloro, bromo, iodo, trifluoromethyl, methyl, ethyl, iso-propyl, tert-butyl, hydroxymethyl, 2-methyl-2-hydroxyethyl, amino, and carboxy and $R^2$ is selected from the group consisting of hydrogen, cyanomethyl, tetrazolylmethyl, imidazolylethyl, hydroxymethyl, 2-methyl-2-hydroxypropyl, and hydroxyethyl.

In a more particular subembodiment, $R^1$ is selected from the group consisting of furyl, thienyl, thiazolyl, pyrazolyl, pyrrolyl and imidazolyl, wherein all may be substituted by one or more substituents independently selected from the group consisting of fluoro, chloro, trifluoromethyl, methyl, hydroxymethyl, 2-methyl-2-hydroxyethyl, amino, and carboxy and $R^2$ is selected from the group consisting of hydrogen, hydroxymethyl, 2-methyl-2-hydroxypropyl, and hydroxyethyl.

In another subembodiment, $R^1$ is pyrrolyl or imidazolyl, wherein all may be substituted by one or more substituents independently selected from the group consisting of methyl, hydroxymethyl, 2-methyl-2-hydroxyethyl, and carboxy; and $R^2$ is selected from the group consisting of hydrogen, hydroxymethyl, 2-methyl-2-hydroxypropyl, and hydroxyethyl.

In one subembodiment, $R^1$ is substituted or unsubstituted N-methylpyrrolyl. In a particular subembodiment, $R^1$ is N-methylpyrrolyl optionally substituted with one or more substituents independently selected from the group consisting of hydroxyalkyl, carboxy, carboxyalkyl. In certain subembodiments, $R^1$ is N-methylpyrrolyl optionally substituted with one or more substituents independently selected from the group consisting of hydroxymethyl and carboxy.

In another principal embodiment, compounds, pharmaceutical compositions and methods of treatment or prophylaxis of an inflammatory condition, and in particular asthma, comprising administering to a host in need thereof a compound of Formula III, or a pharmaceutically acceptable salt, ester, prodrug or derivative thereof are provided:

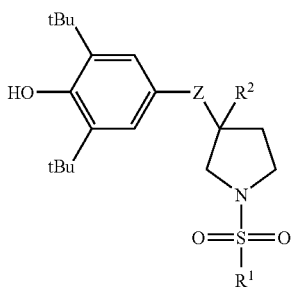

(III)

wherein:
Z is selected from $S(O)_m$ or $Se(O)_m$;
m is 0, 1 or 2;
$R^1$ is heteroaryl, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$NR^6C(O)OR^5$, —$OC(O)NR^5R^6$, —$S(O)_n$—$R^5$, —$S(O)_2$—$NH_2$, —$S(O)_n$—$N(H)R^5$ and —$S(O)_2$—$NR^5R^6$;

n is 0, 1 or 2;

$R^2$ is selected from the group consisting of hydrogen, $C_1$-$C_6$ straight alkyl, and $C_1$-$C_6$ branched alkyl, wherein all may be optionally substituted by one or more selected from the group consisting of hydroxy, heterocyclic, heteroaryl, carboxy, alkoxycarbonyl, —$NR^5R^6$, —$NR^6C(O)R^5$, —$NR^6C(O)NR^5R^6$, —$NR^6C(O)OR^5$, —$OC(O)NR^5R^6$, —$OR^5$, —$C(O)R^5$, —$S(O)_n$—$R^5$, —$C(O)$—$NR^5R^6$, and cyano;

$R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_6$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$; and $R^5$ and $R^6$ taken together may form a 4- to 12-membered monocyclic, bicyclic, tricyclic or benzofused ring.

$R^7$ and $R^8$ are independently selected from the group consisting of alkyl, alkenyl and aryl and taken together may form a 4- to 12-membered monocyclic, bicyclic, tricyclic or benzofused ring; and $R^9$ is independently selected from the group consisting of $C_1$-$C_6$ straight alkyl, $C_1$-$C_6$ branched alkyl, $C_2$-$C_6$ alkenyl, $C_3$-$C_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

In some embodiments, Z is $S(O)_m$ and m is 0. In other embodiments, Z is $S(O)_m$ and m is 1. In yet other embodiments, Z is $Se(O)_m$ and m is 0. In certain embodiments, Z is $Se(O)_m$ and m is 1.

In certain embodiments, $R^2$ is selected from the group consisting of hydrogen, $C_{1-6}$ straight chained or branched alkyl, optionally substituted by one or more substituents selected from the group consisting of halo, hydroxy, cyano, heteroaryl, carboxy, —$NR^5R^6$, alkoxycarbonyl, —$OR^5$ and —$C(O)R^5$. In some subembodiments, $R^5$ and $R^6$ are independently selected from the group consisting of hydrogen, $C_1$-$C_6$ straight alkyl, $C_1$-$C_6$ branched alkyl, $C_2$-$C_6$ alkenyl, $C_3$-$C_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —$NR^7R^8$, oxo, cyano, carboxy, carboxyalkyl, alkoxycarbonyl, —$OR^9$, —$C(O)R^9$, —$C(O)$—$NH_2$, —$C(O)$—$N(H)R^7$, —$C(O)$—$NR^7R^8$, —$NR^7C(O)R^9$, —$NR^7C(O)OR^9$, —$S(O)_n$—$R^9$, —$S(O)_2$—$NH_2$, —$S(O)_2$—$N(H)R^7$ and —$S(O)_2$—$NR^7R^8$. In other embodiments, $R^5$ and $R^6$ taken together form a 4- to 12-membered monocyclic, bicyclic, tricyclic or benzofused ring. In some embodiments, $R^2$ is substituted with one or more substituents selected from cycloalkyl, acyl, hydroxy, hydroxyalkyl, heterocyclic, heteroaryl and aryl.

In certain embodiments, $R^2$ is hydrogen or $C_1$-$C_4$ straight or branched alkyl, wherein the $C_1$-$C_4$ alkyl is substituted by one or more hydroxy, cyano and heteroaryl. In some embodiments, $R^2$ is hydrogen. In other embodiments, $R^2$ is unsubstituted $C_1$-$C_4$ straight or branched alkyl. In yet other embodiments, $R^2$ is $C_1$-$C_4$ straight chain alkyl, optionally substituted by one or more hydroxy, cyano and heteroaryl. $R^2$ may also be $C_1$-$C_4$ branched alkyl, optionally substituted by one or more hydroxy, cyano and heteroaryl. In particular embodiments, $R^2$ is selected from the group consisting of hydrogen, cyanomethyl, tetrazolylmethyl, imidazolylethyl, hydroxymethyl, 2-methyl-2-hydroxypropyl, and hydroxyethyl. In more particular embodiments, $R^2$ is selected from the group consisting of hydrogen, hydroxymethyl, 2-methyl-2-hydroxypropyl, and hydroxyethyl.

In certain embodiment, $R^1$ is heteroaryl, substituted with one substituent. In other embodiments, $R^1$ is heteroaryl substituted with more than one substituent. In particular embodiments, substituents on $R^1$ are selected from alkyl, hydroxyalkyl, carboxy and carboxyalkyl. In certain embodiments, $R^1$ is a substituted or unsubstituted 5-membered heteroaromatic ring. In certain embodiments, $R^1$ is a substituted or unsubstituted 6-membered heteroaromatic ring. In more particular embodiments, $R^1$ is selected from the group consisting of furyl, thienyl, thiazolyl, pyrazolyl, pyrrolyl, benzimidazolyl and imidazolyl, wherein all may be substituted by one or more substituents independently selected from the group consisting of fluoro, chloro, bromo, iodo, trifluoromethyl, methyl, ethyl, iso-propyl, tert-butyl, hydroxymethyl, 2-methyl-2-hydroxyethyl, amino, and carboxy. In more particular embodiments, $R^1$ is selected from the group consisting of furyl, thienyl, thiazolyl, pyrazolyl, pyrrolyl and imidazolyl, wherein all may be substituted by one or more substituents independently selected from the group consisting of fluoro, chloro, trifluoromethyl, methyl, hydroxymethyl, 2-methyl-2-hydroxyethyl, amino, and carboxy. In even more particular embodiments, $R^1$ is pyrrolyl or imidazolyl, wherein all may be substituted by one or more substituents independently selected from the group consisting of methyl, hydroxymethyl, 2-methyl-2-hydroxyethyl, and carboxy.

In a particular subembodiment, $R^1$ is selected from the group consisting of furyl, thienyl, thiazolyl, pyrazolyl, pyrrolyl, benzimidazolyl and imidazolyl, wherein all may be substituted by one or more substituents independently selected from the group consisting of fluoro, chloro, bromo, iodo, trifluoromethyl, methyl, ethyl, iso-propyl, tert-butyl, hydroxymethyl, 2-methyl-2-hydroxyethyl, amino, and carboxy and $R^2$ is selected from the group consisting of hydrogen, cyanomethyl, tetrazolylmethyl, imidazolylethyl, hydroxymethyl, 2-methyl-2-hydroxypropyl, and hydroxyethyl.

In a more particular subembodiment, $R^1$ is selected from the group consisting of furyl, thienyl, thiazolyl, pyrazolyl, pyrrolyl and imidazolyl, wherein all may be substituted by one or more substituents independently selected from the group consisting of fluoro, chloro, trifluoromethyl, methyl, hydroxymethyl, 2-methyl-2-hydroxyethyl, amino, and carboxy and $R^2$ is selected from the group consisting of hydrogen, hydroxymethyl, 2-methyl-2-hydroxypropyl, and hydroxyethyl.

In another subembodiment, $R^1$ is pyrrolyl or imidazolyl, wherein all may be substituted by one or more substituents independently selected from the group consisting of methyl, hydroxymethyl, 2-methyl-2-hydroxyethyl, and carboxy; and $R^2$ is selected from the group consisting of hydrogen, hydroxymethyl, 2-methyl-2-hydroxypropyl, and hydroxyethyl.

In some embodiments, compounds of the invention are as defined below in Table A:

TABLE A

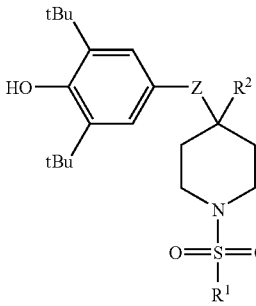

wherein:

| Ex. No. | $R^1$ | $R^2$ | Z |
|---|---|---|---|
| 24. | 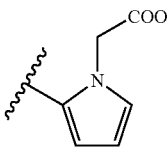 | H | S |
| 25. | 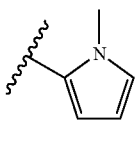 | H | S |
| 26. | 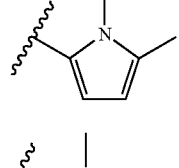 | H | S |
| 27. | 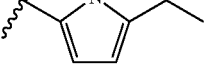 | H | S |
| 28. | 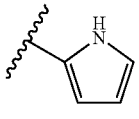 | H | S |
| 29. | 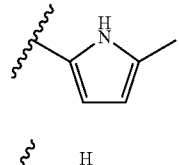 | H | S |
| 30. | 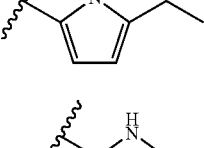 | H | S |
| 31. | 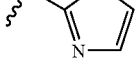 | H | S |

TABLE A-continued

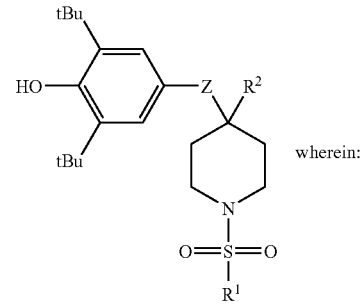

wherein:

| Ex. No. | R¹ | R² | Z |
|---|---|---|---|
| 32. | 2-(5-methyl-1H-imidazolyl) | H | S |
| 33. | 2-(5-ethyl-1H-imidazolyl) | H | S |
| 34. | 2-(1-methylimidazolyl) | H | S |
| 35. | 2-(1,5-dimethylimidazolyl) | H | S |
| 36. | 2-(5-ethyl-1-methylimidazolyl) | H | S |
| 37. | 5-(1H-imidazolyl) | H | S |
| 38. | 5-(2-methyl-1H-imidazolyl) | H | S |
| 39. | 5-(2-ethyl-1H-imidazolyl) | H | S |
| 40. | 2-(1-methylimidazolyl) | CH₂C(CH₃)₂OH | S |

TABLE A-continued

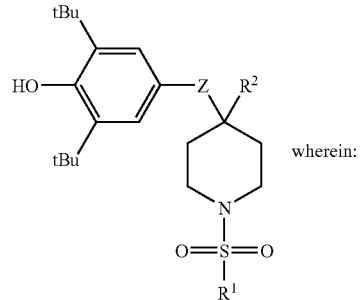

wherein:

| Ex. No. | R¹ | R² | Z |
|---|---|---|---|
| 41. | 2-(1-ethylimidazolyl) | CH₂C(CH₃)₂OH | S |
| 42. | 2-(1-isopropylimidazolyl) | CH₂C(CH₃)₂OH | S |
| 43. | 2-(1H-benzimidazolyl) | CH₂C(CH₃)₂OH | S |
| 44. | 5-(1H-imidazolyl) | CH₂C(CH₃)₂OH | S |
| 45. | 5-(2-methyl-1H-imidazolyl) | CH₂C(CH₃)₂OH | S |
| 46. | 5-(2-trifluoromethyl-1H-imidazolyl) | CH₂C(CH₃)₂OH | S |
| 47. | 5-(2-ethyl-1H-imidazolyl) | CH₂C(CH₃)₂OH | S |
| 48. | 5-(2-isopropyl-1H-imidazolyl) | CH₂C(CH₃)₂OH | S |
| 49. | 5-(2-tert-butyl-1H-imidazolyl) | CH₂C(CH₃)₂OH | S |

TABLE A-continued

Structure: 3,5-di-tBu-4-HO-phenyl–Z–C(R²)(piperidine-N-SO₂-R¹), wherein:

| Ex. No. | R¹ | R² | Z |
|---|---|---|---|
| 50. | 1H-pyrrole-2-carboxylic acid (5-yl) | CH₂C(CH₃)₂OH | S |
| 51. | 1-methyl-pyrrole-2-carboxylic acid (5-yl) | CH₂C(CH₃)₂OH | S |
| 52. | 1H-imidazole-4-carboxylic acid (2-yl) | CH₂C(CH₃)₂OH | S |
| 53. | 1-methyl-imidazole-4-carboxylic acid (2-yl) | CH₂C(CH₃)₂OH | S |
| 54. | 1H-pyrazole-3-carboxylic acid (5-yl) | CH₂C(CH₃)₂OH | S |
| 55. | 1-methyl-pyrazole-3-carboxylic acid (5-yl) | CH₂C(CH₃)₂OH | S |
| 56. | 1H-pyrrole-2-yl-methanol (5-yl) | CH₂C(CH₃)₂OH | S |
| 57. | 1-methyl-pyrrole-2-yl-methanol (5-yl) | CH₂C(CH₃)₂OH | S |
| 58. | 1H-imidazole-4-yl-methanol (2-yl) | CH₂C(CH₃)₂OH | S |
| 59. | 1-methyl-imidazole-5-yl-methanol (2-yl) | CH₂C(CH₃)₂OH | S |
| 60. | 1H-pyrazole-5-yl-methanol (3-yl) | CH₂C(CH₃)₂OH | S |
| 61. | 1-methyl-pyrazole-5-yl-methanol (3-yl) | CH₂C(CH₃)₂OH | S |
| 62. | 1H-pyrrole-2-carboxylic acid (5-yl) | CH₂CH₂OC(CH₃)₃ | S |
| 63. | 1-methyl-pyrrole-2-carboxylic acid (5-yl) | CH₂CH₂OC(CH₃)₃ | S |
| 64. | 1H-imidazole-4-carboxylic acid (2-yl) | CH₂CH₂OC(CH₃)₃ | S |
| 65. | 1-methyl-imidazole-4-carboxylic acid (2-yl) | CH₂CH₂OC(CH₃)₃ | S |
| 66. | 1H-pyrazole-3-carboxylic acid (5-yl) | CH₂CH₂OC(CH₃)₃ | S |
| 67. | 1-methyl-pyrazole-3-carboxylic acid (5-yl) | CH₂CH₂OC(CH₃)₃ | S |

TABLE A-continued (structure with tBu, HO, tBu on phenol ring connected via Z to piperidine with R² substituent, N-sulfonyl with R¹) wherein:

| Ex. No. | R¹ | R² | Z |
|---|---|---|---|
| 68. | 5-(hydroxymethyl)-1H-pyrrol-2-yl | 3-(tert-butoxy)propyl | S |
| 69. | 5-(hydroxymethyl)-1-methyl-pyrrol-2-yl | 3-(tert-butoxy)propyl | S |
| 70. | 4-(hydroxymethyl)-1H-imidazol-2-yl | 3-(tert-butoxy)propyl | S |
| 71. | 5-(hydroxymethyl)-1-methyl-imidazol-2-yl | 3-(tert-butoxy)propyl | S |
| 72. | 5-(hydroxymethyl)-1H-pyrazol-3-yl | 3-(tert-butoxy)propyl | S |
| 73. | 5-(hydroxymethyl)-1-methyl-pyrazol-3-yl | 3-(tert-butoxy)propyl | S |
| 74. | 5-carboxy-1H-pyrrol-2-yl | 3-(imidazol-1-yl)propyl | S |
| 75. | 5-carboxy-1-methyl-pyrrol-2-yl | 3-(imidazol-1-yl)propyl | S |
| 76. | 4-carboxy-1H-imidazol-2-yl | 3-(imidazol-1-yl)propyl | S |
| 77. | 5-carboxy-1-methyl-imidazol-2-yl | 3-(imidazol-1-yl)propyl | S |
| 78. | 5-carboxy-1H-pyrazol-3-yl | 3-(imidazol-1-yl)propyl | S |
| 79. | 5-carboxy-1-methyl-pyrazol-3-yl | 3-(imidazol-1-yl)propyl | S |
| 80. | 5-(hydroxymethyl)-1H-pyrrol-2-yl | 3-(imidazol-1-yl)propyl | S |
| 81. | 5-(hydroxymethyl)-1-methyl-pyrrol-2-yl | 3-(imidazol-1-yl)propyl | S |
| 82. | 4-(hydroxymethyl)-1H-imidazol-2-yl | 3-(imidazol-1-yl)propyl | S |
| 83. | 5-(hydroxymethyl)-1-methyl-imidazol-2-yl | 3-(imidazol-1-yl)propyl | S |
| 84. | 5-(hydroxymethyl)-1H-pyrazol-3-yl | 3-(imidazol-1-yl)propyl | S |

TABLE A-continued

Structure: 3,5-di-tBu-4-HO-phenyl–Z–C(R²)(piperidine-N-SO₂-R¹)

| Ex. No. | R¹ | R² | Z |
|---|---|---|---|
| 85. | 5-(1-methyl-1H-pyrazol-3-yl)methanol [attached at pyrazole 5-position; 3-CH₂OH] | 3-(1H-imidazol-1-yl)propyl | S |
| 86. | 1H-pyrrole-2-carboxylic acid (5-yl) | (1H-tetrazol-5-yl)methyl | S |
| 87. | 1-methyl-1H-pyrrole-2-carboxylic acid (5-yl) | (1H-tetrazol-5-yl)methyl | S |
| 88. | 1H-imidazole-4-carboxylic acid (2-yl) | (1H-tetrazol-5-yl)methyl | S |
| 89. | 1-methyl-1H-imidazole-4-carboxylic acid (2-yl) | (1H-tetrazol-5-yl)methyl | S |
| 90. | 1H-pyrazole-3-carboxylic acid (5-yl) | (1H-tetrazol-5-yl)methyl | S |
| 91. | 1-methyl-1H-pyrazole-3-carboxylic acid (5-yl) | (1H-tetrazol-5-yl)methyl | S |
| 92. | (1H-pyrrol-2-yl)methanol (5-yl) | (1H-tetrazol-5-yl)methyl | S |
| 93. | (1-methyl-1H-pyrrol-2-yl)methanol (5-yl) | (1H-tetrazol-5-yl)methyl | S |
| 94. | (1H-imidazol-2-yl)methanol (4/5-yl) | (1H-tetrazol-5-yl)methyl | S |
| 95. | (1-methyl-1H-imidazol-2-yl)methanol (5-yl) | (1H-tetrazol-5-yl)methyl | S |
| 96. | (1H-pyrazol-3-yl)methanol (5-yl) | (1H-tetrazol-5-yl)methyl | S |
| 97. | (1-methyl-1H-pyrazol-3-yl)methanol (5-yl) | (1H-tetrazol-5-yl)methyl | S |
| 98. | 2-(1H-imidazol-2-yl)propan-2-ol (4/5-yl) | 3-methoxypropyl | S |
| 99. | 2-(1H-imidazol-2-yl)propan-2-ol (4/5-yl) | cyanomethyl | S |
| 100. | 2-(1H-imidazol-2-yl)propan-2-ol (4/5-yl) | 3-methoxypropyl | Se |
| 101. | 2-(1H-imidazol-2-yl)propan-2-ol (4/5-yl) | cyanomethyl | Se |

TABLE A-continued

Structure: 3,5-di-tBu-4-HO-phenyl-Z-R² where R² is attached to a 4-substituted piperidine with N-SO₂-R¹

| Ex. No. | R¹ | R² | Z |
|---|---|---|---|
| 102. | 1-methylimidazol-2-yl | -CH₂C(CH₃)₂OH | Se |
| 103. | 1-ethylimidazol-2-yl | -CH₂C(CH₃)₂OH | Se |
| 104. | 1-isopropylimidazol-2-yl | -CH₂C(CH₃)₂OH | Se |
| 105. | 1H-benzimidazol-2-yl | -CH₂C(CH₃)₂OH | Se |
| 106. | 1H-imidazol-4-yl | -CH₂C(CH₃)₂OH | Se |
| 107. | 2-methyl-1H-imidazol-4-yl | -CH₂C(CH₃)₂OH | Se |
| 108. | 2-trifluoromethyl-1H-imidazol-4-yl | -CH₂C(CH₃)₂OH | Se |
| 109. | 2-ethyl-1H-imidazol-4-yl | -CH₂C(CH₃)₂OH | Se |
| 110. | 2-isopropyl-1H-imidazol-4-yl | -CH₂C(CH₃)₂OH | Se |
| 111. | 2-tert-butyl-1H-imidazol-5-yl | -CH₂C(CH₃)₂OH | Se |
| 112. | 5-carboxy-1H-pyrrol-2-yl | -CH₂C(CH₃)₂OH | Se |
| 113. | 5-carboxy-1-methyl-1H-pyrrol-2-yl | -CH₂C(CH₃)₂OH | Se |
| 114. | 4-carboxy-1H-imidazol-2-yl | -CH₂C(CH₃)₂OH | Se |
| 115. | 4-carboxy-1-methyl-1H-imidazol-2-yl | -CH₂C(CH₃)₂OH | Se |
| 116. | 3-carboxy-1H-pyrazol-5-yl | -CH₂C(CH₃)₂OH | Se |
| 117. | 3-carboxy-1-methyl-1H-pyrazol-5-yl | -CH₂C(CH₃)₂OH | Se |
| 118. | 5-(hydroxymethyl)-1H-pyrrol-2-yl | -CH₂C(CH₃)₂OH | Se |
| 119. | 5-(hydroxymethyl)-1-methyl-1H-pyrrol-2-yl | -CH₂C(CH₃)₂OH | Se |

TABLE A-continued

Structure: 3,5-di-tBu-4-HO-phenyl–Z–C(R²)(piperidine-N-SO₂-R¹)

| Ex. No. | R¹ | R² | Z |
|---|---|---|---|
| 120. | 1H-imidazol-2-yl-5-CH₂OH | -CH₂-C(CH₃)₂-OH | Se |
| 121. | 1-methyl-imidazol-2-yl-5-CH₂OH | -CH₂-C(CH₃)₂-OH | Se |
| 122. | 1H-pyrazol-3-yl-5-CH₂OH | -CH₂-C(CH₃)₂-OH | Se |
| 123. | 1-methyl-pyrazol-5-yl-3-CH₂OH | -CH₂-C(CH₃)₂-OH | Se |
| 124. | 1H-pyrrol-2-yl-5-COOH | -CH₂CH₂-O-C(CH₃)₃ | Se |
| 125. | 1-methyl-pyrrol-2-yl-5-COOH | -CH₂CH₂-O-C(CH₃)₃ | Se |
| 126. | 1H-imidazol-2-yl-4-COOH | -CH₂CH₂-O-C(CH₃)₃ | Se |
| 127. | 1-methyl-imidazol-2-yl-4-COOH | -CH₂CH₂-O-C(CH₃)₃ | Se |
| 128. | 1H-pyrazol-3-yl-5-COOH | -CH₂CH₂-O-C(CH₃)₃ | Se |
| 129. | 1-methyl-pyrazol-5-yl-3-COOH | -CH₂CH₂-O-C(CH₃)₃ | Se |
| 130. | 1H-pyrrol-2-yl-5-CH₂OH | -CH₂CH₂-O-C(CH₃)₃ | Se |
| 131. | 1-methyl-pyrrol-2-yl-5-CH₂OH | -CH₂CH₂-O-C(CH₃)₃ | Se |
| 132. | 1H-imidazol-2-yl-4-CH₂OH | -CH₂CH₂-O-C(CH₃)₃ | Se |
| 133. | 1-methyl-imidazol-2-yl-4-CH₂OH | -CH₂CH₂-O-C(CH₃)₃ | Se |
| 134. | 1H-pyrazol-3-yl-5-CH₂OH | -CH₂CH₂-O-C(CH₃)₃ | Se |
| 135. | 1-methyl-pyrazol-5-yl-3-CH₂OH | -CH₂CH₂-O-C(CH₃)₃ | Se |
| 136. | 1H-pyrrol-2-yl-5-COOH | -CH₂CH₂-(imidazol-1-yl) | Se |
| 137. | 1-methyl-pyrrol-2-yl-5-COOH | -CH₂CH₂-(imidazol-1-yl) | Se |

TABLE A-continued

Structure: 3,5-di-tBu-4-HO-phenyl–Z–C(R²)(piperidine-N-SO₂-R¹)

| Ex. No. | R¹ | R² | Z |
|---|---|---|---|
| 138 | 1H-imidazole-4-carboxylic acid (2-yl) | 3-(1H-imidazol-1-yl)propyl | Se |
| 139 | 1-methyl-imidazole-5-carboxylic acid (2-yl) | 3-(1H-imidazol-1-yl)propyl | Se |
| 140 | 1H-pyrazole-3-carboxylic acid (5-yl) | 3-(1H-imidazol-1-yl)propyl | Se |
| 141 | 1-methyl-pyrazole-3-carboxylic acid (5-yl) | 3-(1H-imidazol-1-yl)propyl | Se |
| 142 | 5-(hydroxymethyl)-1H-pyrrol-2-yl | 3-(1H-imidazol-1-yl)propyl | Se |
| 143 | 5-(hydroxymethyl)-1-methyl-pyrrol-2-yl | 3-(1H-imidazol-1-yl)propyl | Se |
| 144 | 5-(hydroxymethyl)-1H-imidazol-2-yl | 3-(1H-imidazol-1-yl)propyl | Se |
| 145 | 5-(hydroxymethyl)-1-methyl-imidazol-2-yl | 3-(1H-imidazol-1-yl)propyl | Se |
| 146 | 5-(hydroxymethyl)-1H-pyrazol-3-yl | 3-(1H-imidazol-1-yl)propyl | Se |
| 147 | 5-(hydroxymethyl)-1-methyl-pyrazol-3-yl | 3-(1H-imidazol-1-yl)propyl | Se |
| 148 | 5-carboxyl-1H-pyrrol-2-yl | (2H-tetrazol-5-yl)methyl | Se |
| 149 | 5-carboxyl-1-methyl-pyrrol-2-yl | (2H-tetrazol-5-yl)methyl | Se |
| 150 | 1H-imidazole-4-carboxylic acid (2-yl) | (2H-tetrazol-5-yl)methyl | Se |
| 151 | 1-methyl-imidazole-5-carboxylic acid (2-yl) | (2H-tetrazol-5-yl)methyl | Se |
| 152 | 1H-pyrazole-3-carboxylic acid (5-yl) | (2H-tetrazol-5-yl)methyl | Se |
| 153 | 1-methyl-pyrazole-3-carboxylic acid (5-yl) | (2H-tetrazol-5-yl)methyl | Se |
| 154 | 5-(hydroxymethyl)-1H-pyrrol-2-yl | (2H-tetrazol-5-yl)methyl | Se |

TABLE A-continued

Structure: 3,5-di-tBu-4-HO-phenyl—Z—C(R²)(piperidine-N-SO₂-R¹)

| Ex. No. | R¹ | R² | Z |
|---|---|---|---|
| 155. | 1-methyl-5-(hydroxymethyl)pyrrol-2-yl | tetrazol-5-ylmethyl | Se |
| 156. | 4-(hydroxymethyl)-1H-imidazol-2-yl | tetrazol-5-ylmethyl | Se |
| 157. | 1-methyl-5-(hydroxymethyl)imidazol-2-yl | tetrazol-5-ylmethyl | Se |
| 158. | 5-(hydroxymethyl)-1H-pyrazol-3-yl | tetrazol-5-ylmethyl | Se |
| 159. | 5-(hydroxymethyl)-1-methylpyrazol-3-yl | tetrazol-5-ylmethyl | Se |
| 160. | 1-(carboxymethyl)pyrrol-2-yl | H | Se |
| 161. | 1-methylpyrrol-2-yl | H | Se |
| 162. | 1,5-dimethylpyrrol-2-yl | H | Se |
| 163. | 5-ethyl-1-methylpyrrol-2-yl | H | Se |
| 164. | 1H-pyrrol-2-yl | H | Se |
| 165. | 5-methyl-1H-pyrrol-2-yl | H | Se |
| 166. | 5-ethyl-1H-pyrrol-2-yl | H | Se |
| 167. | 1H-imidazol-2-yl | H | Se |
| 168. | 4-methyl-1H-imidazol-2-yl | H | Se |
| 169. | 4-ethyl-1H-imidazol-2-yl | H | Se |
| 170. | 1-methylimidazol-2-yl | H | Se |
| 171. | 1,5-dimethylimidazol-2-yl | H | Se |
| 172. | 5-ethyl-1-methylimidazol-2-yl | H | Se |

TABLE A-continued
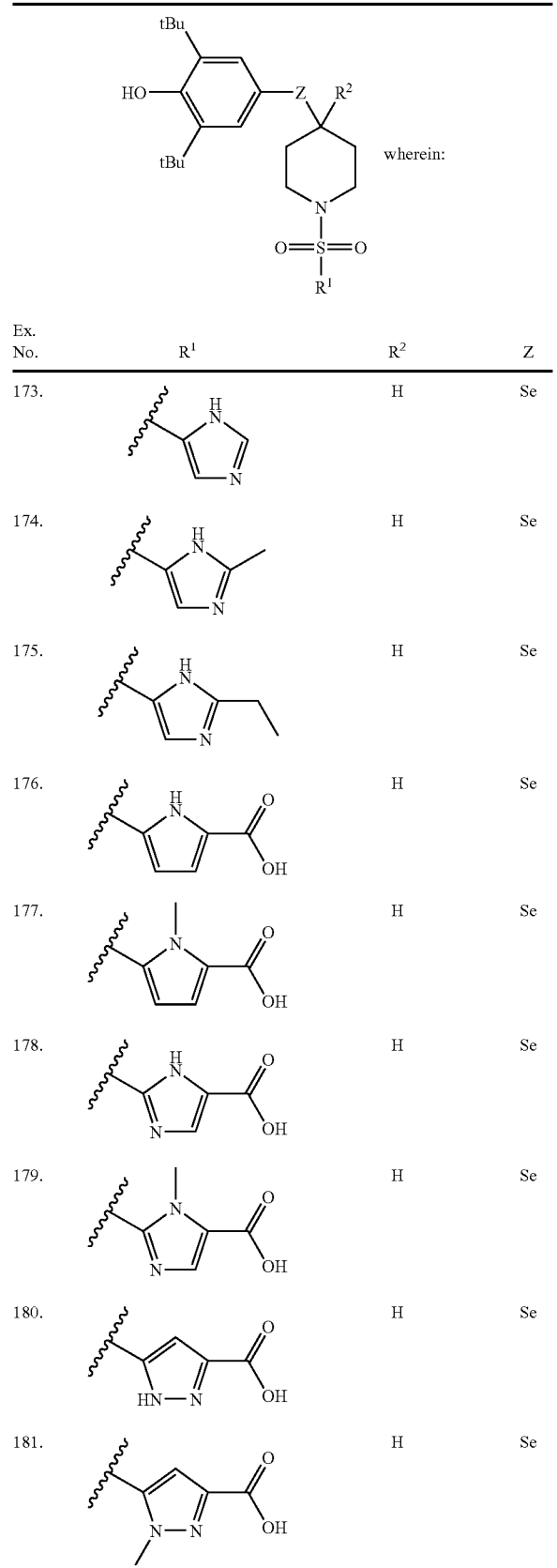
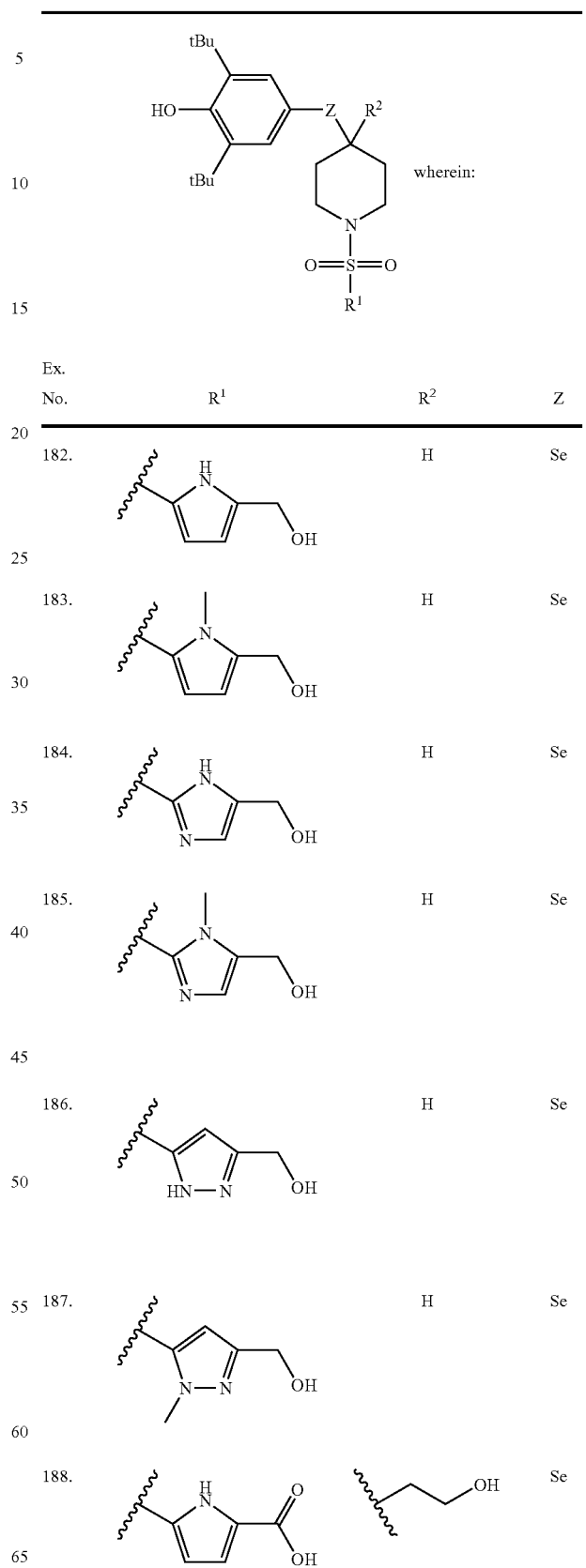

TABLE A-continued

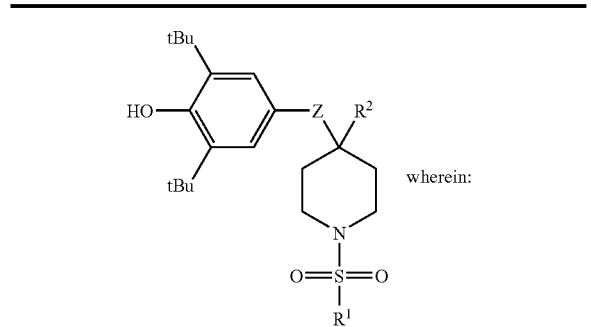

wherein:

| Ex. No. | R¹ | R² | Z |
|---|---|---|---|
| 189. | 1-methyl-pyrrole-2-carboxylic acid | propyl-OH | Se |
| 190. | 1H-imidazole-4-carboxylic acid | propyl-OH | Se |
| 191. | 1-methyl-imidazole-4-carboxylic acid | propyl-OH | Se |
| 192. | 1H-pyrazole-3-carboxylic acid | propyl-OH | Se |
| 193. | 1-methyl-pyrazole-3-carboxylic acid | propyl-OH | Se |
| 194. | 1H-pyrrole-2-methanol | propyl-OH | Se |
| 195. | 1-methyl-pyrrole-2-methanol | propyl-OH | Se |
| 196. | 1H-imidazole-4-methanol | propyl-OH | Se |
| 197. | 1-methyl-imidazole-4-methanol | propyl-OH | Se |
| 198. | 1H-pyrazole-3-methanol | propyl-OH | Se |
| 199. | 1-methyl-pyrazole-3-methanol | propyl-OH | Se |

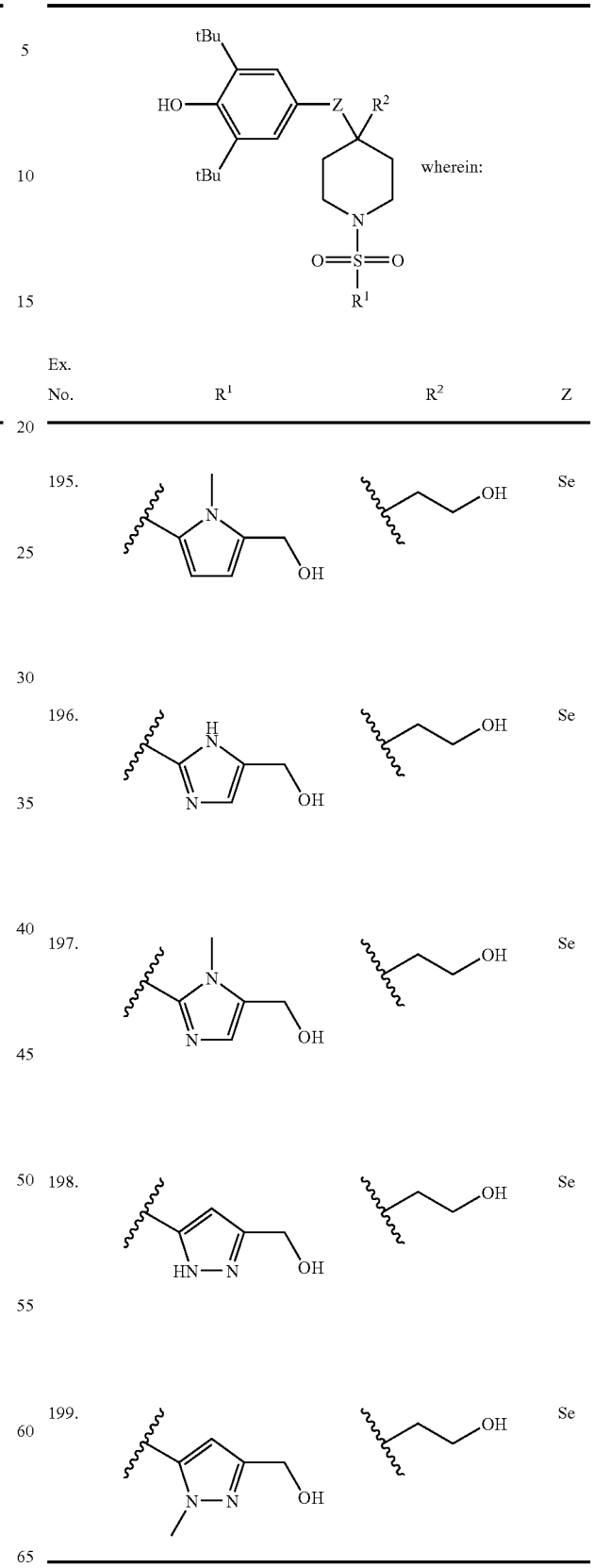

In other embodiments, compounds of the invention are as defined below in Table B:
TABLE B
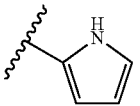
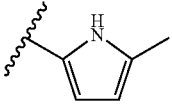, or
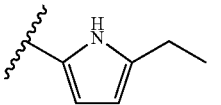 wherein:
| Ex. No. | R¹ | R² | Z |
|---|---|---|---|
| 200. | 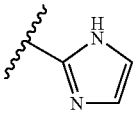 | H | S |
| 201. | | H | S |
| 202. | | H | S |
| 203. | | H | S |
| 204. | | H | S |
| 205. | | H | S |
| 206. | | H | S |
| 207. | | H | S |
| 208. | | H | S |
| 209. | | H | S |
| 210. | | H | S |
| 211. | | H | S |
| 212. | | H | S |
| 213. | | H | S |
| 214. | | H | S |
| 215. | | H | S |

TABLE B-continued

| # | Group 1 | Group 2 | S |
|---|---|---|---|
| 216. | 1-methyl-imidazol-2-yl | 2-methyl-2-hydroxybutyl | S |
| 217. | 1-ethyl-imidazol-2-yl | 2-methyl-2-hydroxybutyl | S |
| 218. | 1-isopropyl-imidazol-2-yl | 2-methyl-2-hydroxybutyl | S |
| 219. | benzimidazol-2-yl | 2-methyl-2-hydroxybutyl | S |
| 220. | 1H-imidazol-4-yl | 2-methyl-2-hydroxybutyl | S |
| 221. | 2-methyl-1H-imidazol-4-yl | 2-methyl-2-hydroxybutyl | S |
| 222. | 2-CF3-1H-imidazol-4-yl | 2-methyl-2-hydroxybutyl | S |
| 223. | 2-ethyl-1H-imidazol-4-yl | 2-methyl-2-hydroxybutyl | S |
| 224. | 2-isopropyl-1H-imidazol-4-yl | 2-methyl-2-hydroxybutyl | S |
| 225. | 2-tert-butyl-1H-imidazol-4-yl | 2-methyl-2-hydroxybutyl | S |
| 226. | 5-carboxy-1H-pyrrol-2-yl | 2-methyl-2-hydroxybutyl | S |
| 227. | 1-methyl-5-carboxy-pyrrol-2-yl | 2-methyl-2-hydroxybutyl | S |
| 228. | 4-carboxy-1H-imidazol-2-yl | 2-methyl-2-hydroxybutyl | S |
| 229. | 1-methyl-5-carboxy-imidazol-2-yl | 2-methyl-2-hydroxybutyl | S |
| 230. | 5-carboxy-1H-pyrazol-3-yl | 2-methyl-2-hydroxybutyl | S |
| 231. | 1-methyl-5-carboxy-pyrazol-3-yl | 2-methyl-2-hydroxybutyl | S |
| 232. | 5-hydroxymethyl-1H-pyrrol-2-yl | 2-methyl-2-hydroxybutyl | S |
| 233. | 1-methyl-5-hydroxymethyl-pyrrol-2-yl | 2-methyl-2-hydroxybutyl | S |
| 234. | 4-hydroxymethyl-1H-imidazol-2-yl | 2-methyl-2-hydroxybutyl | S |
| 235. | 1-methyl-5-hydroxymethyl-imidazol-2-yl | 2-methyl-2-hydroxybutyl | S |
| 236. | 5-hydroxymethyl-1H-pyrazol-3-yl | 2-methyl-2-hydroxybutyl | S |
| 237. | 1-methyl-5-hydroxymethyl-pyrazol-3-yl | 2-methyl-2-hydroxybutyl | S |
| 238. | 5-carboxy-1H-pyrrol-2-yl | 2-(tert-butoxy)ethyl | S |

TABLE B-continued

| # | | | |
|---|---|---|---|
| 239. | 1-methylpyrrole-2-COOH | CH2CH2CH2-O-tBu | S |
| 240. | 1H-imidazole-4-COOH | CH2CH2CH2-O-tBu | S |
| 241. | 1-methylimidazole-5-COOH | CH2CH2CH2-O-tBu | S |
| 242. | 1H-pyrazole-3-COOH | CH2CH2CH2-O-tBu | S |
| 243. | 1-methylpyrazole-3-COOH | CH2CH2CH2-O-tBu | S |
| 244. | 1H-pyrrole-2-CH2OH | CH2CH2CH2-O-tBu | S |
| 245. | 1-methylpyrrole-2-CH2OH | CH2CH2CH2-O-tBu | S |
| 246. | 1H-imidazole-4-CH2OH | CH2CH2CH2-O-tBu | S |
| 247. | 1-methylimidazole-5-CH2OH | CH2CH2CH2-O-tBu | S |
| 248. | 1H-pyrazole-3-CH2OH | CH2CH2CH2-O-tBu | S |
| 249. | 1-methylpyrazole-3-CH2OH | CH2CH2CH2-O-tBu | S |
| 250. | 1H-pyrrole-2-COOH | CH2CH2CH2-imidazole | S |
| 251. | 1-methylpyrrole-2-COOH | CH2CH2CH2-imidazole | S |
| 252. | 1H-imidazole-4-COOH | CH2CH2CH2-imidazole | S |
| 253. | 1-methylimidazole-5-COOH | CH2CH2CH2-imidazole | S |
| 254. | 1H-pyrazole-3-COOH | CH2CH2CH2-imidazole | S |
| 255. | 1-methylpyrazole-3-COOH | CH2CH2CH2-imidazole | S |
| 256. | 1H-pyrrole-2-CH2OH | CH2CH2CH2-imidazole | S |
| 257. | 1-methylpyrrole-2-CH2OH | CH2CH2CH2-imidazole | S |
| 258. | 1H-imidazole-4-CH2OH | CH2CH2CH2-imidazole | S |
| 259. | 1-methylimidazole-5-CH2OH | CH2CH2CH2-imidazole | S |
| 260. | 1H-pyrazole-3-CH2OH | CH2CH2CH2-imidazole | S |

TABLE B-continued

| | | | |
|---|---|---|---|
| 261. | [pyrazole-CH2OH, N-methyl] | [triazole-propyl] | S |
| 262. | [pyrrole-COOH, NH] | [tetrazole-ethyl] | S |
| 263. | [pyrrole-COOH, N-methyl] | [tetrazole-ethyl] | S |
| 264. | [imidazole-COOH, NH] | [tetrazole-ethyl] | S |
| 265. | [imidazole-COOH, N-methyl] | [tetrazole-ethyl] | S |
| 266. | [pyrazole-COOH, NH] | [tetrazole-ethyl] | S |
| 267. | [pyrazole-COOH, N-methyl] | [tetrazole-ethyl] | S |
| 268. | [pyrrole-CH2OH, NH] | [tetrazole-ethyl] | S |
| 269. | [pyrrole-CH2OH, N-methyl] | [tetrazole-ethyl] | S |
| 270. | [imidazole-CH2OH, NH] | [tetrazole-ethyl] | S |
| 271. | [imidazole-CH2OH, N-methyl] | [tetrazole-ethyl] | S |
| 272. | [pyrazole-CH2OH, NH] | [tetrazole-ethyl] | S |
| 273. | [pyrazole-CH2OH, N-methyl] | [tetrazole-ethyl] | S |
| 274. | [imidazole-C(CH3)2OH, NH] | [CH2CH2OCH3] | S |
| 275. | [imidazole-C(CH3)2OH, NH] | [CH2CN] | S |
| 276. | [imidazole-C(CH3)2OH, NH] | [CH2CH2OCH3] | Se |
| 277. | [imidazole-C(CH3)2OH, NH] | [CH2CN] | Se |
| 278. | [imidazole, N-methyl] | [CH2C(CH3)2OH] | Se |
| 279. | [imidazole, N-ethyl] | [CH2C(CH3)2OH] | Se |
| 280. | [imidazole, N-isopropyl] | [CH2C(CH3)2OH] | Se |
| 281. | [benzimidazole, NH] | [CH2C(CH3)2OH] | Se |
| 282. | [imidazole, NH] | [CH2C(CH3)2OH] | Se |

TABLE B-continued

| | | | |
|---|---|---|---|
| 283. | 2-methyl-1H-imidazole | 2-methyl-2-butanol | Se |
| 284. | 2-CF₃-1H-imidazole | 2-methyl-2-butanol | Se |
| 285. | 2-ethyl-1H-imidazole | 2-methyl-2-butanol | Se |
| 286. | 2-isopropyl-1H-imidazole | 2-methyl-2-butanol | Se |
| 287. | 2-tert-butyl-1H-imidazole | 2-methyl-2-butanol | Se |
| 288. | 1H-pyrrole-2-carboxylic acid | 2-methyl-2-butanol | Se |
| 289. | 1-methyl-pyrrole-2-carboxylic acid | 2-methyl-2-butanol | Se |
| 290. | 1H-imidazole-4-carboxylic acid | 2-methyl-2-butanol | Se |
| 291. | 1-methyl-imidazole-4-carboxylic acid | 2-methyl-2-butanol | Se |
| 292. | 1H-pyrazole-3-carboxylic acid | 2-methyl-2-butanol | Se |
| 293. | 1-methyl-pyrazole-3-carboxylic acid | 2-methyl-2-butanol | Se |
| 294. | 5-(hydroxymethyl)-1H-pyrrole | 2-methyl-2-butanol | Se |
| 295. | 5-(hydroxymethyl)-1-methyl-pyrrole | 2-methyl-2-butanol | Se |
| 296. | 4-(hydroxymethyl)-1H-imidazole | 2-methyl-2-butanol | Se |
| 297. | 5-(hydroxymethyl)-1-methyl-imidazole | 2-methyl-2-butanol | Se |
| 298. | 3-(hydroxymethyl)-1H-pyrazole | 2-methyl-2-butanol | Se |
| 299. | 3-(hydroxymethyl)-1-methyl-pyrazole | 2-methyl-2-butanol | Se |
| 300. | 1H-pyrrole-2-carboxylic acid | 3-tert-butoxy-propyl | Se |
| 301. | 1-methyl-pyrrole-2-carboxylic acid | 3-tert-butoxy-propyl | Se |
| 302. | 1H-imidazole-4-carboxylic acid | 3-tert-butoxy-propyl | Se |
| 303. | 1-methyl-imidazole-4-carboxylic acid | 3-tert-butoxy-propyl | Se |
| 304. | 1H-pyrazole-3-carboxylic acid | 3-tert-butoxy-propyl | Se |

TABLE B-continued

| # | Group 1 | Group 2 | Se |
|---|---------|---------|-----|
| 305. | 1-methyl-pyrazole-3-carboxylic acid | -CH2CH2-O-C(CH3)3 | Se |
| 306. | 1H-pyrrole-2-methanol (2,5-disub) | -CH2CH2-O-C(CH3)3 | Se |
| 307. | 1-methyl-pyrrole-2-methanol (2,5-disub) | -CH2CH2-O-C(CH3)3 | Se |
| 308. | 1H-imidazole-4-methanol (2,4-disub) | -CH2CH2-O-C(CH3)3 | Se |
| 309. | 1-methyl-imidazole-5-methanol (2,5-disub) | -CH2CH2-O-C(CH3)3 | Se |
| 310. | 1H-pyrazole-3-methanol | -CH2CH2-O-C(CH3)3 | Se |
| 311. | 1-methyl-pyrazole-3-methanol | -CH2CH2-O-C(CH3)3 | Se |
| 312. | 1H-pyrrole-2-carboxylic acid | -CH2CH2-(N-imidazolyl) | Se |
| 313. | 1-methyl-pyrrole-2-carboxylic acid | -CH2CH2-(N-imidazolyl) | Se |
| 314. | 1H-imidazole-4-carboxylic acid (2,4-disub) | -CH2CH2-(N-imidazolyl) | Se |
| 315. | 1-methyl-imidazole-4-carboxylic acid (2,4-disub) | -CH2CH2-(N-imidazolyl) | Se |
| 316. | 1H-pyrazole-3-carboxylic acid | -CH2CH2-(N-imidazolyl) | Se |
| 317. | 1-methyl-pyrazole-3-carboxylic acid | -CH2CH2-(N-imidazolyl) | Se |
| 318. | 1H-pyrrole-2-methanol | -CH2CH2-(N-imidazolyl) | Se |
| 319. | 1-methyl-pyrrole-2-methanol | -CH2CH2-(N-imidazolyl) | Se |
| 320. | 1H-imidazole-4-methanol (2,4-disub) | -CH2CH2-(N-imidazolyl) | Se |
| 321. | 1-methyl-imidazole-5-methanol (2,5-disub) | -CH2CH2-(N-imidazolyl) | Se |
| 322. | 1H-pyrazole-3-methanol | -CH2CH2-(N-imidazolyl) | Se |
| 323. | 1-methyl-pyrazole-3-methanol | -CH2CH2-(N-imidazolyl) | Se |
| 324. | 1H-pyrrole-2-carboxylic acid | -CH2-(tetrazol-5-yl) | Se |
| 325. | 1-methyl-pyrrole-2-carboxylic acid | -CH2-(tetrazol-5-yl) | Se |
| 326. | 1H-imidazole-4-carboxylic acid (2,4-disub) | -CH2-(tetrazol-5-yl) | Se |

TABLE B-continued

| # | Structure 1 | Structure 2 | X |
|---|---|---|---|
| 327. | 1-methyl-imidazole-5-carboxylic acid (attached at 2-position) | CH₂-tetrazole | Se |
| 328. | 1H-pyrazole-3-carboxylic acid (attached at 5-position) | CH₂-tetrazole | Se |
| 329. | 1-methyl-pyrazole-3-carboxylic acid (attached at 5-position) | CH₂-tetrazole | Se |
| 330. | 5-(hydroxymethyl)-1H-pyrrole (attached at 2-position) | CH₂-tetrazole | Se |
| 331. | 5-(hydroxymethyl)-1-methyl-pyrrole (attached at 2-position) | CH₂-tetrazole | Se |
| 332. | 5-(hydroxymethyl)-1H-imidazole (attached at 2-position) | CH₂-tetrazole | Se |
| 333. | 5-(hydroxymethyl)-1-methyl-imidazole (attached at 2-position) | CH₂-tetrazole | Se |
| 334. | 3-(hydroxymethyl)-1H-pyrazole (attached at 5-position) | CH₂-tetrazole | Se |
| 335. | 3-(hydroxymethyl)-1-methyl-pyrazole (attached at 5-position) | CH₂-tetrazole | Se |
| 336. | 1-(carboxymethyl)-pyrrole (attached at 2-position) | H | Se |
| 337. | 1-methyl-pyrrole (attached at 2-position) | H | Se |
| 338. | 1,5-dimethyl-pyrrole (attached at 2-position) | H | Se |
| 339. | 5-ethyl-1-methyl-pyrrole (attached at 2-position) | H | Se |
| 340. | 1H-pyrrole (attached at 2-position) | H | Se |
| 341. | 5-methyl-1H-pyrrole (attached at 2-position) | H | Se |
| 342. | 5-ethyl-1H-pyrrole (attached at 2-position) | H | Se |
| 343. | 1H-imidazole (attached at 2-position) | H | Se |
| 344. | 5-methyl-1H-imidazole (attached at 2-position) | H | Se |
| 345. | 5-ethyl-1H-imidazole (attached at 2-position) | H | Se |
| 346. | 1-methyl-imidazole (attached at 2-position) | H | Se |
| 347. | 1,5-dimethyl-imidazole (attached at 2-position) | H | Se |
| 348. | 5-ethyl-1-methyl-imidazole (attached at 2-position) | H | Se |
| 349. | 1H-imidazole (attached at 4-position) | H | Se |

TABLE B-continued

| | | | |
|---|---|---|---|
| 350. |  2-methyl-1H-imidazole | H | Se |
| 351. | 2-ethyl-1H-imidazole | H | Se |
| 352. | 1H-pyrrole-2-carboxylic acid | H | Se |
| 353. | 1-methyl-pyrrole-2-carboxylic acid | H | Se |
| 354. | 1H-imidazole-4-carboxylic acid | H | Se |
| 355. | 1-methyl-imidazole-5-carboxylic acid | H | Se |
| 356. | 1H-pyrazole-3-carboxylic acid | H | Se |
| 357. | 1-methyl-pyrazole-3-carboxylic acid | H | Se |
| 358. | (1H-pyrrol-2-yl)methanol | H | Se |
| 359. | (1-methyl-pyrrol-2-yl)methanol | H | Se |
| 360. | (1H-imidazol-4-yl)methanol | H | Se |
| 361. | (1-methyl-imidazol-5-yl)methanol | H | Se |
| 362. | (1H-pyrazol-3-yl)methanol | H | Se |
| 363. | (1-methyl-pyrazol-3-yl)methanol | H | Se |
| 364. | 1H-pyrrole-2-carboxylic acid | CH₂CH₂OH | Se |
| 365. | 1-methyl-pyrrole-2-carboxylic acid | CH₂CH₂OH | Se |
| 366. | 1H-imidazole-4-carboxylic acid | CH₂CH₂OH | Se |
| 367. | 1-methyl-imidazole-5-carboxylic acid | CH₂CH₂OH | Se |
| 368. | 1H-pyrazole-3-carboxylic acid | CH₂CH₂OH | Se |
| 369. | 1-methyl-pyrazole-3-carboxylic acid | CH₂CH₂OH | Se |
| 370. | (1H-pyrrol-2-yl)methanol | CH₂CH₂OH | Se |
| 371. | (1-methyl-pyrrol-2-yl)methanol | CH₂CH₂OH | Se |
| 372. | (1H-imidazol-5-yl)methanol | CH₂CH₂OH | Se |

TABLE B-continued

| 373. | [imidazole-CH2OH structure] | [CH2CH2CH2OH] | Se |
| 374. | [pyrazole-CH2OH structure] | [CH2CH2CH2OH] | Se |
| 375. | [N-methyl pyrazole-CH2OH structure] | [CH2CH2CH2OH] | Se |

In one embodiment the compound is a compound of the formula

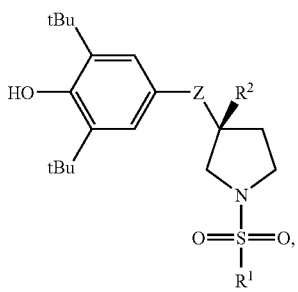

wherein Z, $R^1$ and $R^2$ are as defined above.

In another embodiment the compound is a compound of the formula

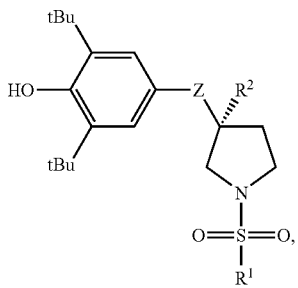

wherein Z, $R^1$ and $R^2$ are as defined above.

In certain embodiments, the compounds are present as enantiomers. In particular embodiments, the compound is present as a racemic mixture. The enantiomer can be named by the configuration at the chiral center, such as R or S. In particular embodiments, the compound is present as an enantiomer when X does not equal Y, such as in compounds of Formula III. In certain embodiments, the compound is present as a racemic mixture of R- and S-enantiomers. In certain embodiments, the compound is present as a mixture of two enantiomers. In one embodiment, the mixture has an enantiomeric excess in R. In one embodiment, the mixture has an enantiomeric excess in S. In certain other embodiments, the compound is in an enantiomeric excess of the R- or S-enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the single enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the R enantiomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the S enantiomer.

In other embodiments, the compound is substantially in the form of a single enantiomer. For example, the compound can be a compound of the formula

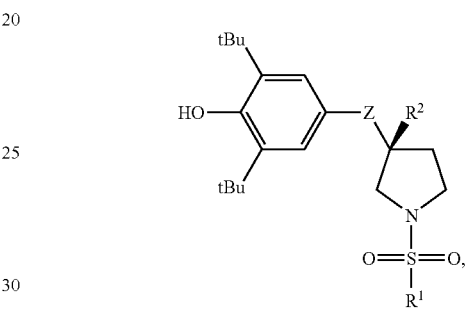

or a compound of the formula

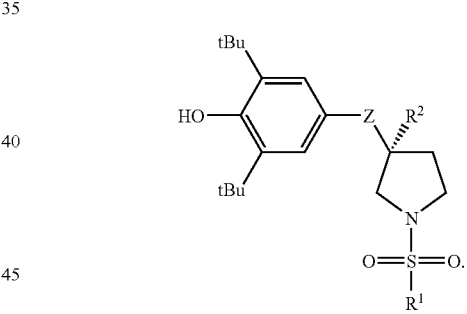

In other embodiments, the compound is present as a mixture of enantiomers.

In some embodiments, the compound is present substantially in the form of the R enantiomer. In some embodiments, the compound is present substantially in the form of the S enantiomer. The phrase "substantially in the form of a single enantiomer" is intended to mean at least 70% or more in the form of a single enantiomer, for example 70% or more, 75% or more, 80% or more, 85% or more, 90% or more, 95% or more, 98% or more, or 99% or more in either the R or S enantiomer.

The enantiomer can be named by the direction in which it rotates the plane of polarized light. If it rotates the light clockwise as seen by the viewer towards whom the light is traveling, the isomer can be labeled (+) and if it rotates the light counterclockwise, the isomer can be labeled (−). In certain embodiments, the compound is present as a racemic mixture of (+) and (−) isomers. In certain embodiments, the compound is present as a mixture of two isomers. In one embodiment, the mixture has an excess in (+). In one embodiment, the mixture has an excess in (−). In certain other embodiments, the compound is in an excess of the (+) or (−) isomer. The isomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (+) isomer. The enantiomeric excess can be 51% or more, such as 51% or more, 55% or more, 60% or more, 65% or more, 70% or more, 75% or more, 80% or more, 85% or more, 90% or more, 95% or more, 98% or more, or 99% or more in the (−) isomer.

In other embodiments, the compound is substantially in the form of a single optical isomer. In some embodiments, the compound is present substantially in the form of the (+) isomer. In other embodiments, the compound is present substantially in the form of the (−) isomer. The phrase "substantially in the form of a single optical isomer" is intended to mean at least 70% or more in the form of a single isomer, for example 70% or more, 75% or more, 80% or more, 85% or more, 90% or more, 95% or more, 98% or more, or 99% or more of either the (+) or (−) isomer.

DEFINITIONS

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" as used herein, unless otherwise specified, refers to a saturated straight, branched, or cyclic (also identified as cycloalkyl), primary, secondary, or tertiary hydrocarbon, including but not limited to those of $C_1$ to $C_6$. The term alkyl also includes lower alkyl. Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, carboxy, acyl, acyloxy, amino, amido, carboxyl derivatives, alkylamino, dialkylamino, arylamino, alkoxy, aryloxy, nitro, cyano, thio, sulfonyl, ester, carboxylic acid, amide, phosphonyl, phosphinyl, thioether, oxime, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991. In certain embodiments, alkyl may be optionally substituted by one or more halo, hydroxy, heterocyclic, heteroaryl, carboxy, —$NR^5R^6$, alkoxycarbonyl, —$NR^6C(O)R^5$, —$NR^6C(O)NR^5R^6$, —$NR^6C(O)OR^5$, —$OC(O)NR^5R^6$, —$OR^5$, —$C(O)R^5$, —$S(O)_n$—$R^5$, —$C(O)$—$NR^5R^6$, and/or cyano. In certain embodiments, the alkyl may be optionally substituted by one or more halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$OC(O)NR^5R^6$, —$NR^6C(O)OR^5$, —$S(O)_n$—$R^5$, —$S(O)_2$—$NH_2$, —$S(O)_n$—$N(H)R^5$ and/or —$S(O)_2$—$NR^5R^6$.

The term "lower alkyl," unless otherwise specified, refers to a $C_1$ to $C_5$ saturated or unsaturated straight, branched carbon chain such as methyl, ethyl, isopropyl, n-butyl, tert-butyl, n-pentyl, sec-pentyl, 3-methylpentyl, and the like, or if appropriate, a cyclic (for example, cyclopropyl) alkyl group.

The term "halo" or "halogen," refers to chloro, bromo, iodo, or fluoro.

The term "heteroaryl" or "heteroaromatic," refers to an aromatic that includes at least one sulfur, oxygen, nitrogen or phosphorus in the aromatic ring. The term "heterocyclic" refers to a non-aromatic cyclic group wherein there is at least one heteroatom, such as oxygen, sulfur, nitrogen, or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, pteridinyl, aziridines, thiazole, isothiazole, oxadiazole, thiazine, pyridine, pyrazine, piperazine, piperidine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic or heterocyclic group can be optionally substituted with one or more substituent selected from halogen, haloalkyl, alkyl, alkoxy, hydroxy, carboxy, carboxyl derivatives, amido, amino, alkylamino, dialkylamino. The heteroaromatic can be partially or totally hydrogenated as desired. Nonlimiting examples include dihydropyridine and tetrahydrobenzimidazole. In some embodiment, the heteroaryl may be optionally substituted by one or more halo, alkyl, alkenyl, cycloalkyl, acyl, hydroxy, hydroxyalkyl, heterocyclic, heteroaryl, aryl, amino, aminoalkyl, —$NR^5R^6$, oxo, cyano, carboxy, carboxyalkyl, alkoxycarbonyl, —$OR^5$, —$C(O)R^5$, —$C(O)$—$NH_2$, —$C(O)$—$N(H)R^5$, —$C(O)$—$N(H)OR^5$, —$C(O)$—$NR^5R^6$, —$NR^6C(O)R^5$, —$NR^6C(O)NR^5R^6$, —$OC(O)NR^5R^6$, —$NR^6C(O)OR^5$, —$S(O)_n$—$R^5$, —$S(O)_2$—$NH_2$, —$S(O)_n$—$N(H)R^5$ and/or —$S(O)_2$—$NR^5R^6$. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "aryl," unless otherwise specified, refers to a carbon based, or carbocyclic, aromatic ring, including phenyl, biphenyl, or naphthyl. The aryl group can be optionally substituted with one or more moieties selected from the group consisting of hydroxyl, carboxy, alkyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. In certain embodiments, the aryl group is optionally substituted by one or more halo, alkyl, alkenyl, cycloalkyl, acyl, hydroxy, hydroxyalkyl, heterocyclic, heteroaryl, aryl, amino, aminoalkyl, —NR$^7$R$^8$, oxo, cyano, carboxy, carboxyalkyl, alkoxycarbonyl, —OR$^9$—C(O)R$^9$, —C(O)—NH$_2$, —C(O)—N(H)R$^7$, —C(O)—NR$^7$R$^8$, —NR$^7$C(O)R$^9$, —NR$^7$C(O)OR$^9$, —S(O)$_n$—R$^9$, —S(O)$_2$—NH$_2$, —S(O)$_2$—N(H)R$^7$ and/or —S(O)$_2$—NR$^7$R$^8$.

The term "aralkyl," unless otherwise specified, refers to an aryl group as defined above linked to the molecule through an alkyl group as defined above. The term "alkaryl," unless otherwise specified, refers to an alkyl group as defined above linked to the molecule through an aryl group as defined above. Other groups, such as acyloxyalkyl, alkoxyalkyl, alkoxycarbonyl, alkoxycarbonylalkyl, alkylaminoalkyl, alkylthioalkyl, amidoalkyl, aminoalkyl, carboxyalkyl, dialkylaminoalkyl, haloalkyl, heteroaralkyl, heterocyclicalkyl, hydroxyalkyl, sulfonamidoalkyl, sulfonylalkyl, thioalkyl, and alkoxycarbonyl are named in a similar manner.

The term "alkoxy," unless otherwise specified, refers to a moiety of the structure —O-alkyl, wherein alkyl is as defined above.

The term "acyl," refers to a group of the formula C(O)R', wherein R' is an alkyl, aryl, alkaryl or aralkyl group, or substituted alkyl, aryl, aralkyl or alkaryl.

The term "alkenyl" The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to (C2-C8)-alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "carbonyl" refers to a functional group composed of a carbon atom double-bonded to an oxygen atom: —C=O.

The term "amino" refers to an —NH$_2$ group or an —N(alkyl)$_2$ group.

The term "thio" indicates the presence of a sulfur group. The prefix thio- denotes that there is at least one extra sulfur atom added to the chemical. The prefix 'thio-' can also be placed before the name of a compound to mean that an oxygen atom in the compound has been replaced by a sulfur atom. Although typically the term "thiol" is used to indicate the presence of —SH, in instances in which the sulfur atom would be have improper valance a radical if the hydrogen is improperly designated, the terms 'thio' and 'thiol' are used interchangeably, unless otherwise indicated.

The term "amido" indicates a group R—CO—NH—.

The term "carboxy" designates the terminal group —C(O)OH.

The term "sulfonyl" indicates an organic radical of the general formula R—S(=O)$_2$—R', where there are two double bonds between the sulfur and oxygen.

The term "pharmaceutically acceptable salt" refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, for example, as taught in Greene, et al., *Protective Groups in Organic Synthesis*, John Wiley and Sons, Second Edition, 1991.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

Methods of Use

The compounds of the invention can generally be administered to a host at risk of, or suffering from, an inflammatory condition. In one embodiment, the compounds are administered for the treatment or prophylaxis of an inflammatory disorder. In certain embodiments, the inflammatory disorder is a respiratory disorder. In particular embodiments, the inflammatory disorder is asthma or chronic obstructive pulmonary disease (COPD). In other, separate embodiments the inflammatory disorder is a cardiovascular disorder. In certain embodiments, the inflammatory condition is mediated by known cytokines such as IL-6 or IL-8. In other embodiments, the inflammatory condition is unrelated to levels of any particular cytokines, such as IL-6 or IL-8. Certain of the compounds of the invention are useful in the treatment of inflammatory respiratory conditions, such as asthma, independently of their effect on inflammatory cytokines related to chemotaxis or antibody-mediated immune responses.

Cytokines are small secreted proteins which mediate and regulate immunity, inflammation, and hematopoiesis. They must be produced de novo in response to an immune stimulus. They generally (although not always) act over short distances and short time spans and at very low concentration. They act by binding to specific membrane receptors, which then signal the cell via second messengers, often tyrosine kinases, to alter its behavior (gene expression). Responses to cytokines include increasing or decreasing expression of membrane proteins (including cytokine receptors), proliferation, and secretion of effector molecules.

It is common for different cell types to secrete the same cytokine or for a single cytokine to act on several different cell types Cytokines are redundant in their activity, meaning similar functions can be stimulated by different cytokines. The largest group of cytokines stimulates immune cell proliferation and differentiation. This group includes Interleukin 1 (IL-1), which activates T cells; IL-2, which stimulates proliferation of antigen-activated T and B cells; IL-4, IL-5, and IL-6, which stimulate proliferation and differentiation of B cells; Interferon gamma (IFNγ), which activates macrophages; and IL-3, IL-7 and Granulocyte Monocyte Colony-Stimulating Factor (GM-CSF), which stimulate hematopoiesis. IL-6 is generally produced by monocytes, macrophages, Th2 cells and stromal cells. It acts on activated B cells to differentiate into plasma cells, plasma cells to induce antibody secretion, stem cells to induce differentiation, and on various other cells to induce acute inflammatory responses. IL-8, produced by macrophages and endothelial cells generally acts on neutrophils to induce chemotaxis.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barré, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

Respiratory Disorders

In one embodiment, compounds, compositions and methods of treatment of respiratory disorders comprising administering a compound are provided wherein the compound is as described herein. Respiratory disorders that may be prevented or treated include a disease or disorder of the respiratory system that can affect any part of the respiratory tract. These conditions range from life threatening to mild. Certain diseases cause respiratory symptoms although the diseases are initially caused by an infection, such as a cold virus, bronchitis, pneumonia and tuberculosis. Other disorders are caused by irritation of the lung tissue, such as, for example, by an allergen. These disorders include hay fever and other respiratory allergies and asthma. In certain embodiments, the host is at risk of or suffering from a disorder of the lower airway. These include bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis.

In asthma, the bronchi and bronchioles are typically temporarily constricted and inflamed. Other disorders typically involving lung irritants include emphysema, which can result from multiple factors including: smog, cigarette smoke, infection, and a genetic predisposition to the condition, laryngitis, lung cancer, respiratory distress syndrome (RDS), which refers to a group of symptoms that indicate severe malfunctioning of the lungs affecting adults and infants and specifically Adult respiratory distress syndrome (ARDS). Chronic respiratory insufficiency (or chronic obstructive pulmonary disease; COPD) is a prolonged or persistent condition characterized by breathing or respiratory dysfunction resulting in reduced rates of oxygenation or the ability to eliminate carbon dioxide.

The term "asthma" as used herein includes any asthmatic condition marked by recurrent attacks of paroxysmal dyspnea (i.e., "reversible obstructive airway passage disease") with wheezing due to spasmodic contraction of the bronchi (so called "bronchospasm"). Asthmatic conditions which may be treated or even prevented in accordance with this invention include allergic asthma and bronchial allergy characterized by manifestations in sensitized persons provoked by a variety of factors including exercise, especially vigorous exercise ("exercise-induced bronchospasm"), irritant particles (pollen, dust, cotton, cat dander) as well as mild to moderate asthma, chronic asthma, severe chronic asthma, severe and unstable asthma, nocturnal asthma, and psychologic stresses.

Other respiratory disorders include allergic and non-allergic rhinitis as well as non-malignant proliferative and/or inflammatory disease of the airway passages and lungs. Allergic rhinitis means generally any allergic reaction of the nasal mucosa and includes hay fever (seasonal allergic rhinitis) and perennial rhinitis (non-seasonal allergic rhinitis) which are characterized by seasonal or perennial sneezing, rhinorrhea, nasal congestion, pruritis and eye itching, redness and tearing. Non-allergic rhinitis means eosinophilic nonallergic rhinitis which is found in patients with negative skin tests and those who have numerous eosinophils in their nasal secretions.

Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the use of the compounds of the invention reduces symptoms of these disorders, including cough, shortness of breath, chest pain, wheezing, cyanosis, finger clubbing, stridor (a crowing sound when breathing), hemoptysis (coughing up of blood), and respiratory failure. The use of these compounds may reduce respiratory acidosis, due to a failure by the lungs to remove carbon dioxide.

In another embodiment, the use of the compounds improves lung function.

Cardiovascular Related Disorders

In one embodiment, the compounds of the invention are administered to a patient suffering from a cardiovascular disorder related to inflammation. These include, but are not limited to, atherosclerosis, post-angioplasty restenosis, coronary artery diseases and angina.

Generally, cardiovascular disorders are a class of diseases that involve the heart and/or blood vessels (arteries and veins). While the term technically refers to any disease that affects the cardiovascular system, it is usually used to refer to those related to atherosclerosis (arterial disease).

Cardiovascular inflammatory disorders include atherosclerosis, post-angioplasty, restenosis, coronary artery diseases, angina, and other cardiovascular diseases. In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes. In an alternative embodiment, the compounds can be administered to treat small vessel disease that is not treatable by surgery or angioplasty, or other vessel disease in which surgery is not an option. The compounds can also be used to stabilize patients prior to revascularization therapy.

Generally, unstable atherosclerotic plaque is a result of multiple factors but is commonly characterized by an infiltrate of inflammatory cells. Medical research strongly supports a role for inflammation in the pathogenesis, progression, and disruption of atherosclerotic plaque. Clinical studies have demonstrated systemic markers of inflammation to be strong predictors of clinical events, and specific treatments of atherosclerosis and its risk factors have been associated with reductions in inflammatory markers. The majority of cardiovascular events occur at sites of "nonsignificant" stenosis, as inflammation can lead to instability and rupture of these smaller atherosclerotic plaques, which are more numerous than the "significant," flow-limiting plaques. In fact, direct visualization of inflammatory cells within plaques is a predictor of unstable coronary disease. The source of inflammation is uncertain; various infectious agents have been proposed as a stimulator of this inflammatory process. Smooth muscle cell proliferation is also implicated both in chronic cardiovascular pathologies such as atherosclerosis, and more directly in, for example, post-angioplasty restenosis.

Diseases of arteries, arterioles and capillaries generally include atherosclerosis, peripheral vascular diseases including Raynaud's syndrome, thromboangiitis obliterans (Buerger) and other specified peripheral vascular diseases such as intermittent claudication.

Proliferative Disorders

Chronic inflammation is a risk factor for many proliferative disorders. For example, in a variety of diseases, airway smooth muscle mass increases due to the coordinated increase in size (hypertrophy) and number (hyperplasia) of airway smooth muscle cells. Myocyte migration may also serve to regulate airway smooth muscle mass. For example, chronic cellular inflammation and airway wall remodelling with subepithelial fibrosis and airway smooth muscle (ASM) cell hyperplasia are features of chronic asthma. In addition, vascular smooth muscle, and immune cells are stimulated in cardiovascular disorders.

In particular, inflammation is a risk factor in development of cancers, including colon cancer, and data from experimental and observational studies suggest that inflammation acts early in the carcinogenic pathway of colorectal cancer, possibly promoting the progression of colorectal adenomas to adenocarcinoma (Tangrea et al. Non-steroidal anti-inflammatory drug use is associated with reduction in the recurrence of advanced and non-advanced colorectal adenomas. *Cancer Causes Control* 2003; 14:403-11; Dranoff G. Cytokines in cancer pathogenesis and cancer therapy. *Nat Rev Cancer* 2004; 4:11-22; O'Byrne et al. Chronic immune activation and inflammation as the cause of malignancy. *Br J Cancer* 2001; 85:473-783; Balkwill et al. Inflammation and cancer: back to Virchow *Lancet* 2001; 357:539-45; Coussens et al. Inflammation and cancer. *Nature* 2002; 420:860-7). The inflammatory response to cellular stresses, injury and infection, results from increased mucosal production of proinflammatory cytokines. Proinflammatory cytokines, such as tumor necrosis factor α, and the interleukins (IL-1β, IL-6, and IL-8), play a key role in angiogenesis, inhibition of apoptosis, and cell proliferation. These cytokines induce expression of cyclooxygenase 2 (COX-2), one of the key enzymes in the production of prostaglandins. COX-2 mRNA and protein are present in both colorectal adenomas and adenocarcinomas, and thus support a role of inflammation early in the carcinogenic pathway of colorectal cancer.

Other Inflammatory Disorders

In another embodiment, the compounds of the invention may be administered for the treatment or prophylaxis of an inflammatory disorder or the joints or connective tissue. These disorders include rheumatoid arthritis, lupus erythematosus, Sjögren's syndrome, scleroderma (systemic sclerosis), dermatomyositis, polychondritis, polymyositis, polymyalgia rheumatica, osteoarthritis, septic arthritis, fibromyalgia, gout, pseudogout, spondyloarthropathies, such as ankylosing spondylitis, reactive arthritis (Reiter's syndrome), psoriatic arthropathy, enteropathic spondylitis and reactive arthropathy, vasculitis, such as polyarteritis nodosa, Henoch-Schönlein purpura, serum sickness, Wegener's granulomatosis, giant cell arteritis, temporal arteritis, Takayasu's arteritis, Behçet's syndrome, Kawasaki's disease (mucocutaneous lymph node syndrome) and Buerger's disease (thromboangiitis obliterans). In addition, autoimmune conditions such as acute disseminated encephalomyelitis, Addison's disease, ankylosing spondylitisis, antiphospholipid antibody syndrome, autoimmune hepatitis, Coeliac disease, Crohn's disease, Graves' disease, Guillain-Barré syndrome, Hashimoto's disease, idiopathic thrombocytopenic purpura, Kawasaki's Disease, lupus erythematosus, multiple sclerosis, Myasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, warm autoimmune hemolytic anemia and Wegener's granulomatosis.

In other embodiments, certain inflammatory skin disorders are treated or prevented, such as dermatitis, eczematous dermatitis and psoriasis. In general inflammatory skin disease is a broad category that includes many conditions, ranging in severity from mild itching to serious medical health complications. Other conditions that are inflammatory skin disorders include eczema generally, acne and rosacea.

Other disorders may also be treated or prophylactically prevented or reduced by administration of compounds of the invention. In certain embodiments, the disorder to be treated is selected from post transplantation late and chronic solid organ rejection; multiple sclerosis; autoimmune conditions (including systemic lupus erythematosus, dermatomyositis, polymyositis, inflammatory neuropathies (Guillain Barré, inflammatory polyneuropathies), vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis).

Pharmaceutical Compositions

Mammals, and specifically humans, suffering from an inflammatory disorder, including any of the above-described conditions, and in particular suffering from respiratory disorders, can be treated by either targeted or systemic administration, via oral, inhalation, topical, trans- or sub-mucosal, subcutaneous, parenteral, intramuscular, intravenous or transdermal administration of a composition comprising an effective amount of the compounds described herein or a pharmaceutically acceptable salt, ester or prodrug thereof, optionally in a pharmaceutically acceptable carrier.

The compounds or composition is typically administered by oral administration. Alternatively, compounds can be administered by inhalation. In another embodiment, the compound is administered transdermally (for example via a slow release patch), or topically. In yet another embodiment, the compound is administered subcutaneously, intravenously, intraperitoneally, intramuscularly, parenterally, or submucosally. In any of these embodiments, the compound is administered in an effective dosage range to treat the target condition.

The active compound is included in the pharmaceutically acceptable carrier or diluent in an amount sufficient to deliver to a patient a therapeutically effective amount without causing serious toxic effects in the patient treated. In one embodiment, the dose of the active compound for all of the above-mentioned conditions is in the range from about 0.01 to 500 mg/kg, or 0.1 to 500 mg/kg, about 0.1 to 100 mg/kg per day, about 0.1 to 50 mg/kg per day, about 0.1 to 20 mg/kg per day, about 0.1 to 10 mg/kg per day, about 0.1 to 5 mg/kg per day, or about 0.5 to 2 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

In one embodiment, compounds of the present invention are administered orally. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

When the compound is administered orally in the form of a dosage unit such as a tablets, pills, capsules, troches and the like, these can contain any of the following ingredients, or compounds of a similar nature: a binder (such as microcrystalline cellulose, gum tragacanth or gelatin); an excipient (such as starch or lactose), a disintegrating agent (such as alginic acid, Primogel, or corn starch); a lubricant (such as magnesium stearate or Sterotes); a glidant (such as colloidal silicon dioxide); a sweetening agent (such as sucrose or saccharin); and/or a flavoring agent (such as peppermint, methyl salicylate, or orange flavoring). When the dosage unit form is a capsule, it can contain, in addition to material of the above type, a liquid carrier (such as a fatty oil). In addition, dosage unit forms can contain various other materials which modify the physical form of the dosage unit, for example, coatings of sugar, shellac, or other enteric agents.

The compound or its salts can also be administered orally as a component of an elixir, suspension, syrup, wafer, chewing gum or the like. A syrup may contain, in addition to the active compounds, a sweetening agent (such as sucrose, saccharine, etc.) and preservatives, dyes and colorings and flavors.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: povidone, suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

Solutions or suspensions used for parenteral, intradermal, subcutaneous, or topical application can include at least some of the following components: a sterile diluent (such as water for injection, saline solution, fixed oils, polyethylene glycols, glycerine, propylene glycol or other synthetic solvents); antibacterial agents (such as benzyl alcohol or methyl parabens); antioxidants (such as ascorbic acid or sodium bisulfite); chelating agents (such as ethylenediaminetetraacetic acid); buffers (such as acetates, citrates or phosphates); and/or agents for the adjustment of tonicity (such as sodium chloride or dextrose). The pH of the solution or suspension can be adjusted with acids or bases, such as hydrochloric acid or sodium hydroxide.

A parenteral preparation can be enclosed in ampoules, disposable syringes or multiple dose vials made of glass or plastic.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

If administered intravenously, carriers can be physiological saline, bacteriostatic water, Cremophor EL™ (BASF, Parsippany, N.J.) or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Dosing

The compound is administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single dosage once a day, such as, for example, an oral, intravascular or inhaled dosage. In some embodiments, the compounds are administered in a single oral dosage once a day.

The active compound is included in the pharmaceutically acceptable carrier or diluent in an amount sufficient to deliver to a patient a therapeutic amount of compound in vivo in the absence of serious toxic effects. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

For systemic administration, the compound is conveniently administered in any suitable unit dosage form, including but not limited to one containing 1 to 3000 mg, 5 to 500 mg, 10 to 400 mg, 10 to 300 mg, 10 to 200 mg, 25 to 150 mg, or 10 to 100 mg of active ingredient per unit dosage form. An oral dosage of 25-350 mg is usually convenient. The unit dosage form may be administered once daily, twice daily, threes times daily or four times daily. The active ingredient should be administered to achieve peak plasma concentrations of the active compound of about 0.1 to 100 mM, preferably about 1-10 mM. This may be achieved, for example, by the intravenous injection of a solution or formulation of the active ingredient, optionally in saline, or an aqueous medium or administered as a bolus of the active ingredient.

Typical systemic dosages for all of the herein described conditions are those ranging from 0.1 mg/kg to 500 mg/kg of body weight per day as a single daily dose or divided daily doses. Preferred dosages for the described conditions range from 5-1500 mg per day. A more particularly preferred dosage for the desired conditions ranges from 10-750, 10-400, 10-300, 10-150, 20-80, or 50-100 mg per day. Typical dosages for topical application are those ranging from 0.001 to 100% by weight of the active compound. In one embodiment, the compounds are given in doses of between about 0.1-10 mg/kg. In one embodiment, the compounds are given in doses of between about 0.1-3 mg/kg.

In certain embodiments, the dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg.

The length of dosing will range from a single dose given only once to twice daily dosages given over the course of at least six months, at least one year, or more.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Treatment

The compound can also be mixed with other active materials which do not impair the desired action, or with materials that supplement the desired action. The active compounds can be administered in conjunction, i.e. combination or alternation, with other medications used in the treatment of respiratory disorders. In another embodiment, the compounds can be administered in conjunction (combination or alternation) with other medications used in treatment or prophylaxis of inflammatory conditions. In certain embodiments, the combination can be synergistic.

In one embodiment, the compounds can be administered in combination or alternation with drugs typically useful for treatment or prevention of respiratory conditions such as asthma, such as certain anti-inflammatory drugs and bronchodilators. Corticosteroids (inhaled and oral), mast cell stabilizers, and the leukotriene modifier drugs are typically a useful anti-inflammatory medication for people suffering from asthma. These drugs reduce swelling and mucus production in the airways. Bronchodilators typically relieve the symptoms of asthma by relaxing the muscle bands that tighten around the airways. This action rapidly opens the airways, letting more air come in and out of the lungs. Bronchodilators also help clear mucus from the lungs.

Typically used compounds include inhaled corticosteroids, which prevent rather than relieve symptoms. Inhaled corticosteroids include: Advair (a combination medication that includes a corticosteroid (fluticasone) plus a long acting bronchodilator drug (in this case a β-2 adrenergic receptor agonist, salmeterol)), aerobid (flunisolide), azmacort (triamcinolone), flovent (fluticasone), methylprednisolone, prednisone, pulmicort or serevent diskus (salmeterol powder), theophylline, qvar, and xopenex (levalbuterol), Inhaled corticosteroids come in three forms: the metered dose inhaler (MDI), dry powder inhaler (DPI) and nebulizer solutions. Systemic steroids include: methylprednisolone (Medrol, Methylpred, Solu-Medrol), prednisone (Deltasone) and prednisolone (Prelone, Pediapred, Orapred). Mast Cell Stabilizers include Intal and Tilade, which work by preventing the release of irritating and inflammatory substances from mast cells. Leukotriene modifiers include accolate and singular and accolate (zafirlukast), singulair (montelukast) and zyflo (zileuton).

The compounds can be administered in combination with nonsteroidal antiinflammatories such as ibuprofen, indomethacin, fenoprofen, mefenamic acid, flufenamic acid, sulindac. The compound can also be administered with corticosteriods. Any of the compounds described herein for combination or alternation therapy can be administered as any prodrug that upon administration to the recipient, is capable of providing directly or indirectly, the parent compound. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound.

In another embodiment, the active compounds can be administered in conjunction with medications used in the treatment or prophylaxis of conditions associated with cardiovascular disease. These compounds include lipid lowering agents, such as statins, probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalapril, and β-blockers such as propanalol, terbutalol, and labetalol. The compounds can also be administered in combination with nonsteroidal antiinflammatories such as ibuprofen, indomethacin, fenoprofen, mefenamic acid, flufenamic acid, sulindac. The compound can also be administered, for example, with corticosteriods.

In some embodiments, the compounds are administered in combination or alternation with ACE (angiotensin-converting enzyme) inhibitors. Nonlimiting examples are captopril (Capoten), enalapril (Vasotec), lisinopril (Prinivil, Zestril), quinapril (Accupril), ramipril (Altace), benazepril (Lotensin) and fosinopril (Monopril). In another embodiment, the compounds are administered in combination or alternation with beta blockers. Nonlimiting examples are atenolol (Tenormin), carvedilol (Coreg), labetolol (Normodyne), metoprolol (Lopressor, Toprol) and propanolol (Inderal). In another embodiment, the compounds are administered in combination or alternation with blood thinners such as aspirin or warfarin (Coumadin) or calcium channel blockers such as amlodipine (Norvasc), diltiazem (Cardizem, Dilacor), nifedipine (Adalat, Procardia), nicardipine (Cardene) or verapamil (Calan). In another embodiment, the compounds are administered in combination or alternation with a statin. Nonlimiting examples of currently used statins are lovastatin (Mevacor, Altocor), pravastatin (Pravachol), simvastatin (Zocor), fluvastatin (Lescol), atorvastatin (Lipitor).

The compounds can also be administered in combination or alternation with compounds that are generally used for treatment of skin inflammatory conditions, such as Acitretin, Alclometasone dipropionate, Allantoin/Coal tar extract/Hydrocortisone, Alphaderm, Alphosyl HC, Asmanex, Benzalkonium chloride/Dimeticone 350/Hydrocortisone/Nystatin, Betacap, Betamethasone dipropionate, Betamethasone dipropionate/Calcipotriol hydrate, Betamethasone dipropionate/Salicylic acid, Betamethasone Valerate, Betamethasone Valerate/Clioquinol, Betamethasone Valerate/Fusidic Acid, Betamethasone valerate/Neomycin sulphate, Betnovate, Betnovate-C, Betnovate-N, Bettamousse, Calcipotriol, Calcipotriol hydrate, Calcitriol, Calmurid HC, Canesten HC, Chlorquinaldol/Hydrocortisone Butyrate, Cyclosporin, Clarelux, Clioquinol/Hydrocortisone, Clobetasol propionate, Clobetasol propionate/Neomycin sulphate/Nystatin, Clobetasone butyrate, Clobetasone butyrate/Nystatin/Oxytetracycline calcium, Clotrimazole/Hydrocortisone, Crotamiton/Hydrocortisone, Cutivate, Daktacort, Dandrazol, Dermovate, Dermovate-NN, Dioderm, Diprosalic, Diprosone, Dithranol, Dithrocream, Dovobet, Dovonex, Dovonex cream, Econacort, Econazole nitrate/Hydrocortisone, Efalizumab, Efcortelan, Elidel, Enbrel, Etanercept, Eumovate, Eurax Hydrocortisone, Fluticasone propionate, Fucibet, Fucidin H, Fucidin H ointment, Fusidic acid/Hydrocortisone acetate, Gramicidin/Neomycin sulphate/Nystatin/Triamcinolone acetonide, Hydrocortisone, Hydrocortisone acetate/Sodium fusidate, Hydrocortisone butyrate, Hydrocortisone/Lactic Acid/Urea, Hydrocortisone/Miconazole nitrate, Hydrocortisone/Urea, Infliximab, Kenalog, Ketoconazole, Locoid, Locoid C, Maxtrex, Methotrexate, Methotrexate sodium, Modrasone, Mometasone, Nasofan, Neoral, Neotigason, Nizoral, Pimecrolimus, Protopic, Raptiva, Remicade, Silkis, Tacrolimus monohydrate, Tazarotene, Timodine, Tri-Adcortyl, Triamcinolone acetonide, Trimovate, Vioform-Hydrocortisone and Zorac.

Any of the compounds described herein for combination or alternation therapy can be administered as any prodrug that upon administration to the recipient, is capable of providing directly or indirectly, the parent compound. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound.

General Synthesis

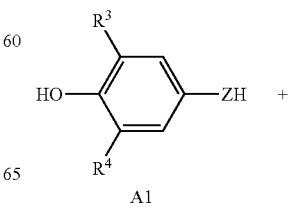

Scheme A

A1

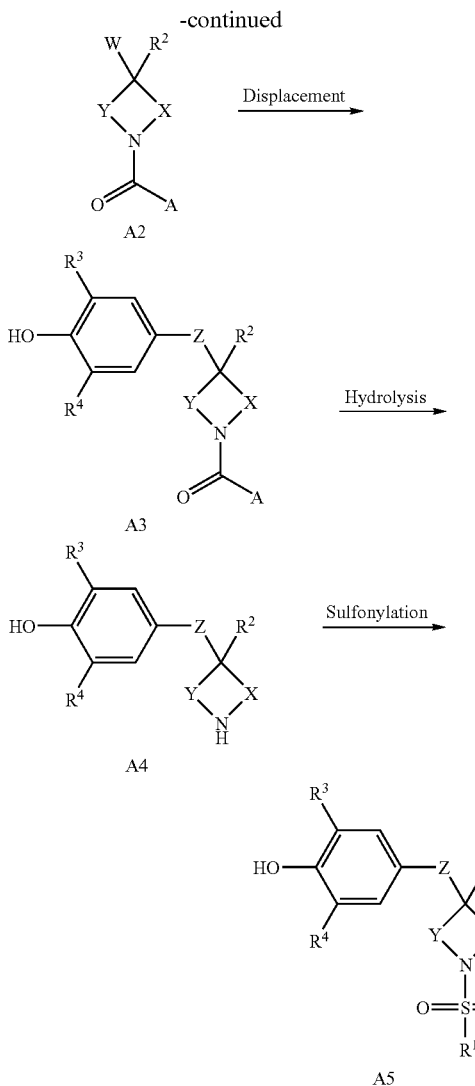

A = $R^5$ or $OR^5$
W = a leaving group such as halide or sulfonate
Z = S or Se

Step 1: A substituted phenol (A1, Z=S or Se), for example 2,6-di-tert-butyl-4-mercaptophenol, is reacted with a nitrogen-containing heterocycle (A2), where W is a suitable leaving group such as mesylate, tosylate, chloride, bromide, iodide, and the like. This displacement reaction is usually performed in a polar, aprotic solvent such as DMF, DMSO, methyl ethyl ketone, acetone, NMP, acetonitrile, THF, and the like, in the presence of an organic base such as diisopropylethylamine, pyridine, potassium tert-butoxide, benzylmagnesium halide, triethylamine, and the like, or an inorganic base such as potassium carbonate, cesium carbonate, sodium carbonate, and the like, at a temperature range of about ambient temperature to 150° C.

Step 2: Hydrolysis of A3 (A=$R^5$ or $OR^5$) can be carried out under basic conditions, for example, by treatment with aqueous solutions of sodium hydroxide or potassium hydroxide in an alcoholic solvent such as 2-methoxyethanol, ethanol, methanol, and the like, at a temperature range of about ambient temperature to 150° C. Alternatively, when A=$OR^5$ and $R^5$=tert-butyl, the hydrolysis can be carried out under acidic conditions, for example, by treatment with hydrogen chloride or trifluoroacetic acid in an ethereal solvent such as diethyl ether, 1,4-dioxane, and the like, or an organic solvent such as dichloromethane, acetonitrile, and the like.

Step 3: Sulfonylation of A4 can be carried out under basic conditions, for example, by treatment with a sulfonyl halide, preferably chloride, in the presence of an organic base such as diisopropylethylamine, pyridine, potassium tert-butoxide, benzylmagnesium halide, triethylamine, and the like, or an inorganic base such as potassium carbonate, cesium carbonate, or sodium carbonate. Common solvents that may be used for sulfonylation include THF, 1,4-dioxane, dichloromethane, toluene, and DMF.

Furthermore, hydrolysis of ester substituents on $R^1$ can be carried out under basic conditions, for example, by treatment with aqueous solutions of sodium hydroxide or potassium hydroxide in an alcoholic solvent such as 2-methoxyethanol, ethanol, or methanol, or an ethereal solvent such as THF, 1,4-dioxane, and the like, at a temperature range of about ambient temperature to 150° C.

Furthermore, reduction of ester substituents on $R^1$ can be carried out under reductive conditions, for example, by treatment with lithium aluminum hydride in an ethereal solvent such as THF or diethylether at a temperature range of about 0° C. to 70° C., or sodium borohydride in an alcoholic solvent such as ethanol, methanol, and the like, at a temperature range of about ambient temperature to 80° C.

Furthermore, addition of alkyl groups to the ester substituent on $R^1$ can be carried out to make the corresponding ketones or tertiary alcohols, for example, by treatment with an alkyl magnesium halide, where the halide is chloride, bromide, iodide or by treatment with an alkyl lithium reagent in an ethereal solvent such as THF, diethylether, and the like, at a temperature range of about 0° C. to 70° C.

Scheme B

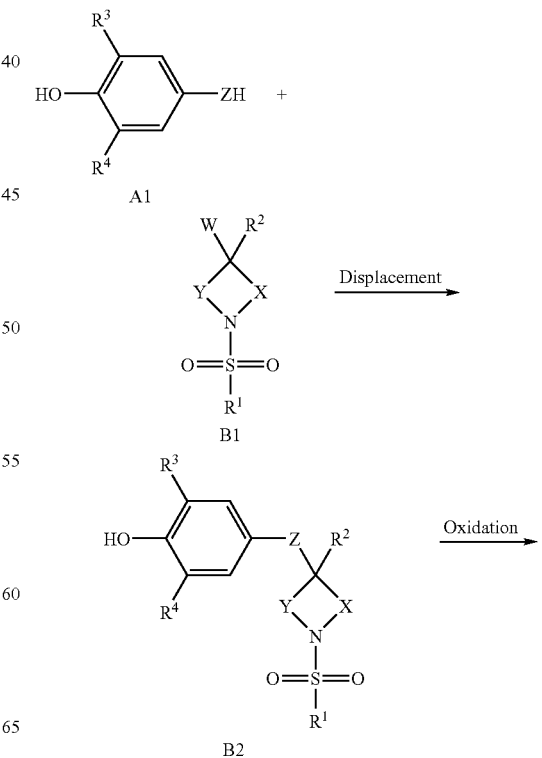

-continued

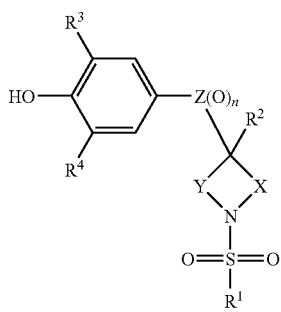

B3

(W = leaving group such as halide or sulfonate; n = 1 or 2)

Step 1: A substituted phenol (A1, Z=S or Se), for example 2,6-di-tert-butyl-4-mercaptophenol, is reacted with a nitrogen-containing heterocycle (B1), where W is a suitable leaving group such as mesylate, tosylate, chloride, bromide, or iodide. This displacement reaction is usually performed in a polar, aprotic solvent such as DMF, DMSO, methyl ethyl ketone, acetone, NMP, acetonitrile, or THF, in the presence of an organic base such as diisopropylethylamine, pyridine, potassium tert-butoxide, benzylmagnesium halide, or triethylamine, or an inorganic base such as potassium carbonate, cesium carbonate, or sodium carbonate at a temperature range between ambient temperature and 80° C.

Step 2: Oxidation of B2 can be carried out under oxidizing conditions, for example, by treatment with aqueous solutions of hydrogen peroxide or m-chloroper-benzoic acid (mCPBA) in dichloromethane or acetonitrile at a temperature range from 0° C. to ambient temperature.

Scheme C

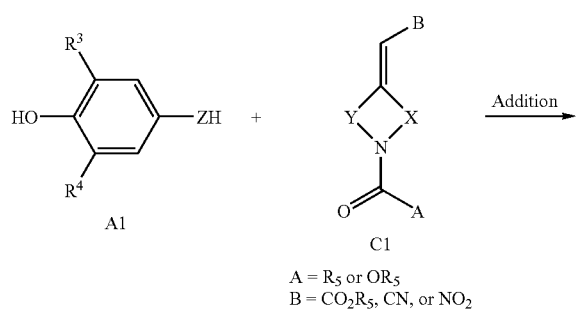

A = R$_5$ or OR$_5$
B = CO$_2$R$_5$, CN, or NO$_2$

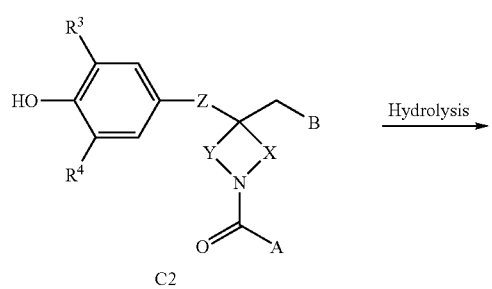

C2

-continued

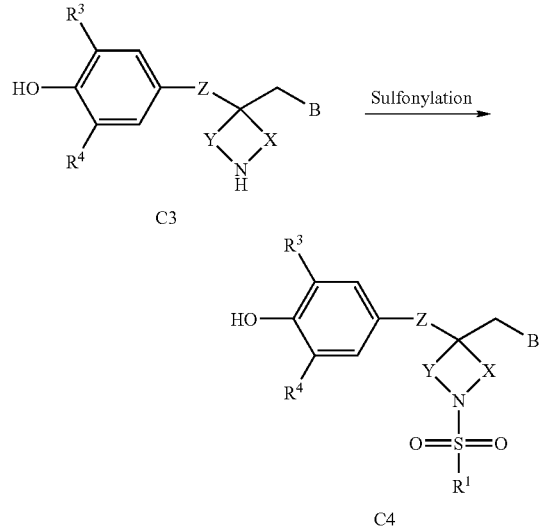

Step 1: A substituted phenol (A1, Z=S or Se), for example 2,6-di-tert-butyl-4-mercaptophenol, is reacted with a nitrogen-containing heterocycle (C1, A=OR$^5$), containing an α,β-unsaturated ester, nitrile or similar electron-withdrawing group, B, in an high boiling non-polar solvent such as toluene or xylenes at a temperature range of ambient temperature to 130° C.

Step 2: Hydrolysis of C2 (A=tert-BuO—) can be carried out under acidic conditions, for example, by treatment with hydrogen chloride or trifluoroacetic acid in an ethereal solvent such as diethyl ether or 1,4-dioxane, or an organic solvent such as dichloromethane or acetonitrile. Alternatively, hydrolysis of C2 (A=OR$^5$ or R$^5$) can be carried out under basic conditions, for example, by treatment with aqueous solutions of sodium hydroxide or potassium hydroxide in an alcoholic solvent such as 2-methoxyethanol, ethanol, or methanol, or an ethereal solvent such as THF or 1,4-dioxane at a temperature range from ambient temperature to 150° C. The proper choice of conditions would depend on the stability of B under such conditions as understood by one ordinarily skilled in the art.

Step 3: Sulfonylation of C3 can be carried out under basic conditions, for example, by treatment with a sulfonyl halide, preferably chloride, in the presence of an organic base such as diisopropylethylamine, pyridine, potassium tert-butoxide, benzylmagnesium halide, or triethylamine, or an inorganic base such as potassium carbonate, cesium carbonate, or sodium carbonate. Common solvents that may be used for sulfonylation include THF, 1,4-dioxane, dichloromethane, toluene, and DMF.

Furthermore, hydrolysis of C4 (B=CO$_2$R$^5$) can be carried out under basic conditions, for example, by treatment with aqueous solutions of sodium hydroxide or potassium hydroxide in an alcoholic solvent such as 2-methoxyethanol, ethanol, or methanol, or an ethereal solvent such as THF or 1,4-dioxane at a temperature range from ambient temperature to 150° C.

Furthermore, reduction of C4 (B=CN or NO$_2$) can be carried out under reductive conditions, for example, by treatment with lithium aluminum hydride in an ethereal solvent such as THF or diethylether, or sodium borohydride in an alcoholic solvent such as ethanol or methanol at ambient temperature to 80° C. Alternatively, hydrogenation conditions may also be utilized, employing a metal catalyst, such as Pd on carbon, Raney-Ni, or Pt on carbon in a solvent such as ethanol, ethyl acetate, or THF, under hydrogen gas.

Scheme D

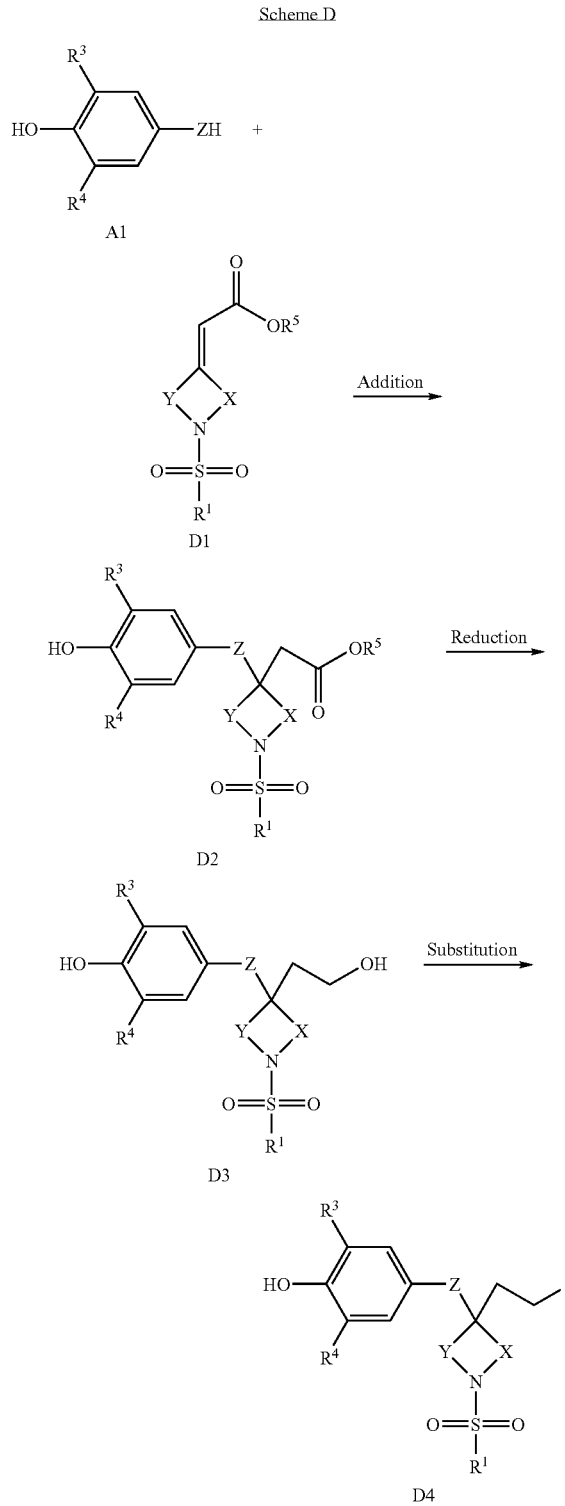

Step 1: A substituted phenol (A1, Z=S or Se), for example 2,6-di-tert-butyl-4-mercaptophenol, is reacted with a nitrogen-containing heterocycle (D1), containing an α,β-unsatur-ated ester in an high boiling non-polar solvent such as toluene or xylenes at a temperature range of ambient temperature to 130° C.

Step 2: The product, D2, can be converted to the corresponding alcohol under reductive conditions, for example, by treatment with lithium aluminum hydride in an ethereal solvent such as THF or diethylether, or sodium borohydride in an alcoholic solvent such as ethanol or methanol at 0° C. to 80° C.

Alternatively, D2 can be converted to a tertiary alcohol by treatment with an alkyl magnesium halide, where the halide is chloride, bromide, iodide or by treatment with an alkyl lithium reagent in an ethereal solvent such as THF, diethylether, and the like, at a temperature range of about 0° C. to 70° C.

Step 3: Replacement of the alcohol with $R^6$ can be carried out in a 2-step sequence, consisting of converting the alcohol to a suitable leaving group such as a mesylate, tosylate, chloride, bromide, or iodide, followed by displacement with an $R^6$ nucleophile under basic conditions. This displacement reaction is usually performed in a polar, aprotic solvent such as DMF, DMSO, methyl ethyl ketone, acetone, NMP, acetonitrile, or THF, in the presence of an organic base such as diisopropylethylamine, pyridine, potassium tert-butoxide, benzylmagnesium halide, or triethylamine, or an inorganic base such as potassium carbonate, cesium carbonate, or sodium carbonate at a temperature range between ambient temperature and 150° C. Alternatively, the alcohol may be substituted with an $R^6$ nucleophile under near neutral Mitsunobu conditions, for example, using diethylazodicarboxylate or diisopropylazodicarboxylate in an aprotic solvent such as THF, methylene chloride, or toluene at a temperature range from ambient temperature to 110° C.

EXAMPLES

Example 1

5-[4-(3,5-Di-tert-butyl-4-hydroxy-phenylsulfanyl)-4-(2-hydroxy-ethyl)-piperidine-1-sulfonyl]-1-methyl-1H-pyrrole-2-carboxylic acid

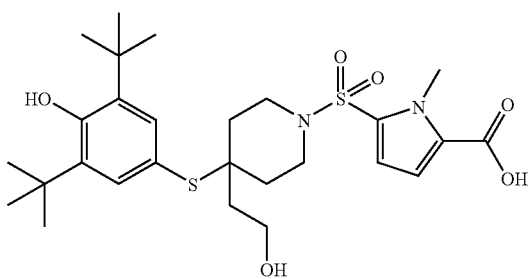

Ex. 1a

A suspension of 2,6-di-tert-butyl-4-mercapto-phenol (1.2 g, 5.2 mmol) and 4-ethoxycarbonylmethylene-piperidine-1-carboxylic acid tert-butyl ester (1.2 g, 4.4 mmol) in 5 mL of piperidine was degassed and then heated to 90° C. for 15 h. The reaction was cooled to room temperature, toluene (10 mL) was added, and the mixture was concentrated under reduced pressure. The residue obtained was diluted with ethyl acetate (40 mL), washed with 1 N HCl (2×30 mL) and water (40 mL), dried over Na$_2$SO$_4$, and concentrated under reduced pressure. Chromatography (2-20% ethyl acetate/hexanes) afforded 4-(3,5-di-tert-butyl-4-hydroxy-phenylsulfanyl)-4-ethoxycarbonylmethyl-piperidine-1-carboxylic acid tert-butyl ester as a foamy solid (2.1 g, 94%). ESI/CI-MS m/z 506 ([M−H]$^-$).

Ex. 1b

To 4-(3,5-di-tert-butyl-4-hydroxy-phenylsulfanyl)-4-ethoxycarbonylmethyl-piperidine-1-carboxylic acid tert-butyl ester (Ex. 1a, 510 mg, 1 mmol) in 4 mL of THF was added dropwise 1 M LiAlH$_4$ solution (4 mL, 4 mmol) over a period of 15 min. The reaction was stirred for 1 h and then quenched with saturated NH$_4$Cl solution (30 mL). The mixture was extracted with Ethyl acetate (40+20 mL) and the combined organic phase was dried over Na$_2$SO$_4$ and concentrated under reduced pressure. The residue was dissolved in 8 mL of dichloromethane. Triethylamine (300 mg, 2.9 mmol) and DMAP (10 mg) were added followed by dropwise addition of Ac$_2$O (205 mg, 2 mmol). The reaction mixture was stirred for 3 h and then diluted with Ethyl acetate (40 mL). The mixture was washed with 1 N HCl (2×30 mL) and water (50 mL) and dried over Na$_2$SO$_4$. Chromatography (2-20% Ethyl acetate/hexanes) afforded 4-(2-acetoxy-ethyl)-4-(3,5-di-tert-butyl-4-hydroxy-phenylsulfanyl)-piperidine-1-carboxylic acid tert-butyl ester as a clear oil (420 mg, 82%). ESI/CI-MS m/z 506 ([M−H]$^-$).

Ex. 1c

To 4-(2-acetoxy-ethyl)-4-(3,5-di-tert-butyl-4-hydroxy-phenylsulfanyl)-piperidine-1-carboxylic acid tert-butyl ester (Ex. 1b, 420 mg) was added 5 mL of 4 N HCl in dioxane. The mixture was stirred for 3 h and then concentrated under reduced pressure. The resulting solid was washed with Ethyl acetate/hexanes (1:3, 20 mL) and dried under high vacuum to afford acetic acid 2-[4-(3,5-di-tert-butyl-4-hydroxy-phenylsulfanyl)-piperidin-4-yl]-ethyl ester hydrochloride as a white solid (370 mg, 100%). ESI/CI-MS m/z 408 ([M+H]$^+$).

Ex. 1d

To acetic acid 2-[4-(3,5-di-tert-butyl-4-hydroxy-phenylsulfanyl)-piperidin-4-yl]-ethyl ester hydrochloride (Ex. 1c, 370 mg, 0.83 mmol) in 8 mL of dichloromethane was added triethylamine (293 mg, 2.9 mmol). After stirring for 5 min, 5-chlorosulfonyl-1-methyl-1H-pyrrole-2-carboxylic acid methyl ester (296 mg, 1.25 mmol) was added in 3 portions. The reaction mixture was stirred for 3 h at room temperature, and then diluted with Ethyl acetate (40 mL), washed with water (50 mL), 0.5 N HCl (2×30 mL) and water (50 mL), dried over Na$_2$SO$_4$, and concentrated under reduced pressure. The crude product was chromatographed with 5-30% Ethyl acetate/hexanes to afford 5-[4-(2-acetoxy-ethyl)-4-(3,5-di-tert-butyl-4-hydroxy-phenylsulfanyl)-piperidine-1-sulfonyl]-1-methyl-1H-pyrrole-2-carboxylic acid methyl ester as a clear oil (420 mg, 83%). ESI/CI-MS m/z 609 ([M+H]$^+$).

To 5-[4-(2-acetoxy-ethyl)-4-(3,5-di-tert-butyl-4-hydroxy-phenylsulfanyl)-piperidine-1-sulfonyl]-1-methyl-1H-pyrrole-2-carboxylic acid methyl ester (Ex. 1d, 420 mg, 0.69 mmol) in 4 mL of methanol was added a NaOH solution (220 mg in 3.5 mL of water). The mixture was stirred for 15 h at room temperature and then quenched with a mixture of 9 mL of 1 N HCl and 30 g of ice. It was extracted with Ethyl acetate (40+20 mL) and the combined organic phase was dried over Na$_2$SO$_4$ and concentrated under reduced pressure. The crude product was chromatographed with 1-10% Methanol in dichloromethane to afford the title compound as a white solid (240 mg, 63%), mp 183-184° C. $^1$H NMR (400 MHz, CDCl$_3$): δ 7.17 (d, J=2.0 Hz, 1H), 7.12 (d, J=2.0 Hz, 1H), 7.20 (s, 2H), 5.38 (s, 1H), 4.00 (s, 3H), 3.98 (t, J=6.4 Hz, 2H), 3.32 (m, 2H), 3.09 (m, 2H), 1.75-1.67 (m, 6H); ESI/CI-MS m/z 553 ([M+H]$^+$), 551 ([M−H]$^-$). Anal. calcd for C$_{27}$H$_{40}$N$_2$O$_6$S$_2$: C, 58.67; H, 7.29; N, 5.07. Found: C, 58.03, H, 7.31; N, 4.91.

Example 2

2,6-Di-tert-butyl-4-[4-(2-hydroxy-ethyl)-1-(5-hydroxymethyl-1-methyl-1H-pyrrole-2-sulfonyl)-piperidin-4-ylsulfanyl]-phenol

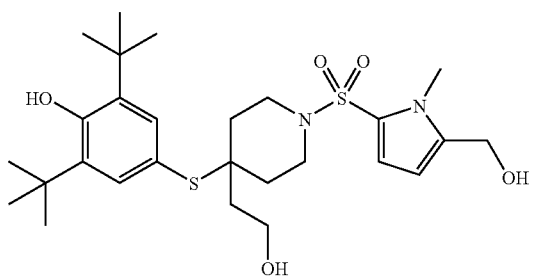

To 5-[4-(2-acetoxy-ethyl)-4-(3,5-di-tert-butyl-4-hydroxy-phenylsulfanyl)-piperidine-1-sulfonyl]-1-methyl-1H-pyrrole-2-carboxylic acid methyl ester (Ex. 1d, 460 mg, 0.75 mmol) in 4 mL of THF was added dropwise 3 mL of a 1 M LiAlH$_4$ in THF. The mixture was stirred for 2 h and then quenched with saturated aqueous NaH$_2$PO$_4$ (20 mL). It was diluted with Ethyl acetate (30 mL), stirred for 10 min, and then let sit for 1 h. The layers were separated and the aqueous layer was extracted with Ethyl acetate (20 mL). The combined organic layers were washed with water (50 mL), dried over Na$_2$SO$_4$, and concentrated under reduced pressure. The crude product was chromatographed with 10-85% Ethyl acetate/hexanes to afford the title compound as a white solid (305 mg, 75%), mp 126-127° C. $^1$H NMR (400 MHz, CD$_3$OD): δ 7.26 (d, J=2.0 Hz, 1H), 7.15 (s, 2H), 6.34 (d, J=2.0 Hz, 1H), 4.57 (s, 2H), 3.88 (t, J=7.2 Hz, 2H), 3.76 (s, 3H), 3.26 (1H), 3.02 (td, J=7.2, 2.4 Hz, 2H), 1.75-1.68 (m, 2H), 1.64-1.58 (m, 4H), 1.39 (s, 3H); ESI/CI-MS m/z 539 ([M+H]$^+$), 537 ([M−H]$^-$). Anal. calcd for C$_{27}$H$_{42}$N$_2$O$_5$S$_2$: C, 60.19; H, 7.86; N, 5.20. Found: C, 60.28, H, 7.93; N, 5.13.

Example 3

4-[4-(3,5-Di-tert-butyl-4-hydroxy-phenylsulfanyl)-piperidine-1-sulfonyl]-3,5-dimethyl-1H-pyrrole-2-carboxylic acid

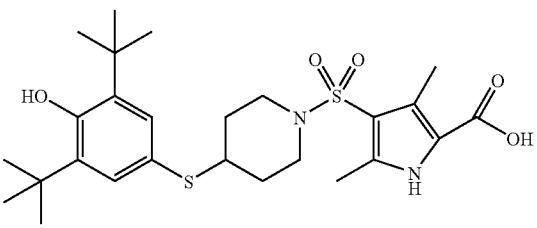

Ex. 3a

To a solution of 4-hydroxy-piperidine-1-carboxylic acid tert-butyl ester (40 g, 0.20 moles) in dichloromethane (800 mL) was added triethylamine (83.1 mL, 0.60 moles). The reaction was cooled to 0° C. Methanesulfonyl chloride (23.1 mL, 0.30 moles) was added slowly over 15 minutes and the reaction was stirred at 0° C. for 30 minutes and then at room temperature for 16 hours. The reaction was quenched with $H_2O$ (500 mL) and the layers were cut. The organic layer was washed with $H_2O$ (2×500 mL), 1N HCl (3×500 mL) and $H_2O$ (1×500 mL). The organic layer was dried over $Na_2SO_4$ (40 g) and concentrated under reduced pressure. Ethyl acetate (50 mL) was added to the oil, followed by 350 mL of hexanes. After 3 hours, the solid was filtered and dried in a vacuum oven to afford 44.42 g (80.0%) of 4-(methanesulfonyloxy)-piperidine-1-carboxylic acid tert-butyl ester as a pale yellow solid, mp 84-86° C. $^1$H-NMR (400 MHz, $CDCl_3$): δ 4.90-4.86 (m, 1H), 3.74-3.67 (m, 2H), 3.32-3.27 (m, 2H), 3.04 (s, 3H), 2.00-1.93 (m, 2H), 1.86-1.77 (m, 2H), 1.46 (s, 9H). HRMS (ESI) Calcd. for $C_{11}H_{21}NO_5S$, 279.1140 ($M^+$). Found: 279.1141. Anal. Calcd. for $C_{11}H_{21}NO_5S$, C, 47.29; H, 7.58; N, 5.01; S, 11.48. Found: C, 47.49; H, 7.52; N, 5.06; S, 11.61.

Ex. 3b

To 4-methanesulfonyloxy-piperidine-1-carboxylic acid tert-butyl ester (Ex. 3a, 22 g) and 2,6-di-tert-butyl-4-mercapto-phenol (16.58 g) in 300 mL of DMF was added sodium hydride (3.8 g, 60% in oil). The mixture was stirred at 60° C. for 20 h and then poured onto ice and quenched with 1 N HCl. The gooey solid obtained via filtration was dissolved in Ethyl acetate, dried over $Na_2SO_4$, and concentrated. The crude product was dissolved in a minimal amount of diethyl ether and triturated with hexanes to give 4-(3,5-di-tert-butyl-4-hydroxy-phenylsulfanyl)-piperidine-1-carboxylic acid tert-butyl ester as an off-white solid (16 g), mp 151-152° C. $^1$H-NMR (400 MHz, $CDCl_3$): δ 7.28 (s, 2H), 5.28 (s, 1H), 3.98 (s, 2H), 3.03-2.96 (m, 1H), 2.87 (t, 2H, J=10.4 Hz), 1.91-1.87 (m, 2H), 1.54-1.48 (m, 2H), 1.44 (s, 9H), 1.43 (s, 18H). HRMS (ESI) Calcd. for $C_{24}H_{39}NO_3S$: 421.2651 ($M^+$). Found: 421.2656. Anal. Calcd. for $C_{24}H_{39}NO_3S$, C, 68.37; H, 9.32; N, 3.32; S, 7.60. Found: C, 68.20; H, 9.42; N, 3.23; S, 7.77.

Ex. 3c

To 4-(3,5-di-tert-butyl-4-hydroxy-phenylsulfanyl)-piperidine-1-carboxylic acid tert-butyl ester (Ex. 3b, 21 g, 50 mmol) in a 250 mL round bottom flask was added 100 mL of a 4 N HCl in dioxane. The mixture was stirred at room temperature for 5 h and concentrated under reduced pressure to about 25 mL. The solid was collected through filtration, washed with Ethyl acetate/hexanes (1:2 v/v, 50 mL), and dried under high vacuum to afford 2,6-di-tert-butyl-4-(piperidin-4-ylsulfanyl)-phenol hydrochloride as a white solid (16 g, 97%). $^1$H NMR (400 MHz, $CD_3OD$): δ 7.26 (s, 2H), 3.35 (m, 2H), 3.10 (m, 1H), 3.00 (m, 2H), 2.11 (m, 2H), 1.68 (m, 2H), 1.37 (s, 18H). ESI/CI-MS m/z 322 ($[M+H]^+$), 320 ($[M-H]^-$). HRMS (ESI) Calcd. for $C_{19}H_{32}ClNOS$: 321.2126 ($M^+$). Found: 321.2127. Anal. Calcd. for $C_{19}H_{32}ClNOS$, C, 63.75; H, 9.01; N, 3.91; S, 8.96. Found: C, 63.43; H, 9.08; N, 3.94; S, 8.72.

Ex. 3d

To a solution of 4-methanesulfonyloxy-piperidine-1-carboxylic acid tert-butyl ester (Ex. 3a, 35.5 g, 0.13 moles) in degassed 2-butanone (400 mL) were added 2,6-di-tert-butyl-4-mercapto-phenol (37.9 g, 0.16 moles) and cesium carbonate (62.7 g, 0.19 moles). The resulting solution was heated to 60° C. and stirred for 8 hours. Upon completion, as determined by HPLC, the reaction was diluted with 400 mL water and 500 mL ethyl acetate. The layers were cut and the organic layer was washed with saturated ammonium chloride solution (400 mL) and brine (400 mL). The volume was then concentrated under reduced pressure to 250 mL. 1,4-Dioxane (300 mL) was added, and then concentrated under reduced pressure to 100 mL. 1,4-Dioxane (300 mL) was added again. HCl (4.0 M in dioxane, 195 mL, 0.7 moles) was added slowly over 30 minutes, and the reaction was stirred at room temperature for 16 hours. The solution was concentrated under reduced pressure to 100 mL, and 1:3 solution of ethyl acetate:hexanes (250 mL) was added while stirring. After 3 hours, the solid was filtered and rinsed with a 1:9 solution of Ethyl acetate:hexanes (80 mL). The wet cake was allowed to air dry, and the solid were added to 120 mL of ethyl acetate and 120 mL of water. A 5.0 N solution of NaOH (28 mL, 0.14 moles) was added to the solution and the reaction was stirred for 30 minutes. The layers were cut. The organic layer was washed with a 6% brine solution (2×100 mL). The solution was concentrated under reduced pressure, and hexanes (70 mL) was added. The mixture was stirred for 16 hours at room temperature, then cooled to −5° C. and stirred for another hour. The solution was filtered and the solid was rinsed with cold hexanes (15 mL) and dried in a vacuum oven for 16 hours, affording 29.5 g (72.2%) of 2,6-di-tert-butyl-4-(piperidin-4-ylsulfanyl)-phenol as a white solid, mp 113-114° C. $^1$H-NMR (400 MHz, $CDCl_3$): δ7.28 (s, 2H), 5.27 (s, 1H), 3.14-3.09 (m, 2H), 2.98-2.91 (m, 1H), 2.66-2.59 (m, 2H), 1.96-1.92 (m, 2H), 1.51-1.47 (m, 2H), 1.44 (s, 18H). HRMS (ESI) Calcd. for $C_{19}H_{31}NOS$: 322.2204 ($[M+H]^+$). Found: 322.2196. Anal. Calcd. for $C_{19}H_{31}NOS$, C, 70.98; H, 9.72; N, 4.36; S, 9.97. Found: C, 70.87; H, 9.76; N, 4.30; S, 9.93.

Ex. 3e

To 2,6-di-tert-butyl-4-(piperidin-4-ylsulfanyl)-phenol hydrochloride (Ex. 3c, 500 mg, 1.4 mmol) in 5 mL of dichloromethane was added triethylamine (495 mg, 4.9 mmol). The mixture was stirred for 3 min followed by the addition of 4-chlorosulfonyl-3,5-dimethyl-1H-pyrrole-2-carboxylic acid ethyl ester (446 mg, 1.68 mmol). The stirring was continued for 3 h at room temperature. The reaction mixture was diluted with Ethyl acetate/hexanes (15 mL, 1:1 v/v), and washed with water (2×20 mL), 0.5 M HCl (2×20 mL) and water (40 mL). It was dried over $Na_2SO_4$ and concentrated under reduced pressure to give a brown oil. Chromatography (5-40% Ethyl acetate/hexanes) gave 4-[4-(3,5-di-tert-butyl-4-hydroxy-phenylsulfanyl)-piperidine-1-sulfonyl]-3,5-dimethyl-1H-pyrrole-2-carboxylic acid ethyl ester as a light-pink foamy solid (620 mg, 80%). ESI/CI-MS m/z 551 ($[M+H]^+$), 549 ($[M-H]^-$).

To 4-[4-(3,5-di-tert-butyl-4-hydroxy-phenylsulfanyl)-piperidine-1-sulfonyl]-3,5-di-methyl-1H-pyrrole-2-carboxylic acid ethyl ester (Ex. 3e, 620 mg, 1.1 mmol) in 3 mL of Methanol and 3 mL of THF was added a suspension of LiOH (134 mg, 5.6 mmol) in 1.5 mL of water. The resulting suspension was stirred at room temperature for 18 h and the reaction was quenched with saturated $NH_4Cl$. To the mixture was added 0.5 N HCl to adjust the pH to about 4. It was extracted with Ethyl acetate (3×30 mL) and the combined organic extracts were dried over $Na_2SO_4$ and concentrated under reduced pressure. Chromatography (1-12% Methanol/dichloromethane) gave the title compound as a light-pink solid (358 mg, 61%), mp 124-125° C. $^1$H NMR (400 MHz, $CDCl_3$): δ 0.94 (bs, 1H), 7.23 (s, 2H), 5.27 (s, 1H), 3.59 (m, 2H), 2.83 (m, 1H), 2.64 (m, 2H), 2.499 (s, 3H), 2.496 (s, 3H), 1.97 (m, 2H), 1.63 (m, 2H), 1.38 (s, 18H). ESI/CI-MS m/z 322 ([M+H]$^+$), 320 ([M–H]$^-$). HR-MS (ESI) calcd for $C_{26}H_{38}N_2O_5S_2$, 523.2300 ([M+H]$^+$). Found: 523.2301. Two HPLC (reverse-phase, $C_{18}$) methods were used to determine the purity of the title compound. Method 1: gradient elution, 50% to 99% solvent B (A=aqueous 0.1% $H_3PO_4$, B=MeCN) in 15 min. Purity (UV-VIS): 97.9% (215 nm), 97.5% (254 nm); Method 2: gradient elution, 40% to 95% solvent B (A=10 mM $NH_4OAc$, B=MeCN) in 6 min. Purity (UV-VIS λ): 97.9% (215 nm), 97.9% (254 nm), 97.5% (280 nm).

Example 4

5-[4-(3,5-Di-tert-butyl-4-hydroxy-phenylsulfanyl)-piperidine-1-sulfonyl]-1-methyl-1H-pyrrole-2-carboxylic acid

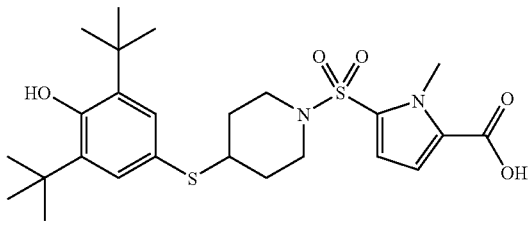

Ex. 4a

To a solution of 2,6-di-tert-butyl-4-(piperidin-4-ylsulfanyl)-phenol hydrochloride (Ex. 3c, 5.4 g) in 44 mL of THF at room temperature was added N,N-diisopropylethylamine (8.8 mL), followed by 5-chlorosulfonyl-1-methyl-1H-pyrrole-2-carboxylic acid methyl ester (4 g). The mixture was stirred at room temperature for 18 h and then diluted with ethyl acetate and washed twice with 1 N HCl (aq), and once with brine. After concentration of the organic extracts, the crude solid was triturated with 15% ethyl acetate in hexanes to give 4.5 g of 5-[4-(3,5-di-tert-butyl-4-hydroxy-phenylsulfanyl)-piperidine-1-sulfonyl]-1-methyl-1H-pyrrole-2-carboxylic acid methyl ester as an off-white solid, mp 181-183° C. $^1$H-NMR (300 MHz, CDCl$_3$): δ 7.23 (s, 2H), 7.17 (d, 1H, J=1.5 Hz), 7.09 (d, 1H, J=1.2 Hz), 5.30 (s, 1H), 3.96 (s, 3H), 3.83 (s, 3H), 3.60-3.54 (m, 2H), 2.80-2.74 (m, 1H), 2.54-2.45 (m, 2H), 2.03-1.97 (m, 2H), 1.73-1.67 (m, 2H), 1.41 (s, 18H).

Alternatively, to a solution of 2,6-di-tert-butyl-4-(piperidin-4-ylsulfanyl)-phenol (Ex. 3d, 48.0 g, 0.15 moles) in THF (1000 mL) was added diisopropylethyl amine (39.0 mL, 0.22 moles) and methyl-5-(chlorosulfonyl)-1-methyl-1H-pyrrole-2-carboxylate (35.5 g, 0.15 moles) and the resulting solution was stirred at room temperature for 5 hours. Upon completion, as determined by HPLC, the reaction was diluted with ethyl acetate (500 mL) and water (500 mL). The layers were cut and the organic layer was washed with 1N HCl (500 mL) and 6% brine (2×500 mL), and concentrated under reduced pressure to afford 77.2 g (98.8%) of 5-[4-(3,5-di-tert-butyl-4-hydroxy-phenylsulfanyl)-piperidine-1-sulfonyl]-1-methyl-1H-pyrrole-2-carboxylic acid methyl ester as a white solid, mp 185-187° C. $^1$H-NMR (400 MHz, CDCl$_3$): δ 7.23 (s, 2H), 7.17 (d, 1H, J=1.6 Hz), 7.09 (d, 1H, J=2.0 Hz), 5.29 (s, 1H), 3.96 (s, 3H), 3.84 (s, 3H), 3.57 (m, 2H), 2.79 (m, 1H), 2.50 (m, 2H), 1.99 (m, 2H), 1.70 (m, 2H), 1.42 (s, 18H). HRMS (ESI) Calcd. for $C_{26}H_{38}N_2O_5S_2$, 522.2222 (M$^+$). Found: 522.2228. Anal. Calcd. for $C_{26}H_{38}N_2O_5S_2$: C, 59.74; H, 7.33; N, 5.36; S, 12.27. Found: C, 59.48; H, 7.50; N, 5.22; S, 12.05.

To 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 4.45 g) in 60 mL of THF and 15 mL of H$_2$O was added LiOH monohydrate (1.8 g). The mixture was stirred at room temperature for 18 h and then diluted with H$_2$O and washed with Et$_2$O to remove unreacted starting material. The aqueous layer was acidified to pH 2 with 1N HCl and extracted with ethyl acetate. The organic extracts were dried over Na$_2$SO$_4$, filtered, and concentrated to give a reddish oil. Flash chromatography with a 120 g Isco column (3.5% Methanol in dichloromethane) afforded 2.15 g of the title compound as an orange colored solid, mp 192-194° C. $^1$H NMR (300 MHz, CDCl$_3$): δ 7.24 (s, 2H), 7.23 (s, 1H), 7.22 (s, 1H), 5.30 (s, 1H), 3.96 (s, 3H), 3.59-3.57 (m, 2H), 2.83-2.78 (m, 1H), 2.54-2.50 (m, 2H), 2.02-1.99 (m, 2H), 1.75-1.68 (m, 2H), 1.39 (s, 18H). HRMS (ESI) Calcd. for $C_{25}H_{36}N_2O_5S_2$, 509.2144 ([M+H]$^+$). Found: 509.2140.

Alternatively, to a solution of 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 72.0 g, 0.14 moles) in THF (1200 mL), Methanol (400 mL) and H$_2$O (400 mL) was added lithium hydroxide (16.5 g, 0.69 moles) and the resulting solution was stirred at room temperature for 3 hours. Upon completion, as determined by HPLC, the reaction was diluted with ethyl acetate (2000 mL) and 1 N HCl (2000 mL). The layers were cut, and the organic layer was washed with 6% brine (2×2000 mL). The organic layer was concentrated under reduced pressure and ethyl acetate (50 mL) and hexanes (600 mL) were added. The mixture was stirred for 30 minutes and then filtered. The solid was rinsed with cold hexanes (50 mL) and the solid was dried in a vacuum oven for 72 hours at 90° C. to afford 67.0 g (95.7%) of the title compound as a white solid, mp 192-194° C. $^1$H-NMR (400 MHz, CDCl$_3$): δ 7.24 (s, 2H), 7.23 (s, 1H), 7.22 (s, 1H), 5.30 (s, 1H), 3.97 (s, 3H), 3.58 (m, 2H), 2.80 (m, 1H), 2.53 (m, 2H), 2.00 (m, 2H), 1.73 (m, 2H), 1.42 (s, 18H). HRMS (ESI) Calcd. for $C_{25}H_{36}N_2O_5S_2$, 509.2144 ([M+H]$^+$). Found: 509.2144. Anal. Calcd. for $C_{25}H_{36}N_2O_5S_2$: C, 59.03; H, 7.13; N, 5.51; S, 12.61. Found: C, 58.56; H, 7.17; N, 5.42; S, 12.50.

Example 5

2,6-Di-tert-butyl-4-[1-(5-hydroxymethyl-1-methyl-1H-pyrrole-2-sulfonyl)-piperidin-4-ylsulfanyl]-phenol

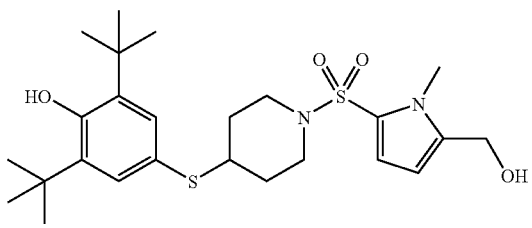

To 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 440 mg, 0.84 mmol) in 5 mL of THF was added LiAlH$_4$ (128 mg, 3.4 mmol) in 4 portions. The mixture was stirred for 2 h at room temperature and then quenched with saturated NH₄Cl (30 mL) and extracted with Ethyl acetate (2×30 mL). The combined organic extracts were dried over Na₂SO₄ and concentrated under reduced pressure. Chromatography (10-60% Ethyl acetate/hexanes) gave the title compound as a light-pink solid (195 mg, 47%), mp 64-65° C. ¹H NMR (400 MHz, CDCl₃): δ 7.27 (s, 2H), 7.07 (d, J=2 Hz, 1H), 6.32 (d, J=2 Hz, 1H), 5.30 (s, 1H), 4.59 (s, 2H), 3.73 (s, 3H), 3.57 (m, 2H), 2.77 (m, 1H), 2.48 (m, 2H), 1.99 (m, 2H), 1.70 (m, 2H), 1.41 (s, 18H). ESI/CI-MS m/z 495 ([M+H]⁺), 493 ([M−H]⁻). Three HPLC (reverse-phase, C₁₈) methods were used to determine the purity of the title compound. Method 1: gradient elution, 50% to 99% solvent B (A=aqueous 0.1% H₃PO₄, B=MeCN) in 15 min. Purity (UV-VIS): 98.7% (215 nm), 97.6% (254 nm), 98.6% (280 nm); Method 2: gradient elution, 40% to 95% solvent B (A=10 mM NH₄OAc, B=MeCN) in 6 min. Purity (UV-VIS λ): 98.0% (215 nm), 97.8% (254 nm), 97.8% (280 nm); Method 3: gradient elution, 60% to 85% solvent B (A=aqueous 0.1% H₃PO₄, B=MeCN) in 15 min. Purity (UV-VIS): 98.3% (238 nm).

Example 6

5-{4-[3,5-Di-tert-butyl-4-(3-hydroxy-propoxy)-phenylsulfanyl]-piperidine-1-sulfonyl}-1-methyl-1H-pyrrole-2-carboxylic acid

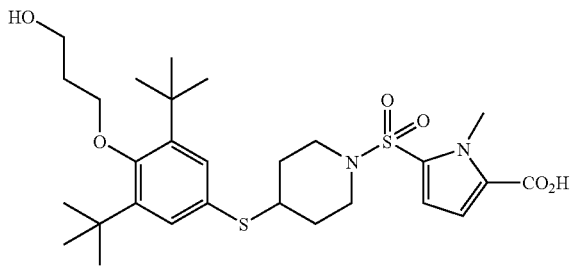

Ex. 6a

To 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 436 mg, 0.83 mmol) in 3 mL of DMF was added 3-bromo-propan-1-ol (127 mg, 0.91 mmol) and K₂CO₃ (343 mg, 2.5 mmol). The mixture was heated to 75° C. for 16 h. Upon cooling to room temperature it was poured into saturated NH₄Cl (30 mL). The mixture was extracted with Ethyl acetate (3×30 mL) and the organic extracts were dried over Na₂SO₄ and concentrated under reduced pressure. Chromatography (3-40% Ethyl acetate/hexanes) gave 5-{4-[3,5-di-tert-butyl-4-(3-hydroxy-propoxy)-phenylsulfanyl]-piperidine-1-sulfonyl}-1-methyl-1H-pyrrole-2-carboxylic acid methyl ester as a pale-yellow thick oil (203 mg). ESI/CI-MS m/z 581 ([M+H]⁺).

To 5-{4-[3,5-di-tert-butyl-4-(3-hydroxy-propoxy)-phenylsulfanyl]-piperidine-1-sulfonyl}-1-methyl-1H-pyrrole-2-carboxylic acid methyl ester (Ex. 6a, 202 mg, 0.35 mmol) in 2 mL of Methanol and 2 mL of THF was added a NaOH solution (70 mg, 1.75 mmol, in 1.2 mL of water). The reaction mixture was stirred at room temperature for 15 h and then quenched with saturated NH₄Cl (30 mL). To the mixture was added 0.5 N HCl to adjust the pH to about 4. It was extracted with Ethyl acetate (3×30 mL). The organic extracts were dried over Na₂SO₄ and concentrated under reduced pressure. Chromatographed (1-7% Methanol/dichloromethane) gave the title compound as a off-white solid (108 mg, 54%), mp 82-84° C. ¹H NMR (400 MHz, CDCl₃): δ 7.27 (m, 2H), 7.23-7.21 (m, 2H), 3.96 (s, 3H), 3.89-3.84 (m, 4H), 3.56 (m, 2H), 2.88 (m, 1H), 2.56 (m, 2H), 2.12 (m, 2H), 2.05-2.00 (m, 2H), 1.71 (m, 2H), 1.39 (s, 18H). ESI/CI-MS m/z 567 ([M+H]⁺), 565 ([M−H]⁻). HR-MS (ESI) calcd for C₂₈H₄₂N₂O₆S₂, 567.2562 ([M+H]⁺). Found 567.2562. Two HPLC (reverse-phase, C₁₈) methods were used to determine the purity of the title compound. Method 1: gradient elution, 50% to 99% solvent B (A=aqueous 0.1% H₃PO₄, B=MeCN) in 15 min. Purity (UV-VIS): 98.6% (215 nm), 97.7% (254 nm), 98.4% (280 nm); Method 2: gradient elution, 40% to 95% solvent B (A=10 mM NH₄OAc, B=MeCN) in 6 min. Purity (UV-VIS λ): 98.6% (215 nm), 97.8% (254 nm), 97.1% (280 nm).

Example 7

5-[4-(3,5-Di-tert-butyl-4-hydroxy-benzenesulfinyl)-piperidine-1-sulfonyl]-1-methyl-1H-pyrrole-2-carboxylic acid

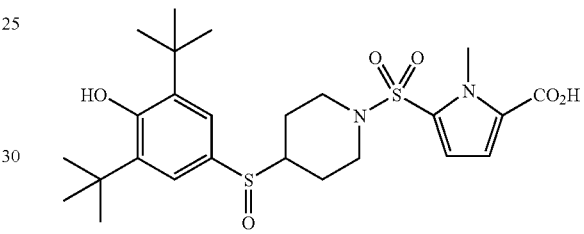

Ex. 7a

To 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 490 mg, 0.94 mmol) in 10 mL of dichloromethane at room temperature under N₂ was added m-chloroperbenzoic acid (247 mg, 1.1 mmol) in 5 portions during a period of 30 min. The resulting suspension was stirred for 3 h at room temperature and then the reaction was quenched by pouring the suspension onto ice (20 g). The mixture was extracted with ethyl acetate (2×40 mL) and the combined organic phase was dried over Na₂SO₄ and concentrated under reduced pressure. Chromatography (3-50% Ethyl acetate/hexanes) gave 5-[4-(3,5-di-tert-butyl-4-hydroxy-benzenesulfinyl)-piperidine-1-sulfonyl]-1-methyl-1H-pyrrole-2-carboxylic acid methyl ester a white solid (480 mg, 95%). ESI/Cl-MS m/z 537 ([M−H]⁻).

To 5-[4-(3,5-di-tert-butyl-4-hydroxy-benzenesulfinyl)-piperidine-1-sulfonyl]-1-methyl-1H-pyrrole-2-carboxylic acid methyl ester (Ex. 7a, 480 mg, 0.89 mmol) in 5 mL of Methanol was added a NaOH solution (142 mg in 2 mL H₂O, 3.6 mmol). The reaction was stirred at room temperature for 5 h and then quenched by pouring the mixture into a mixture of 5 mL of 1 N HCl and 20 g of ice. The resultant mixture was extracted with Ethyl acetate (40 mL+20 mL) and the combined organic phase was dried over Na₂SO₄ and concentrated under reduced pressure. Chromatography (1-5% Methanol/dichloromethane) gave the title compound as a white solid (382 mg, 82%), mp 134-135° C. ¹H NMR (400 MHz, CDCl₃): δ 7.41 (s, 2H), 7.17 (d, J=1.8 Hz, 1H), 7.12 (d, J=1.8 Hz, 1H), 5.67 (s, 1H), 3.92 (s, 3H), 3.83-3.71 (m, 2H), 2.76 (m, 1H), 2.39-2.31 (m, 2H), 2.20-2.17 (m, 1H), 1.87-1.80 (m, 1H), 1.62 (m, 2H), 1.42 (s, 18H). ESI/CI-MS m/z 523 ([M−H]⁻). HR-MS (ESI) calcd for C₂₅H₃₆N₂O₆S₂, 525.2093 ([M+H]⁺). Found 525.2093. Three HPLC (reverse-phase, C18) methods were used to determine the purity of the title compound. Method 1: gradient elution, 60% to 85% solvent B (A=aqueous 0.1% H₃PO₄, B=MeCN) in 15 min. Purity (UV-VIS): 99.3% (238 nm); Method 2: gradient elution, 40% to 95% solvent B (A=10 mM NH₄OAc, B=MeCN) in 6 min. Purity (UV-VIS λ): 98.8% (215 nm), 98.3% (254 nm); Method 3: gradient elution, 50% to 99% solvent B (A=aqueous 0.1% H₃PO₄, B=MeCN) in 15 min. Purity (UV-VIS): 97.5% (215 nm).

Example 8

2-[4-(3,5-Di-tert-butyl-4-hydroxy-phenylsulfanyl)-piperidine-1-sulfonyl]-3H-imidazole-4-carboxylic acid

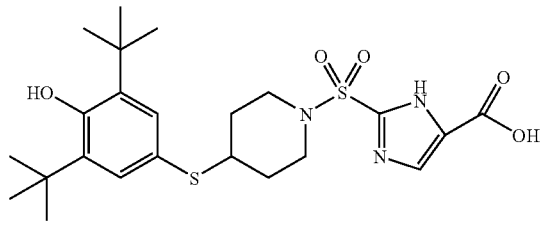

Ex. 8a

2-Mercapto-3H-imidazole-4-carboxylic acid ethyl ester (1 g, 5.8 mmol) was suspended in 1.5 mL of AcOH and 4 mL of water in a 25 mL flask in an ice bath. With stirring, chlorine gas was bubbled through the suspension using a needle. The bubbling was kept at a mild rate for 30 min. The solid was collected by filtration, washed with 10 mL of cold water, and then quickly placed in a vacuum dryer and dried under high vacuum for 15 h to give 2-chlorosulfonyl-3H-imidazole-4-carboxylic acid ethyl ester as a light-green solid (580 mg). It was directly used for the next reaction without further purification. ESI/CI-MS m/z 239 ([M+H]⁺), 237 ([M−H]⁻).

Ex. 8b

To 2,6-di-tert-butyl-4-(piperidin-4-ylsulfanyl)-phenol hydrochloride (Ex. 3c, 405 mg, 1.13 mmol) in 6 mL of dichloromethane was added triethylamine (303 mg, 3 mmol). After stirring for 3 min, 2-chlorosulfonyl-3H-imidazole-4-carboxylic acid ethyl ester (Ex. 8a, 270 mg, 1.13 mmol) in 2 mL of dichloromethane was added. The reaction was stirred for 2 h and then quenched with saturated NaH₂PO₄ (30 mL). The mixture was extracted with Ethyl acetate (50+30 mL) and the combined organic phase was washed with water (50 mL), dried over Na₂SO₄, and concentrated under reduced pressure. Chromatography (5-70% Ethyl acetate/hexanes) gave 2-[4-(3,5-di-tert-butyl-4-hydroxy-phenylsulfanyl)-piperidine-1-sulfonyl]-3H-imidazole-4-carboxylic acid ethyl ester as a yellow foamy solid (390 mg, 66%). ¹H NMR (400 MHz, CDCl₃): δ 10.92 (bs, 0.5H), 10.71 (bs, 0.5H), 7.77 (bs, 1H), 7.25 (s, 2H), 5.30 (s, 1H), 4.39 (q, J=7.2 Hz, 2H), 3.80 (dt, J=12.4, 4.4 Hz, 2H), 3.00-2.88 (m, 3H), 2.02-1.98 (m, 2H), 1.68 (m, 2H), 1.42 (s, 18H), 1.38 (t, J=7.2 Hz, 3H). ¹³C NMR: δ 154.6, 136.6, 132.0, 122.0, 60.9, 46.1, 44.5, 34.5, 31.7, 30.4, 14.5. ESI/CI-MS m/z 525 ([M+H]⁺), 523 ([M−H]⁻).

To 2-[4-(3,5-di-tert-butyl-4-hydroxy-phenylsulfanyl)-piperidine-1-sulfonyl]-3H-imid-azole-4-carboxylic acid ethyl ester (Ex. 8b, 390 mg) in 4 mL of Methanol was added a NaOH solution (150 mg in 2.5 mL of water). The mixture was stirred for 7 h and then quenched with saturated NaH₂PO₄ (30 mL). It was extracted with Ethyl acetate (2×40 mL) and the combined organic phase was dried over Na₂SO₄ and concentrated under reduced pressure. Chromatography (2-15% Methanol/dichloromethane) gave the title compound as a light-pink foamy solid (290 mg, 79%), mp 219-220° C. ¹H NMR (400 MHz, acetone-d₆): δ 7.95 (s, 1H), 7.27 (s, 2H), 6.21 (bs, 1H), 3.74 (dt, J=7.2, 3.6 Hz, 2H), 3.06 (m, 1H), 2.93 (td, J=12.4, 3.6 Hz, 2H), 2.06-1.97 (m, 2H), 1.58 (m, 2H), 1.41 (s, 18H). ¹³C NMR (100 MHz): a 154.5, 138.3, 131.3, 122.8, 45.9, 43.9, 34.4, 31.9. ESI/CI-MS m/z 496 ([M+H]⁺), 494 ([M−H]⁻). Anal. calcd for C₂₃H₃₃N₃O₅S₂: C, 55.73; H, 6.71; N, 8.48. Found: C, 55.26, H, 6.84; N, 7.84.

Example 9

2,6-Di-tert-butyl-4-[1-(5-hydroxymethyl-1H-imidazole-2-sulfonyl)-piperidin-4-ylsulfanyl]-phenol

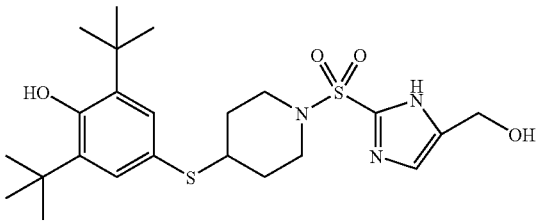

To 2-[4-(3,5-di-tert-butyl-4-hydroxy-phenylsulfanyl)-piperidine-1-sulfonyl]-3H-imid-azole-4-carboxylic acid ethyl ester (Ex. 8b, 190 mg, 0.36 mmol) in 3 mL of THF was added 1 mL of 1 M LiAlH₄ solution (1 mmol). The reaction was stirred at room temperature for 1 h and then quenched with saturated NaH₂PO₄ (20 mL). The mixture was diluted with 30 mL of Ethyl acetate and stirred for 10 min and let sit for 1 h. The layers were separated and the aqueous layer was extracted with Ethyl acetate (30 mL). The combined organic phase was dried over Na₂SO₄ and concentrated under reduced pressure. Chromatography (1-8% Methanol/dichloromethane) gave the title compound as a white solid (125 mg, 72%), mp 122-123° C. ¹H NMR (400 MHz, CDCl₃): δ 7.23 (s, 2H), 7.07 (s, 1H), 5.29 (s, 1H), 4.65 (s, 2H), 3.72 (m, 2H), 2.88-2.81 (m, 3H), 1.97 (m, 2H), 1.64 (m, 2H), 1.41 (s, 18H). ESI/CI-MS m/z 482 ([M+H]⁺), 480 ([M−H]⁻). Two HPLC (reverse-phase, C, 8) methods were used to determine the purity of the title compound. Method 1: gradient elution, 60% to 85% solvent B (A=aqueous 0.1% H₃PO₄, B=MeCN) in 15 min. Purity (UV-VIS): 98.3% (238 nm); Method 2: gradient elution, 40% to 95% solvent B (A=10 mM NH₄OAc, B=MeCN) in 6 min. Purity (UV-VIS λ): 98.5% (215 nm), 99.5% (254 nm), 99.5% (280 nm).

Example 10

5-[4-(3,5-Di-tert-butyl-4-hydroxy-phenylsulfanyl)-piperidine-1-sulfonyl]-furan-2-carboxylic acid

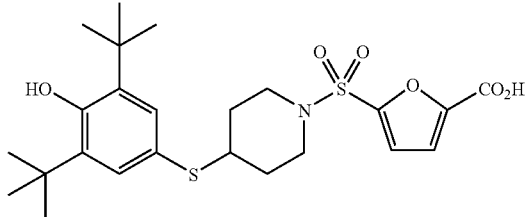

Ex. 10a

To 2,6-di-tert-butyl-4-(piperidin-4-ylsulfanyl)-phenol hydrochloride (Ex. 3c, 280 mg, 0.78 mmol) in 5 mL of dichloromethane was added triethylamine (240 mg, 2.37 mmol). The mixture was stirred for 3 min followed by the addition of 5-chlorosulfonyl-furan-2-carboxylic acid methyl ester (210 mg, 0.94 mmol). The stirring was continued for 2 h at room temperature and then the reaction was quenched with 20 mL of saturated $NaH_2PO_4$. The mixture was extracted with Ethyl acetate (40 mL) and the organic phase was dried over $Na_2SO_4$ and concentrated under reduced pressure. Chromatography (3-50% Ethyl acetate/hexanes) gave 5-[4-(3,5-di-tert-butyl-4-hydroxy-phenylsulfanyl)-piperidine-1-sulfonyl]-furan-2-carboxylic acid methyl ester as a clear oil (295 mg, 74%). ESI/CI-MS m/z 508 ([M−H]−).

To 5-[4-(3,5-di-tert-butyl-4-hydroxy-phenylsulfanyl)-piperidine-1-sulfonyl]-furan-2-carboxylic acid methyl ester (Ex. 10a, 295 mg, 0.58 mmol) in 4 mL of Methanol was added NaOH (230 mg, 5.8 mmol) in 3.5 mL of water. The reaction was stirred for 3 h at room temperature and then quenched with saturated $NaH_2PO_4$ (30 mL). The mixture was extracted with Ethyl acetate (40+20 mL) and the combined organic phase was dried over $Na_2SO_4$ and concentrated under reduced pressure. Chromatography (1-5% Methanol/dichloromethane) gave the title compound as a foamy solid (225 mg, 78%). $^1$H NMR (400 MHz, $CDCl_3$): δ 7.33 (d, J=3.4 Hz, 1H), 7.242 (s, 2H), 7.06 (d, J=3.4 Hz, 1H), 5.3 (s, 1H), 3.79 (m, 2H), 2.91 (m, 3H), 2.00 (m, 2H), 1.67 (m, 2H), 1.41 (s, 18H). $^{13}$C NMR (100 MHz): δ 161.8, 154.6, 151.9, 146.3, 136.9, 132.1, 122.0, 119.8, 117.2, 45.6, 44.5, 34.5, 31.7, 30.4. ESI/CI-MS m/z 451 ([M+H]+), 449 ([M−H]−). Anal. Calcd. for $C_{24}H_{33}NO_6S_2$: C, 58.16; H, 6.71; N, 2.83. Found: C, 57.35, H, 7.06; N, 2.52.

Example 11

2,6-Di-tert-butyl-4-[1-(5-(1-hydroxy-1-methyl-ethyl)-1H-pyrrole-2-sulfonyl)-piperidin-4-ylsulfanyl]-phenol

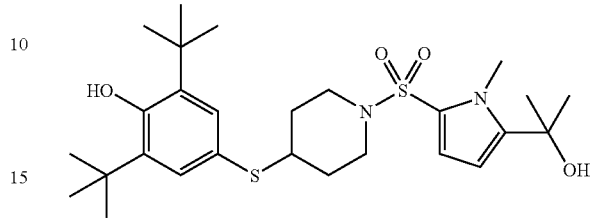

To 5-[4-(3,5-di-tert-butyl-4-hydroxy-phenylsulfanyl)-piperidine-1-sulfonyl]-1-methyl-1H-pyrrole-2-carboxylic acid methyl ester (Ex. 4a, 281 mg, 0.53 mmol) in 5 mL of THF was added MeMgCl (0.716 ml, 2.15 mmol). The mixture was stirred at 0° C. overnight and then quenched with saturated 0.5 N HCl (20 mL) and extracted with Ethyl acetate (2×20 mL). The combined organic extracts were dried over $Na_2SO_4$ and concentrated under reduced pressure. Chromatography (0-40% Ethyl acetate/hexanes) gave 115 mg of the title compound as a off-white solid. $^1$H NMR (400 MHz, $CDCl_3$): δ 7.24 (s, 2H), 6.97 (d, 1H, J=2 Hz), 6.18 (d, 1H, J=2 Hz), 5.29 (s, 1H), 3.86 (s, 3H), 3.59-3.53 (m, 2H), 2.82-2.74 (m, 1H), 2.51-2.43 (m, 2H), 2.02-1.94 (m, 2H), 1.82 (s, 1H), 1.74-1.66 (m, 2H), 1.61 (s, 6H), 1.41 (s, 18H).

Example 12

2,6-Di-tert-butyl-4-{1-[5-(1-hydroxy-1-methyl-ethyl)-1H-imidazole-2-sulfonyl]-piperidin-4-ylsulfanyl}-phenol

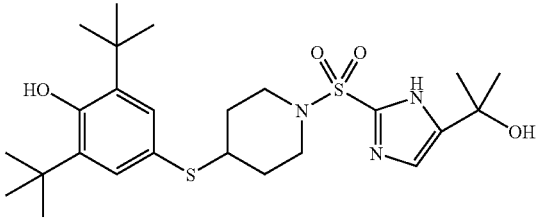

To 2-[4-(3,5-di-tert-butyl-4-hydroxy-phenylsulfanyl)-piperidine-1-sulfonyl]-3H-imidazole-4-carboxylic acid ethyl ester (Ex. 8b, 230 mg, 0.44 mmol) in 3 mL of THF was added dropwise a 3.0 M THF solution of MeMgCl (0.85 mL, 2.55 mmol) at 0° C. The reaction was allowed to warm to room temperature, stirred for 5 h, and then quenched with saturated $NaH_2PO_4$ (20 mL). The mixture was extracted with Ethyl acetate (40+20 mL) and the combined organic phase was dried over $Na_2SO_4$ and concentrated under reduced pressure. The crude product was purified by chromatography (3-30% Ethyl acetate/hexanes) to afford the title compound as a clear gum (202 mg, 90%). $^1$H NMR (400 MHz, $CDCl_3$): δ 10.76 (bs, 0.4H), 10.72 (bs, 0.6H), 7.23 (s, 2H), 7.02 (s, 0.6H), 6.97 (s, 0.4H), 5.30 (s, 1H), 3.77-3.74 (m, 2H), 2.97-2.82 (m 3H), 1.98-1.95 (m, 2H), 1.69-1.57 (m, 8H), 1.41 (s, 18H). $^{13}$C NMR (100 MHz): δ 154.5, 152.1, 141.2, 140.9, 136.9, 132.9, 132.0, 125.8, 122.1, 113.2, 69.5, 68.4, 46.0, 44.6, 34.5, 31.7, 31.5, 30.6, 30.4, 30.2. ESI/CI-MS m/z 510 ([M+H]⁺), 508 ([M−H]⁻). Three HPLC (reverse-phase, $C_{18}$) methods were used to determine the purity of the title compound. Method 1: gradient elution, 40% to 85% solvent B (A=aqueous 0.1% $H_3PO_4$, B=MeCN) in 15 min. Purity (UV-VIS): 98.6% (238 nm); Method 2: gradient elution, 40% to 95% solvent B (A=10 mM $NH_4OAc$, B=MeCN) in 6 min. Purity (UV-VIS λ): 99.2% (238 nm), 99.4% (254 nm); Method 3: gradient elution, 50% to 99% solvent B (A=aqueous 0.1% $H_3PO_4$, B=MeCN) in 15 min. Purity (UV-VIS): 98.4% (215 nm), 98.9% (254 nm), 98.7 (238 nm).

Example 13

(R)-5-[3-(3,5-Di-tert-butyl-4-hydroxy-phenylsulfanyl)-pyrrolidine-1-sulfonyl]-1-methyl-1H-pyrrole-2-carboxylic acid

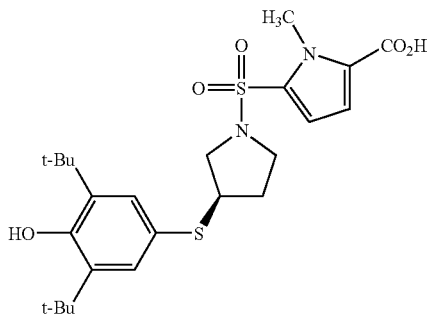

Ex. 13a

To a solution of (S)-3-hydroxypyrrolidine (2.0 g, 22.9 mmol) in THF (40 mL) was added diisopropylethylamine (12.0 mL, 68.9 mmol) and 5-chlorosulfonyl-1-methyl-1H-pyrrole-2-carboxylic acid methyl ester (6.0 g, 25.3 mmol). The resulting solution was stirred at room temperature for 2 h. Upon completion, as determined by HPLC, the reaction was acidified with 3N HCl and partitioned between $H_2O$ (100 mL) and Ethyl acetate (100 mL). The layers were cut and the aqueous layer was extracted with Ethyl acetate (3×100 mL) and EtOAc:THF (1:1, 2×100 mL). The combined organic cuts were washed with a 50% aqueous brine solution (1×100 mL) and brine (1×100 mL), dried over $Na_2SO_4$, and concentrated under reduced pressure. Silica gel chromatography (Ethyl acetate:hexanes, 4:1) afforded 6.31 g (95%) of (S)-5-(3-hydroxy-pyrrolidine-1-sulfonyl)-1-methyl-1H-pyrrole-2-carboxylic acid methyl ester as a white solid, mp 108-109° C. ¹H-NMR (400 MHz, $CDCl_3$): δ 7.25 (d, 1H, J=2.4 Hz), 7.17 (d, 1H, J=2.4 Hz), 4.40 (brs, 1H), 3.96 (s, 3H), 3.83 (s, 3H), 3.33-3.40 (m, 3H), 3.20-3.23 (m, 1H), 1.93-2.02 (m, 1H), 1.82-1.89 (m, 1H), 1.79 (brs, 1H). Anal. Calcd. for $C_{11}H_{16}N_2O_5S$, C, 45.82; H, 5.59; N, 9.72; S, 11.12. Found: C, 45.92; H, 5.63; N, 9.61; S, 11.24.

Ex. 13b

To a solution of (S)-5-(3-hydroxy-pyrrolidine-1-sulfonyl)-1-methyl-1H-pyrrole-2-carboxylic acid methyl ester (Ex. 13a, 6.1 g, 21.2 mmol) and triethylamine (8.9 mL, 63.5 mmol) in methylene chloride (75 mL) at 0° C. was added methanesulfonyl chloride (2.4 mL, 31.8 mmol). The resulting solution was warmed to room temperature and stirred at room temperature for 2 h. Upon completion, as determined by HPLC, the reaction was quenched with 1N HCl (150 mL) and diluted with water (100 mL). The layers were cut and the organic layer was washed with 1N HCl (2×100 mL), a 50% aqueous brine solution (1×100 mL) and brine (1×100 mL), dried over $Na_2SO_4$, and concentrated under reduced pressure to afford 7.8 g (99%) of (S)-5-(3-methanesulfonyloxy-pyrrolidine-1-sulfonyl)-1-methyl-1H-pyrrole-2-carboxylic acid methyl ester as an orange foam. This material was used without further purification. ¹H-NMR (400 MHz, $CDCl_3$): δ 7.27 (d, 1H, J=2.0 Hz), 7.17 (d, 1H, J=2.0 Hz), 5.15-5.17 (m, 1H), 3.97 (s, 3H), 3.84 (s, 3H), 3.43-3.60 (m, 3H), 3.30-3.37 (m, 1H), 2.94 (s, 3H), 2.17-2.23 (m, 1H), 2.09-2.16 (m, 1H). mp 79-81° C. Anal. Calcd. for $C_{12}H_{18}N_2O_7S_2$: C, 39.34; H, 4.95; N, 7.65; S, 17.50. Found: C, 39.20; H, 5.00; N, 7.56; S, 17.66.

Ex. 13c

To a solution of (S)-5-(3-methanesulfonyloxy-pyrrolidine-1-sulfonyl)-1-methyl-1H-pyrrole-2-carboxylic acid methyl ester (Ex. 13b, 7.75 g, 21.2 mmol) and cesium carbonate (11.6 g, 31.8 mmol) in degassed MEK (85 mL) at 60° C. was added 2,6-di-tert-butyl-4-mercaptophenol (7.6 g, 31.8 mmol). The resulting solution was stirred at 60° C. for 3 h. Upon completion, as determined by HPLC, the reaction was diluted with $H_2O$ (200 mL) and Ethyl acetate (100 mL). The layers were cut and the aqueous layer was extracted with Ethyl acetate (3×100 mL). The combined organic cuts were washed with a saturated ammonium chloride solution (1×100 mL), a 50% aqueous brine solution (1×100 mL) and brine (1×100 mL), dried over $Na_2SO_4$, and concentrated under reduced pressure. Silica gel chromatography (Ethyl acetate:hexanes, 1:2) afforded 9.34 g (87%) of (R)-5-[3-(3,5-di-tert-butyl-4-hydroxy-phenylsulfanyl)-pyrrolidine-1-sulfonyl]-1-methyl-1H-pyrrole-2-carboxylic acid methyl ester as a white solid, mp 83-85° C. ¹H-NMR (400 MHz, $CDCl_3$): δ 7.23 (d, 1H, J=2.0 Hz), 7.21 (s, 2H), 7.17 (d, 1H, J=2.0 Hz), 5.30 (s, 1H), 3.97 (s, 3H), 3.84 (s, 3H), 3.59 (dd, 1H, J=10.4, 7.2 Hz), 3.47 (pentet, 1H, J=6.8 Hz), 3.28-3.39 (m, 2H), 3.10 (dd, 1H, J=10.4, 6.4 Hz), 2.12-2.20 (m, 1H), 1.75-1.84 (m, 1H), 1.42 (s, 18H). Anal. Calcd. for $C_{25}H_{36}N_2O_5S_2$: C, 59.03; H, 7.13; N, 5.51; S, 12.61. Found: C, 59.63; H, 7.34; N, 5.39; S, 12.23.

To a solution of (R)-5-[3-(3,5-di-tert-butyl-4-hydroxy-phenylsulfanyl)-pyrrolidine-1-sulfonyl]-1-methyl-1H-pyrrole-2-carboxylic acid methyl ester (Ex. 13c, 9.2 g, 18.1 mmol) in THF (35 mL), and Methanol (12 mL) was added a solution of lithium hydroxide (2.2 g, 90.6 mmol) in water (12 mL) and the resulting solution was stirred at room temperature for 3 h. Upon completion, as determined by HPLC, the reaction was diluted with Ethyl acetate (100 mL) and quenched with 0.1 M citric acid (150 mL) and 1N HCl (50 mL). The layers were cut and the aqueous layer was extracted with Ethyl acetate (2×100 mL). The combined organic cuts were washed with a 1:1 brine:water solution (1×100 mL) and brine (1×100 mL), dried over $Na_2SO_4$, and concentrated under reduced pressure. Silica gel chromatography (50-80% Ethyl acetate/hexanes to 5% MeOH/$CH_2Cl_2$) afforded 6.60 g (75%) of the title compound as an off-white solid. ¹H-NMR (400 MHz, DMSO-$d_6$): δ 7.32 (d, 1H, J=2.0 Hz), 7.30 (d, 1H, J=2.0 Hz), 7.21 (s, 2H), 5.31 (s, 1H), 3.98 (s, 3H), 3.61 (dd, 1H, J=10.4, 7.2 Hz), 3.49 (pentet, 1H, J=6.8 Hz), 3.30-3.41 (m, 2H), 3.12 (dd, 1H, J=10.4, 6.4 Hz), 2.13-2.21 (m, 1H), 1.77-1.86 (m, 1H), 1.42 (s, 18H). Anal. Calcd. for C$_{24}$H$_{34}$N$_2$O$_5$S$_2$: C, 58.27; H, 6.93; N, 5.66; S, 12.96. Found: C, 58.16; H, 6.80; N, 5.71; S, 12.84.

Example 14

(S)-5-[3-(3,5-Di-tert-butyl-4-hydroxy-phenylsulfanyl)-pyrrolidine-1-sulfonyl]-1-methyl-1H-pyrrole-2-carboxylic acid

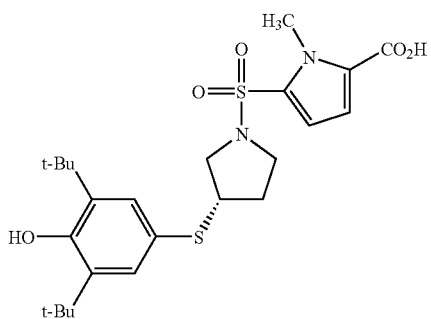

The title compound was prepared in the same manner as for its enantiomer described in Ex. 13 using (R)-3-hydroxypyrrolidine. Off-white solid (31%). $^1$H-NMR (400 MHz, CDCl$_3$): δ 7.30 (m, 1H), 7.26 (s, 1H), 7.22 (s, 2H), 5.31 (s, 1H), 3.98 (s, 3H), 3.61 (dd, 1H, J=10.4, 7.2 Hz), 3.49 (pentet, 1H, J=6.8 Hz), 3.30-3.40 (m, 2H), 3.12 (dd, 1H, J=10.4, 6.4 Hz), 2.15-2.20 (m, 1H), 1.79-1.84 (m, 1H), 1.42 (s, 18H). Anal. Calcd. for C$_{24}$H$_{34}$N$_2$O$_5$S$_2$: C, 58.27; H, 6.93; N, 5.66; S, 12.96. Found: C, 58.42; H, 7.11; N, 5.58; S, 12.79.

Example 15

(S)-2,6-Di-tert-butyl-4-[1-(5-hydroxymethyl-1-methyl-1H-pyrrole-2-sulfonyl)-pyrrolidin-3-ylsulfanyl]-phenol

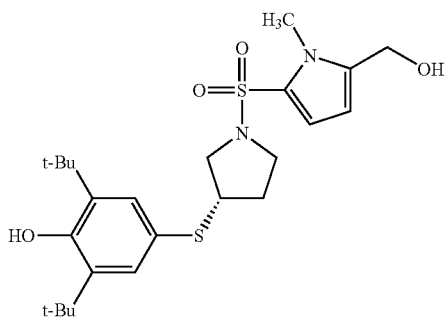

To a solution of S-5-[3-(3,5-di-tert-butyl-4-hydroxy-phenylsulfanyl)-pyrrolidine-1-sulfonyl]-1-methyl-1H-pyrrole-2-carboxylic acid (Ex. 14, 0.45 g, 0.91 mmol) in THF (30 mL) at room temperature was added lithium aluminum hydride (1M in THF, 4.5 mL, 4.5 mmol). The resulting solution was stirred at 40° C. for 18 h. Upon completion, as determined by HPLC, the reaction was quenched with sodium sulfate decahydrate and diluted with H$_2$O (50 mL) and Ethyl acetate (50 mL). The layers were cut and the aqueous layer was extracted with Ethyl acetate (2×50 mL), dried over Na$_2$SO$_4$, and concentrated under reduced pressure. Silica gel chromatography (Ethyl acetate/hexanes, 2:1) afforded 0.31 g (75%) of the title compound as an white solid, mp 68-70° C. $^1$H-NMR (400 MHz, CDCl$_3$): δ 7.26 (s, 2H), 7.13 (d, 1H, J=2.0 Hz), 6.37 (d, 1H, J=2.0 Hz), 5.30 (s, 1H), 4.58 (d, 2H, J=5.6 Hz), 3.73 (s, 3H), 3.60 (dd, 1H, J=10.4, 7.2 Hz), 3.45 (pentet, 1H, J=7.2 Hz), 3.28-3.35 (m, 2H), 3.60 (dd, 1H, J=10.4, 6.8 Hz), 2.13-2.18 (m, 1H), 1.75-1.80 (m, 1H), 1.51 (t, 1H, J=5.6 Hz), 1.42 (s, 18H). Anal. Calcd. for C$_{24}$H$_{36}$N$_2$O$_5$S$_2$: C, 59.17; H, 7.55; N, 5.83; S, 13.34. Found: C, 60.16; H, 7.50; N, 5.68; S, 12.89.

Example 16

5-[4-(3,5-Di-tert-butyl-4-hydroxy-phenylsulfanyl)-piperidine-1-sulfonyl]-1-methyl-1H-pyrrole-2-carboxylic acid L-arginine salt

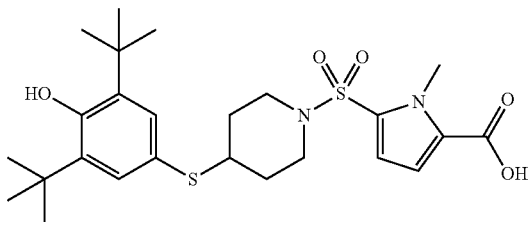

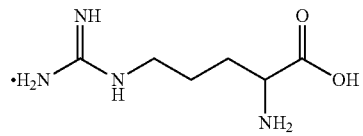

To a solution of 5-[4-(3,5-di-tert-butyl-4-hydroxy-phenylsulfanyl)-piperidine-1-sulfonyl]-1-methyl-1H-pyrrole-2-carboxylic acid (Ex. 4, 0.60 g, 1.18 mmol) in EtOH (2.4 mL) at room temperature was added a solution of L-arginine (0.20 g, 1.18 mmol) in water (2.4 mL). After 5 min of stirring, the mixture solidified and an additional 3 mL of EtOH was added to ensure a homogeneous solution. It was stirred at room temperature for 1 h and then concentrated under reduced pressure. The solid residue was triturated with EtOH (2.4 mL×2). The material was then taken up again in EtOH and stirred at room temperature overnight. The resulting solid was collected on filter paper and dried in vacuo to afford 0.48 g (60%) of the title compound as a white solid, mp 216-220° C. $^1$H-NMR (400 MHz, DMSO-d$_6$): δ 7.98 (brs, 5H), 7.22 (s, 1H), 7.10 (s, 2H), 6.52 (s, 1H), 3.88 (s, 3H), 3.43-3.46 (m, 2H), 3.06-3.12 (m, 3H), 2.96-2.98 (m, 1H), 2.35 (t, 2H, J=11.0 Hz), 1.90-1.93 (m, 2H), 1.56-1.72 (m, 4H), 1.45-1.51 (m, 2H), 1.35 (s, 18H), 1.04-1.08 (m, 1H). HRMS (ESI) Calcd. for C$_{31}$H$_{50}$N$_6$O$_7$S$_2$, 683.3260 ([M+H]$^+$). Found: 683.3272. Anal. Calcd. for C$_{31}$H$_{50}$N$_6$O$_7$S$_2$.2H$_2$O: C, 51.79; H, 7.57; N, 11.69; S, 8.92. Found: C, 51.94; H, 7.47; N, 11.53; S, 8.85.

Example 17

5-[4-(3,5-Di-tert-butyl-4-hydroxy-phenylsulfanyl)-piperidine-1-sulfonyl]-1-methyl-1H-pyrrole-2-carboxylic acid meglumine salt

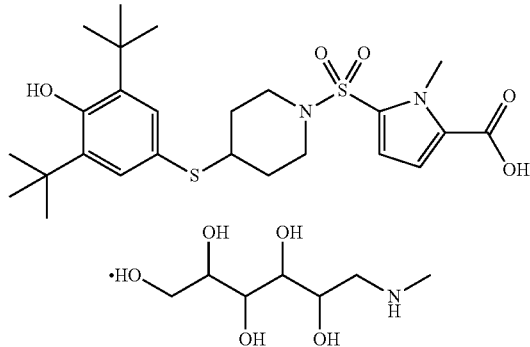

To a solution of 5-[4-(3,5-di-tert-butyl-4-hydroxy-phenylsulfanyl)-piperidine-1-sulfonyl]-1-methyl-1H-pyrrole-2-carboxylic acid (Ex. 4, 0.60 g, 1.18 mmol) in THF (2.0 mL) was added a solution of N-methyl-D-glucamine (meglumine, 0.23 g, 1.18 mmol) in water:THF (1:1, 2.0 mL). The resulting solution was stirred at room temperature for 30 min, then concentrated under reduced pressure and the solid residue was triturated with THF (2.0 mL×2). The material was then taken up in Ethyl acetate/hexanes and the resulting slurry was stirred at room temperature overnight. The solid was collected on filter paper and dried in vacuo to afford 0.68 g (82%) of the title compound as a white solid, mp 179-182° C. $^1$H-NMR (400 MHz, DMSO-d$_6$): δ 7.27 (s, 1H), 7.10 (s, 2H), 6.57 (s, 1H), 5.73 (brs, 2H), 4.66 (brs, 3H), 3.88 (s, 3H), 3.83-3.85 (m, 2H), 3.66-3.67 (m, 2H), 3.57-3.61 (m, 2H), 3.47-3.49 (m, 1H), 3.40-3.44 (m, 1H), 2.92-2.98 (m, 3H), 2.82-2.87 (m, 1H), 2.47 (s, 3H), 2.33-2.38 (m, 2H), 1.90-1.93 (m, 2H), 1.43-1.50 (m, 2H), 1.35 (s, 18H). HRMS (ESI) Calcd. for C$_{32}$H$_{53}$N$_3$O$_{10}$S$_2$, 704.3250 ([M+H]$^+$). Found: 704.3269. Anal. Calcd. for C$_{32}$H$_{53}$N$_3$O$_{10}$S$_2$/1;2H$_2$O: C, 54.60; H, 7.59; N, 5.97; S, 9.11. Found: C, 54.29; H, 7.45; N, 5.97; S, 8.85.

Example 18

5-[4-(3,5-Di-tert-butyl-4-hydroxy-phenylsulfanyl)-piperidine-1-sulfonyl]-1-methyl-1H-pyrrole-2-carboxylic acid tris(hydroxymethyl)aminomethane (THAM) Salt

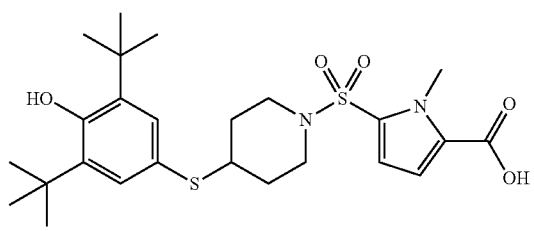

-continued

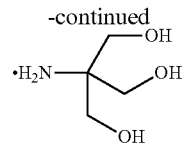

To a solution of 5-[4-(3,5-di-tert-butyl-4-hydroxy-phenylsulfanyl)-piperidine-1-sulfonyl]-1-methyl-1H-pyrrole-2-carboxylic acid (Ex. 4, 0.60 g, 1.18 mmol) in THF (3.5 mL) was added tris(hydroxymethyl)aminomethane (0.14 g, 1.18 mmol). The resulting solution was stirred at 40° C. on a rotary evaporator for 1 h at atmospheric pressure and then concentrated under reduced pressure, and the solid residue was triturated with THF (3.0 mL). The material was then taken up in Ethyl acetate/hexanes and the resulting slurry was stirred at room temperature overnight. The solid was collected on filter paper and dried in vacuo to afford 0.57 g (77%) of the title compound as a white solid, mp 199-201° C. $^1$H-NMR (400 MHz, DMSO-d$_6$): δ 7.29 (s, 1H), 7.11 (s, 2H), 6.57 (s, 1H), 5.50 (brs, 3H), 3.88 (s, 3H), 3.44 (s, 10H), 2.96-3.01 (m, 1H), 2.36 (t, 2H, J=11.0 Hz), 1.90-1.93 (m, 2H), 1.42-1.51 (m, 2H), 1.36 (s, 18H). HRMS (ESI) Calcd. for C$_{29}$H$_{47}$N$_3$O$_8$S$_2$, 630.2883 ([M+H]$^+$). Found: 630.2894. Anal. Calcd. for C$_{29}$H$_{47}$N$_3$O$_8$S$_2$.½H$_2$O: C, 54.52; H, 7.57; N, 6.58; S, 10.04. Found: C, 54.73; H, 7.50; N, 6.56; S, 10.01.

Example 19

2-[4-(3,5-Di-tert-butyl-4-hydroxy-phenylsulfanyl)-piperidine-1-sulfonyl]-thiazole-4-carboxylic acid

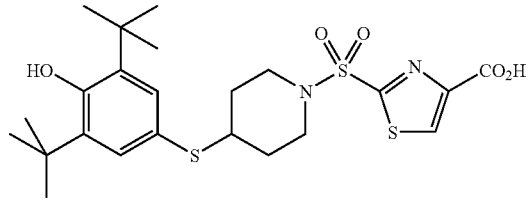

Ammonia gas was bubbled into 25 mL of 95% ethyl alcohol in a ice batch for 1 h until the weight gain of 3.9 g. To this mixture was added a solution of carbon disulfide (7.6 g) in 20 mL of ether, cooled to 0° C. The resulting mixture was loosely capped and allowed to remain in the ice bath for 2 h and then aged at ambient temperature for 15 h. The mixture was cooled in a ice batch and the solid was collected by filtration, washed with ether and air dried to afford the ammonium thiocarbamate as an orange solid (7.8 g).

Ex. 19b

To a solution of bromo pyruvic acid (5 g, 30 mmol) in 4 mL water was added ammonium thiocarbamate (Ex. 19a, 3.3 g, 33 mmol). The resulting solution was stirred for 3 h and the solid was collected by filtration. The crude 2-mercaptothiazole-4-carboxylic acid (4.3 g) was used without further purification.

Ex. 19c

To 2-mercaptothiazole-4-carboxylic acid (Ex. 19b, 4.2 g) in 50 mL ethyl alcohol was added 2 mL conc. H$_2$SO$_4$. The mixture was heated to reflux for 8 h and cooled. The solvent was removed under reduced pressure and the residue was poured onto 50 mL ice water. The solid was collected, washed with water and dried under vacuum. The crude product was recrystallized from 8 mL ethyl alcohol to afford ethyl 2-mercaptothiazole-4-carboxylate (2.3 g) as a yellow solid.

Ex. 19d

To ethyl 2-mercaptothiazole-4-carboxylate (Ex. 19c, 1 g) in 8 mL acetic acid and 2 mL water was bubbled chlorine gas for 30 min. The solid was collected, washed with water and dried under vacuum to afford ethyl 2-(chlorosulfonyl)-thiazole-4-carboxylate (0.89 g) as a pale yellow solid.

Ex. 19e

Ethyl 2-[4-(3,5-di-tert-butyl-4-hydroxy-phenylsulfanyl)-piperidine-1-sulfonyl]-thiazole-4-carboxylate was prepared in a manner similar to Ex. 3d from ethyl 2-(chlorosulfonyl)-thiazole-4-carboxylate (Ex. 19d) and 2,6-di-tert-butyl-4-piperidin-4-ylsulfanyl)-phenol (Ex. 3d). Hydrolysis to the title compound (230 mg as an off white foam) was accomplished in a manner similar to Ex. 3e. $^1$H-NMR (400 MHz, CDCl$_3$): δ 9.16 (bs, 1H), δ 8.51 (s, 1H), 7.23 (s, 1H), 7.22 (s, 1H), 5.30 (s, 1H), 3.86 (m, 2H), 2.98 (m, 2H), 2.93 (m, 2H), 2.00 (m, 2H), 1.71 (m, 2H), 1.44 (s, 18H).

Example 20

2,6-Di-tert-butyl-4-[1-(4-hydroxymethyl-thiazole-2-sulfonyl)-piperidin-4-ylsulfanyl]-phenol

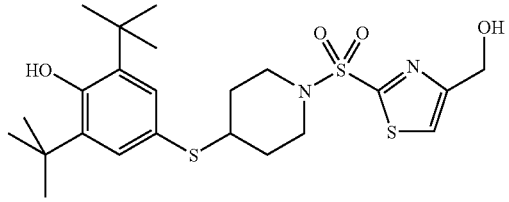

The title compound was prepared (116 mg, clear oil) in a manner similar to Ex. 5 from ethyl 2-[4-(3,5-di-tert-butyl-4-hydroxy-phenylsulfanyl)-piperidine-1-sulfonyl]-thiazole-4-carboxylate (Ex. 19e) and LiAlH$_4$. $^1$H-NMR (400 MHz, CDCl$_3$): δ 7.51 (s, 1H), 7.23 (s, 2H), 5.31 (s, 1H), 4.84 (s, 2H), 3.80 (m, 2H), 2.90 (m, 2H), 2.42 (bs, 1H), 1.99 (m, 2H), 1.68 (m, 2H), 1.39 (s, 18H).

Example 21

5-[4-(3,5-Di-tert-butyl-4-hydroxy-phenylsulfanyl)-piperidine-1-sulfonyl]-1-ethyl-1H-pyrrole-2-carboxylic acid

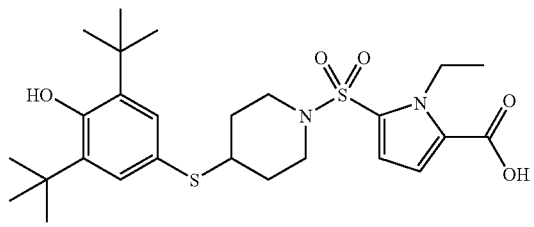

The title compound was prepared (560 mg, lightly colored solid) in a manner similar to Ex. 4. $^1$H-NMR (400 MHz, CDCl$_3$): δ 7.29 (s, 1H), 7.24 (s, 2H), 5.30 (s, 1H), 4.38 (q, J=7.2 Hz, 2H), 3.58 (m, 2H), 2.80 (m, 1H), 2.53 (m, 2H), 2.00 (m, 2H), 1.73 (m, 2H), 1.44 (t, J=7.2 Hz, 3H), 1.42 (s, 18H).

Example 22

5-[4-(3,5-Di-tert-butyl-4-hydroxy-phenylsulfanyl)-piperidine-1-sulfonyl]-1H-pyrrole-2-carboxylic acid

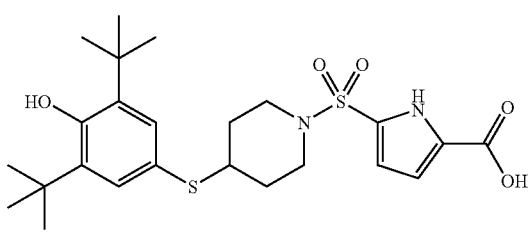

The title compound was prepared (590 mg, colored solid) in a manner similar to Ex. 4. $^1$H-NMR (400 MHz, CDCl$_3$): δ 9.70 (bs, 1H), δ 7.44 (s, 1H), 7.29 (s, 2H), 7.21 (s, 1H), 5.32 (s, 1H), 3.62 (m, 2H), 2.84 (m, 1H), 2.58 (m, 2H), 2.05 (m, 2H), 1.74 (m, 2H), 1.44 (s, 18H).

Example 23

Biological Data, Mouse Model of Asthma

Male 5-6 week old Balb/CJ mice were obtained from Jackson Laboratories (Bar Harbor, Me.). All experimental animals were used in accordance to Institutional Animal Care and Use Committee of AtheroGenics, Inc. Mice were sensitized by administering an intraperitoneal injection of 20 µg of ovalbumin (Calbiochem, La Jolla, Calif.) adsorbed in 2 mg of alum (Imject Alum; Pierce, Rockford, Ill.) on day 0 and 14. A group of mice received saline and served as negative control animals. The mice were challenged by aerosol exposure to ovalbumin (1% [wt/vol]) for 25 minutes on 3 consecutive days (days 28, 29, and 30) in a plexiglass exposure chamber coupled to an Aeroneb nebulizer (Buxco Electronics, Wilmington, N.C.). Experimental compounds were dissolved in Glycofurol/PEG 300/Tween (35%/55%/10%) (Sigma-Aldrich; Milwaukee, Wis.). Animals were dosed orally with either test compound or vehicle (6 ml/kg dosing volume) on days 26-32 of study. Compound or vehicle was administered 2 hour before the aerosol challenge on days 28, 29, and 30 and 1 hour before airway reactivity measurement on day 32.

Methacholine-induced airway reactivity was assessed on day 32. Methacholine was administered in increasing concentrations (0.375, 0.77, 1.5, 3, 6, 12, 25, and 50 mg/ml) to unrestrained mice. Increases in airway resistance to Methacholine were determined as enhanced pause, (Penh) values, during and after the exposure (6-minute total analysis time). Mice were then humanely euthanized with an overdose of ketamine/xylazine and plasma samples collected for determination of drug levels. The data is presented as the % inhibition of the PenH vs McH dose AUC compared with the vehicle control.

Data analysis was conducting using the software package, JMP (SAS Institute Inc; Cary, N.C.). The Dunnett's multiple comparison test was used to compare treatment group means to the vehicle control group. P values of less than 0.05 were considered statistically significant. The data (Table 1) is presented as the % inhibition of the PenH vs McH dose AUC compared with the vehicle control.

TABLE 1

Biological data of compounds

| Example No. | Reduction of Penh AUC at 50 mg/kg p.o. |
| --- | --- |
| 1 | 3 |
| 2 | 1 |
| 3 | 2 |
| 4 | 1 |
| 5 | 1 |
| 6 | 3 |
| 7 | 2 |
| 8 | 2 |
| 9 | 2 |
| 10 | not tested |
| 11 | 3 |
| 12 | 3 |
| 13 | 3 |
| 14 | 3 |
| 15 | 3 |
| 16 | 3 |
| 17 | not tested |
| 18 | 1 |
| 19 | not tested |
| 20 | not tested |
| 21 | not tested |
| 22 | not tested |

1: >40% and statistically significant
2: 20-40% and either statistically significant or not
3: <20% (no significant activity)

We claim:

1. A compound of Formula I

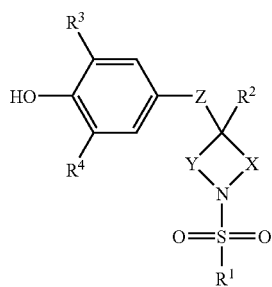

(I)

or its pharmaceutically acceptable salt, wherein:

X and Y are independently selected from —CH$_2$— or —CH$_2$—CH$_2$—;

Z is selected from S(O)$_m$ or Se(O)$_m$;

m is 0, 1 or 2;

R$^1$ is heteroaryl, optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^5$R$^6$, oxo, cyano, carboxy, carboxyalkyl, alkoxycarbonyl, —OR$^5$, —C(O)R$^5$, —C(O)—NH$_2$, —C(O)—N(H)R$^5$, —C(O)—N(H)OR$^5$, —C(O)—NR$^5$R$^6$, —NR$^6$C(O)R$^5$, —NR$^6$C(O)NR$^5$R$^6$, —OC(O)NR$^5$R$^6$, —NR$^6$C(O)OR$^5$, —S(O)$_n$—R$^5$, —S(O)$_2$—NH$_2$, —S(O)$_n$—N(H)R$^5$ and —S(O)$_2$—NR$^5$R$^6$;

n is 0, 1 or 2;

R$^2$ is selected from the group consisting of hydrogen, C$_1$-C$_6$ straight alkyl, and C$_1$-C$_6$ branched alkyl, wherein all may be optionally substituted by one or more selected from the group consisting of halo, hydroxy, heterocyclic, heteroaryl, carboxy, —NR$^5$R$^6$, alkoxycarbonyl, —NR$^6$C(O)R$^5$, —NR$^6$C(O)NR$^5$R$^6$, —NR$^6$C(O)OR$^5$, —OC(O)NR$^5$R$^6$, —OR$^5$, —C(O)R$^5$, —S(O)$_n$—R$^5$, —C(O)—NR$^5$R$^6$, and cyano;

R$^3$ and R$^4$ are independently selected from the group consisting of C$_1$-C$_6$ straight alkyl, C$_1$-C$_6$ branched alkyl, and C$_3$-C$_8$ cyclic alkyl;

R$^5$ and R$^6$ are independently selected from the group consisting of hydrogen, C$_1$-C$_6$ straight alkyl, C$_1$-C$_6$ branched alkyl, C$_2$-C$_6$ alkenyl, C$_3$-C$_8$ cyclic alkyl, aryl, heteroaryl, heterocycle, and acyl, wherein all may be optionally substituted by one or more substituents independently selected from the group consisting of halo, alkyl, alkenyl, cycloalkyl, acyl, hydroxy, hydroxyalkyl, heterocyclic, heteroaryl, aryl, amino, aminoalkyl, —NR$^7$R$^8$, oxo, cyano, carboxy, carboxyalkyl, alkoxycarbonyl, —OR$^9$, —C(O)R$^9$, —C(O)—NH$_2$, —C(O)—N(H)R$^7$, —C(O)—NR$^7$R$^8$, —NR$^7$C(O)R$^9$, —NR$^7$C(O)OR$^9$, —S(O)$_n$—R$^9$, —S(O)$_2$—NH$_2$, —S(O)$_2$—N(H)R$^7$ and —S(O)$_2$—NR$^7$R$^8$; and R$^5$ and R$^6$ taken together may form a 4- to 12-membered monocyclic, bicyclic, tricyclic or benzofused ring;

R$^7$ and R$^8$ are independently selected from the group consisting of alkyl, alkenyl and aryl and taken together may form a 4- to 12-membered monocyclic, bicyclic, tricyclic or benzofused ring; and R$^9$ is independently selected from the group consisting of C$_1$-C$_6$ straight alkyl, C$_1$-C$_6$ branched alkyl, C$_2$-C$_6$ alkenyl, C$_3$-C$_8$ cyclic alkyl, heterocyclic, heteroaryl and aryl, wherein all may be substituted by one or more substituents independently selected from the group consisting of halo, alkyl, acyl, hydroxy, hydroxyalkyl, heterocyclic, heteroaryl, aryl, amino, aminoalkyl, and carboxy.

2. The compound of claim 1 wherein the compound is of Formula II:

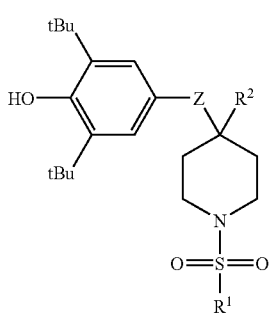

(II)

or its pharmaceutically acceptable salt.

3. The compound of claim 1, wherein the compound is of Formula III:

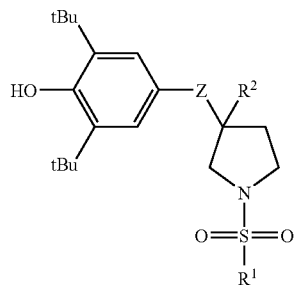

(III)

or its pharmaceutically acceptable salt.

4. The compound of one of claim 1, 2 or 3, wherein $R^1$ is heteroaryl.

5. The compound of claim 1 wherein $R^1$ is a nitrogen-containing heteroaryl.

6. The compound of claim 1 wherein $R^1$ is an oxygen-containing heteroaryl.

7. The compound of claim 1 wherein $R^1$ is a sulfur-containing heteroaryl.

8. The compound of claim 1 wherein $R^1$ is substituted with one or more substituents independently selected from alkyl, hydroxyalkyl, carboxy or carboxyalkyl.

9. The compound of claim 1, wherein $R^1$ is selected from the group consisting of furyl, thienyl, thiazolyl, pyrazolyl, pyrrolyl, benzimidazolyl and imidazolyl, wherein all may be substituted by one or more substituents independently selected from the group consisting of fluoro, chloro, bromo, iodo, trifluoromethyl, methyl, ethyl, iso-propyl, tert-butyl, hydroxymethyl, 2-methyl-2-hydroxyethyl, amino, carboxy and carboxymethyl.

10. The compound of claim 1 wherein $R^2$ is hydrogen or $C_1$-$C_4$ alkyl, wherein the $C_1$-$C_4$ alkyl is substituted by one or more substituents independently selected from the group consisting of hydroxy, cyano and heteroaryl.

11. The compound of claim 1 wherein $R^2$ is selected from the group consisting of hydrogen, cyanomethyl, tetrazolylmethyl, imidazolylethyl, hydroxymethyl, 2-methyl-2-hydroxypropyl, and hydroxyethyl.

12. The compound of claim 2 or its pharmaceutically acceptable salt, wherein:
m is 0 or 1; and
$R^2$ is hydrogen or $C_1$-$C_4$ alkyl, wherein the $C_1$-$C_4$ alkyl is substituted by one or more hydroxy, cyano and heteroaryl.

13. The compound of claim 12, wherein:
$R^1$ is selected from the group consisting of furyl, thienyl, thiazolyl, pyrazolyl, pyrrolyl and imidazolyl, wherein all may be substituted by one or more substituents independently selected from the group consisting of fluoro, chloro, trifluoromethyl, methyl, hydroxymethyl, 2-methyl-2-hydroxyethyl, amino, carboxy and carboxymethyl; and
$R^2$ is selected from the group consisting of hydrogen, hydroxymethyl, 2-methyl-2-hydroxypropyl, and hydroxyethyl.

14. The compound of claim 13, wherein:
m is 0 or 1;
$R^1$ is pyrrolyl or imidazolyl, wherein all may be substituted by one or more substituents independently selected from the group consisting of methyl, hydroxymethyl, 2-methyl-2-hydroxyethyl, carboxy and carboxymethyl; and
$R^2$ is selected from the group consisting of hydrogen, hydroxymethyl, 2-methyl-2-hydroxypropyl, and hydroxyethyl.

15. The compound of claim 1, wherein $R^1$ is N-methylpyrrolyl optionally substituted with one or more substituents independently selected from the group consisting of hydroxyalkyl, carboxy, and carboxyalkyl.

16. The compound of claim 15, wherein $R^1$ is N-methylpyrrolyl optionally substituted with one or more substituents independently selected from the group consisting of hydroxymethyl and carboxy.

17. The compound of claim 3, wherein:
m is 0 or 1; and
$R^2$ is hydrogen.

18. A pharmaceutical composition comprising a compound of claim 1, or a pharmaceutically acceptable salt thereof, optionally in a pharmaceutically acceptable carrier.

19. The pharmaceutical composition of claim 18 comprising in combination with one or more anti-inflammatory agent or bronchodilator.

20. The pharmaceutical composition of claim 19, wherein one or more of the anti-inflammatory agent or bronchodilator is selected from the group consisting of corticosteroids, mast cell stabilizers, and a leukotriene modifier drug.

* * * * *